US009567572B2

(12) United States Patent
Koppaka et al.

(10) Patent No.: US 9,567,572 B2
(45) Date of Patent: *Feb. 14, 2017

(54) MANUFACTURE OF ACTIVE HIGHLY PHOSPHORYLATED HUMAN N-ACETYLGALACTOSAMINE-6-SULFATASE AND USES THEREOF

(71) Applicant: BioMarin Pharmaceutical Inc., Novato, CA (US)

(72) Inventors: Vish Koppaka, San Rafael, CA (US); Michel Claude Vellard, San Rafael, CA (US); Augustus O. Okhamafe, Concord, CA (US); Kidisti Araya, Berkeley, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/573,907

(22) Filed: Dec. 17, 2014

(65) Prior Publication Data

US 2016/0186149 A1   Jun. 30, 2016

Related U.S. Application Data

(63) Continuation of application No. 14/281,538, filed on May 19, 2014, now Pat. No. 8,904,513, which is a continuation of application No. 13/188,907, filed on Jul. 22, 2011, now Pat. No. 8,765,437.

(60) Provisional application No. 61/366,714, filed on Jul. 22, 2010.

(51) Int. Cl.
*C12N 9/16* (2006.01)
*A61K 9/08* (2006.01)
*A61K 38/46* (2006.01)
*A61K 38/00* (2006.01)

(52) U.S. Cl.
CPC . *C12N 9/16* (2013.01); *A61K 9/08* (2013.01); *A61K 38/465* (2013.01); *A61K 38/00* (2013.01); *C12Y 301/06004* (2013.01)

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 4,391,904 | A | 7/1983 | Litman et al. |
| 4,394,448 | A | 7/1983 | Szoka, Jr. et al. |
| 5,186,941 | A | 2/1993 | Callahan et al. |
| 5,962,012 | A | 10/1999 | Lin et al. |
| 6,261,595 | B1 | 7/2001 | Stanley et al. |
| 6,303,379 | B1 | 10/2001 | Selden et al. |
| 6,355,241 | B1 | 3/2002 | Selden et al. |
| 6,537,785 | B1 | 3/2003 | Canfield |
| 6,689,600 | B1 | 2/2004 | Wu et al. |
| 2004/0229250 | A1 | 11/2004 | Figura et al. |
| 2005/0123949 | A1 | 6/2005 | Fraser |
| 2008/0231439 | A1 | 9/2008 | Wu |
| 2009/0186011 | A1 | 7/2009 | Vellard et al. |
| 2010/0068195 | A1 | 3/2010 | Vellard et al. |

FOREIGN PATENT DOCUMENTS

| | | |
|---|---|---|
| JP | 62122588 | 6/1987 |
| WO | WO-96/11953 A1 | 4/1996 |

OTHER PUBLICATIONS

Bhaumik et al., A mouse model for mucopolysaccharidosis type III A (Sanfilippo syndrome). *Glycobiology*, 9(12):1389-96 (1999).
Bielicki et al., Expression, purification and characterization of recombinant human N-acetylgalactosamine-6-sulphatase. *Biochem. J.*, 311 (Pt. 1):333-9 (1995).
Bielicki et al., Human liver N-acetylgalactosamine 6-sulphatase. Purification and characterization. *Biochem. J.*, 279 (Pt. 2):515-20 (1991).
Braulke et al., On the effects of weak bases and monensin on sorting and processing of lysosomal enzymes in human cells. *Eur. J. Cell Biol.*, 43(3):316-21 (1987).
Cacia et al., Human DNase I contains mannose 6-phosphate and binds the cation-independent mannose 6-phosphate receptor. *Biochemistry*, 37(43):15154-61 (1998).
Cardone et al., Correction of Hunter syndrome in the MPSII mouse model by AAV2/8-mediated gene delivery. *Hum. Mol. Genet.*, 15(7):1225-36 (2006).
Dierks et al., Conversion of cysteine to formylglycine: a protein modification in the endoplasmic reticulum. *Proc. Natl. Acad. Sci. U.S.A.*, 94(22):11963-8 (1997).
Diez-Roux et al., Sulfatases and human disease. *Annu. Rev. Genomics Hum. Genet.*, 6:355-79 (2005).
Evers et al., Targeted disruption of the arylsulfatase B gene results in mice resembling the phenotype of mucopolysaccharidosis VI. *Proc. Natl. Acad. Sci. U.S.A.*, 93(16):8214-9 (1996).
Feng et al., Progressive sequence alignment as a prerequisite to correct phylogenetic trees. *J. Mol. Evol.*, 25(4):351-60 (1987).
Hague et al., Structural determination of oligosaccharides from recombinant iduronidase released with peptide N-glycanase F using fluorophore-assisted carbohydrate electrophoresis. *Electrophoresis*, 19(15):2612-20 (1998).
Henikoff et al., Amino acid substitution matrices from protein blocks. *Proc. Natl. Acad. Sci. U.S.A.*, 89(22):10915-9 (1992).
Hess et al., Phenotype of arylsulfatase A-deficient mice: relationship to human metachromatic leukodystrophy. *Proc. Natl. Acad. Sci. U.S.A.*, 93(25):14821-6 (1996).

(Continued)

*Primary Examiner* — Suzanne M Noakes
*Assistant Examiner* — Jae W Lee
(74) *Attorney, Agent, or Firm* — Marshall, Gerstein & Borun LLP

(57) ABSTRACT

This invention provides compositions of active highly phosphorylated human N-acetylgalactosamine-6-sulfatase (GALNS), and pharmaceutical compositions and formulations thereof, methods of producing and purifying GALNS, and its use in the diagnosis, prophylaxis, or treatment of diseases and conditions, including particularly lysosomal storage diseases that are caused by, or associated with, a deficiency in the GALNS enzyme, e.g., Mucopolysaccharidosis IVa (MPS IVa or Morquio A syndrome).

19 Claims, 19 Drawing Sheets

(56) References Cited

OTHER PUBLICATIONS

Higgins et al., Fast and sensitive multiple sequence alignments on a microcomputer. *Comput. Appl. Biosci.*, 5(2):151-3 (1989).
International Search Report of the International Searching Authority, PCT/US2011/045011, European Searching Authority, dated Apr. 5, 2012.
Kakkis et al., Enzyme replacement therapy for the mucopolysaccharide storage disorders. *Expert Opin. Investig. Drugs*, 11(5):675-85 (2002).
Karlin et al., Applications and statistics for multiple high-scoring segments in molecular sequences. *Proc. Natl. Acad. Sci. U.S.A.*, 90(12):5873-7 (1993).
Kyte et al., A simple method for displaying the hydropathic character of a protein. *J. Mol. Biol.*, 157(1):105-32 (1982).
Lamari et al., Ultrasensitive capillary electrophoresis of sulfated disaccharides in chondroitin/dermatan sulfates by laser-induced fluorescence after derivatization with 2-aminoacridone. *J. Chromatogr. B. Biomed. Sci. Appl.*, 730(1):129-33 (1999).
Ma et al., Carbohydrate analysis of a chimeric recombinant monoclonal antibody by capillary electrophoresis with laser-induced fluorescence detection. *Anal. Chem.*, 71(22):5185-92 (1999).
Marnell et al., A Chinese hamster ovary cell mutant with a heat-sensitive, conditional-lethal defect in vacuolar function. *J. Cell Biol.*, 99(6):1907-16 (1984).
Masue et al., N-acetylgalactosamine-6-sulfate sulfatase in human placenta: purification and characteristics. *J. Biochem.*, 110(6):965-70 (1991).
Muenzer et al., Enzyme replacement therapy in mucopolysaccharidosis type II (Hunter syndrome): a preliminary report. *Acta Paediatr. Suppl.*, 91(439):98-9 (2002).
Munier-Lehmann et al., Function of the two mannose 6-phosphate receptors in lysosomal enzyme transport. *Biochem. Soc. Trans.*, 24(1):133-6 (1996).
Needleman et al., A general method applicable to the search for similarities in the amino acid sequence of two proteins. *J. Mol. Biol.*, 48(3):443-53 (1970).
Nishi et al., The vacuolar (H+)-ATPases—nature's most versatile proton pumps. *Nat. Rev. Mol. Cell Biol.*, 3(2):94-103 (2002).
Park et al., Biosynthesis of lysosomal enzymes in cells of the End3 complementation group conditionally defective in endosomal acidification. *Somat. Cell Mol. Genet.*, 17(2):137-50 (1991).
Pearson et al., Improved tools for biological sequence comparison. *Proc. Natl. Acad. Sci. U.S.A.*, 85(8):2444-8 (1988).
Rodriguez et al., Enzyme replacement therapy for Morquio A: an active recombinant N-acetylgalactosamine-6-sulfate sulfatase produced in *Escherichia coli* BL21. *J. Ind. Microbiol. Biotechnol.*, 37(11):1193-201 (2010).
Settembre et al., Systemic inflammation and neurodegeneration in a mouse model of multiple sulfatase deficiency. *Proc. Natl. Acad. Sci. U.S.A.*, 104(11):4506-11 (2007).
Sinacore et al., Adaptation of mammalian cells to growth in serum-free media. *Mol. Biotechnol.*, 15(3):249-57 (2000).
Smith et al., Comparison of biosequences. *Adv. Appl. Math.*, 2:482-9 (1981).
Stone et al., Thermolabile proton translocating ATPase and pump activities in a clathrin-coated vesicle fraction from an acidification defective Chinese hamster cell line. *J. Biol. Chem.*, 262(20):9883-6 (1987).
Sukegawa, Biochemical and structural analysis of missense mutations in N-acetylgalactosamine-6-sulfate sulfatase causing mucopolysaccharidosis IVA phenotypes. *Hum. Mol. Genet.*, 9(9):1283-90 (2000).
Thompson et al., Clustal W: improving the sensitivity of progressive multiple sequence alignment through sequence weighting, position-specific gap penalties and weight matrix choice. *Nucleic Acids Res.*, 22(22):4673-80 (1994).
Timchak et al., A thermosensitive lesion in a Chinese hamster cell mutant causing differential effects on the acidification of endosomes and lysosomes. *J. Biol. Chem.*, 261(30):14154-9 (1986).
Tomatsu et al., Characterization and pharmacokinetic study of recombinant human N-acetylgalactosamine-6-sulfate sulfatase. *Mol. Genet. Metab.*, 91(1):69-78 (2007).
Tomatsu et al., Development of MPS IVA mouse (Galnstm(hC79S.mC76S)slu) tolerant to human N-acetylgalactosamine-6-sulfate sulfatase. *Hum. Mol. Genet.*, 14(22):3321-35 (2005).
Tomatsu et al., Morquio disease: isolation, characterization and expression of full-length Cdna for human N-acetylgalactosamine-6-sulfate sulfatase. *Biochem. Biophys. Res. Commun.*, 181(2):677-83 (1991).
Tomatsu et al., Mouse model of N-acetylgalactosamine-6-sulfate sulfatase deficiency (Gains-/-) produced by targeted disruption of the gene defective in Morquio A disease. *Hum. Mol. Genet.*, 12(24):3349-58 (2003).
Tong et al., Ligand interactions of the cation-independent mannose 6-phosphate receptor. The stoichiometry of mannose 6-phosphate binding. *J. Biol. Chem.*, 264(14):7962-9 (1989).
Volpi et al., Capillary electrophoresis of complex natural polysaccharides. *Electrophoresis*, 29(15):3095-106 (2008).
Zinellu et al., A novel LIF-CE method for the separation of hyaluronan- and chondroitin sulfate-derived disaccharides: application to structural and quantitative analyses of human plasma low- and high-charged chondroitin sulfate isomers. *Electrophoresis*, 28(14):2439-47 (2007).

FIGURE 1

HUMAN SULFATASE MODIFYING FACTOR 1 (SUMF1) POLYNUCLEOTIDE SEQUENCE (SEQ ID NO:1)

```
ATGGCTGCGCCCGCACTAGGGCTGGTGTGTGGACGTTGCCCTGAGCTGGGTCTCGTCCTCTTGCTGCTGCTGCTC
TCGCTGCTGTGTGGAGCGGCAGGGAGCCAGGAGGCCGGGACCGGTGCGGGCGCGGGGTCCCTTGCGGGTTCTTGC
GGCTGCGGCACGCCCCAGCGGCCTGGCGCCCATGGCAGTTCGGCAGCCGCTCACCGATACTCGCGGGAGGCTAAC
GCTCCGGGCCCCGTACCCGGAGAGCGGCAACTCGCGCACTCAAAGATGGTCCCCATCCCTGCTGGAGTATTTACA
ATGGGCACAGATGATCCTCAGATAAAGCAGGATGGGGAAGCACCTGCGAGGAGAGTTACTATTGATGCCTTTTAC
ATGGATGCCTATGAAGTCAGTAATACTGAATTTGAGAAGTTTGTGAACTCAACTGGCTATTTGACAGAGGCTGAG
AAGTTTGGCGACTCCTTTGTCTTTGAAGGCATGTTGAGTGAGCAAGTGAAGACCAATATTCAACAGGCAGTTGCA
GCTGCTCCCTGGTGGTTACCTGTGAAAGGCGCTAACTGGAGACACCCAGAAGGGCCTGACTCTACTATTCTGCAC
AGGCCGGATCATCCAGTTCTCCATGTGTCCTGGAATGATGCGGTTGCCTACTGCACTTGGGCAGGGAAGCGGCTG
CCCACGGAAGCTGAGTGGGAATACAGCTGTCGAGGAGGCCTGCATAATAGACTTTTCCCCTGGGGCAACAAACTG
CAGCCCAAAGGCCAGCATTATGCCAACATTTGGCAGGGCGAGTTTCCGGTGACCAACACTGGTGAGGATGGCTTC
CAAGGAACTGCGCCTGTTGATGCCTTCCCTCCCAATGGTTATGGCTTATACAACATAGTGGGGAACGCATGGGAA
TGGACTTCAGACTGGTGGACTGTTCATCATTCTGTTGAAGAAACGCTTAACCCAAAAGGTCCCCCTTCTGGGAAA
GACCGAGTGAAGAAAGGTGGATCCTACATGTGCCATAGGTCTTATTGTTACAGGTATCGCTGTGCTGCTCGGAGC
CAGAACACACCTGATAGCTCTGCTTCGAATCTGGGATTCCGCTGTGCAGCCGACCGCCTGCCCACCATGGACTGA
```

FIGURE 2

HUMAN SULFATASE MODIFYING FACTOR 1 (SUMF1) POLYPEPTIDE SEQUENCE (SEQ ID NO:2)

```
MAAPALGLVCGRCPELGLVLLLLLLSLLCGAAGSQEAGTGAGAGSLAGSCGCGTPQRPGAHGSSAAAHRYSREAN
APGPVPGERQLAHSKMVPIPAGVFTMGTDDPQIKQDGEAPARRVTIDAFYMDAYEVSNTEFEKFVNSTGYLTEAE
KFGDSFVFEGMLSEQVKTNIQQAVAAAPWWLPVKGANWRHPEGPDSTILHRPDHPVLHVSWNDAVAYCTWAGKRL
PTEAEWEYSCRGGLHNRLFPWGNKLQPKGQHYANIWQGEFPVTNTGEDGFQGTAPVDAFPPNGYGLYNIVGNAWE
 WTSDWWTVHHSVEETLNPKGPPSGKDRVKKGGSYMCHRSYCYRYRCAARSQNTPDSSASNLGFRCAADRLPTMD
```

FIGURE 3

HUMAN N-ACETYLGALACTOSAMINE-6_SULFATASE (GALNS) POLYNUCLEOTIDE SEQUENCE (SEQ ID NO:3)

```
ATGGCGGCGGTTGTCGCGGCGACGAGGTGGTGGCAGCTGTTGCTGGTGCTCAGCGCCGCGGGGATGGGGGCCTCG
GGCGCCCCGCAGCCCCCCAACATCCTGCTCCTGCTCATGGACGACATGGGATGGGGTGACCTCGGGGTGTATGGA
GAGCCCTCCAGAGAGACCCCGAATTTGGACCGGATGGCTGCAGAAGGGCTGCTTTTCCCAAACTTCTATTCTGCC
AACCCTCTGTGCTCGCCATCGAGGGCGGCACTGCTCACAGGACGGCTACCCATCCGCAATGGCTTCTACACCACC
AACGCCCATGCCAGAAACGCCTACACACCGCAGGAGATTGTGGGCGGCATCCCAGACTCGGAGCAGCTCCTGCCG
GAGCTTCTGAAGAAGGCCGGCTACGTCAGCAAGATTGTCGGCAAGTGGCATCTGGGTCACAGGCCCCAGTTCCAC
CCCCTGAAGCACGGATTTGATGAGTGGTTTGGATCCCCCAACTGCCACTTTGGACCTTATGACAACAAGGCCAGG
CCCAACATCCCTGTGTACAGGGACTGGGAGATGGTTGGCAGATATTATGAAGAATTTCCTATTAATCTGAAGACG
GGGGAAGCCAACCTCACCCAGATCTACCTGCAGGAAGCCCTGGACTTCATTAAGAGACAGGCACGGCACCACCCC
TTTTTCCTCTACTGGGCTGTCGACGCCACGCACGCACCCGTCTATGCCTCCAAACCCTTCTTGGGCACCAGTCAG
CGAGGGCGGTATGGAGACGCCGTCCGGGAGATTGATGACAGCATTGGGAAGATACTGGAGCTCCTCCAAGACCTG
CACGTCGCGGACAACACCTTCGTCTTCTTCACGTCGGACAACGGCGCTGCCCTCATTTCCGCCCCCGAACAAGGT
GGCAGCAACGGCCCCTTTCTGTGTGGGAAGCAGACCACGTTTGAAGGAGGGATGAGGGAGCCTGCCCTCGCATGG
TGGCCAGGGCACGTCACTGCAGGCCAGGTGAGCCACCAGCTGGGCAGCATCATGGACCTCTTCACCACCAGCCTG
GCCCTTGCGGGCCTGACGCCGCCCAGCGACAGGGCCATTGATGGCCTCAACCTCCTCCCCACCCTCCTGCAGGGC
CGGCTGATGGACAGGCCTATCTTCTATTACCGTGGCGACACGCTGATGGCGGCCACCCTCGGGCAGCACAAGGCT
CACTTCTGGACCTGGACCAACTCCTGGGAGAACTTCAGACAGGGCATTGATTTCTGCCCTGGGCAGAACGTTTCA
GGGGTCACAACTCACAATCTGGAAGACCACACGAAGCTGCCCCTGATCTTCCACCTGGGACGGGACCCAGGGGAG
AGGTTCCCCCTCAGCTTTGCCAGCGCCGAGTACCAGGAGGCCCTCAGCAGGATCACCTCGGTCGTCCAGCAGCAC
CAGGAGGCCTTGGTCCCCGCGCAGCCCCAGCTCAACGTGTGCAACTGGGCGGTCATGAACTGGGCACCTCCGGGC
TGTGAAAAGTTAGGGAAGTGTCTGACACCTCCAGAATCCATTCCCAAGAAGTGCCTCTGGTCCCACTAG
```

FIGURE 4

HUMAN N-ACETYLGALACTOSAMINE-6-SULFATASE (GALNS) POLYPEPTIDE SEQUENCE (SEQ ID NO:4)

MAAVVAATRWWQLLLVLSAAGMGASGAPQPPNILLLLMDDMGWGDLGVYGEPSRETPNLDRMAAEGLLFPNFYSA
NPLCSPSRAALLTGRLPIRNGFYTTNAHARNAYTPQEIVGGIPDSEQLLPELLKKAGYVSKIVGKWHLGHRPQFH
PLKHGFDEWFGSPNCHFGPYDNKARPNIPVYRDWEMVGRYYEEFPINLKTGEANLTQIYLQEALDFIKRQARHHP
FFLYWAVDATHAPVYASKPFLGTSQRGRYGDAVREIDDSIGKILELLQDLHVADNTFVFFTSDNGAALISAPEQG
GSNGPFLCGKQTTFEGGMREPALAWWPGHVTAGQVSHQLGSIMDLFTTSLALAGLTPPSDRAIDGLNLLPTLLQG
RLMDRPIFYYRGDTLMAATLGQHKAHFWTWTNSWENFRQGIDFCPGQNVSGVTTHNLEDHTKLPLIFHLGRDPGE
RFPLSFASAEYQEALSRITSVVQQHQEALVPAQPQLNVCNWAVMNWAPPGCEKLGKCLTPPESIPKKCLWSH

FIGURE 5

STRUCTURE AND CHARACTERISTICS OF SECRETED HUMAN N-ACETYLGALACTOSAMINE-6-SULFATASE (GALNS) (SEQ ID NO:5)

|     |            |            |            |            |            |            |
|-----|------------|------------|------------|------------|------------|------------|
| 1   | APQPPNILLL | LMDDMGWGDL | GVYGEPSRET | PNLDRMAAEG | LLFPNFYSAN | Processed Form |
| 51  | PLCSPSRAAL | LTGRLPIRNG | FYTTNAHARN | AYTPQEIVGG | IPDSEQLLPE |            |
| 101 | LLKKAGYVSK | IVGKWHLGHR | PQFHPLKHGF | DEWFGSPNCH | FGPYDNKARP |            |
| 151 | NIPVYRDWEM | VGRYYEEFPI | NLKTGEANLT | QIYLQEALDF | IKRQARHHPF | ~40 kDa    |
| 201 | FLYWAVDATH | APVYASKPFL | GTSQRGRYGD | AVREIDDSIG | KILELLQDLH |            |
| 251 | VADNTFVFFT | SDNGAALISA | PEQGGSNGPF | LCGKQTTFEG | GMREPALAWW |            |
| 301 | PGHVTAGQVS | HQLGSIMDLF | TTSLALAGLT | PPSDRAIDGL | NLLPTLLQGR |            |
| 351 | LMDRPIFYYR | GDTLMAATLG | QHKAHFWTWT | NSWENFRQGI | DFCPGQ VSG |            |
| 401 | VTTHNLEDHT | KLPLIFHLGR | DPGERFPLSF | ASAEYQEALS | RITSVVQQHQ | ~19 kDa    |
| 451 | EALVPAQPQL | NVCNWAVMNW | APPGCEKLGK | CLTPPESIPK | KCLWSH     |            |

1) Molecular weight of pre-proceeded enzyme: ~55 kDa
2) Cysteine to Cα-formylglycine conversion at position 53
3) Processed forms in lysosome joined by disulfide bridge
4) 2 N-linked glycosylation sites at positions 178 and 397
5) BisP found on Asn178, not on Asn397

Figure 9 A. Blue Sepharose 6 FF Chromatography
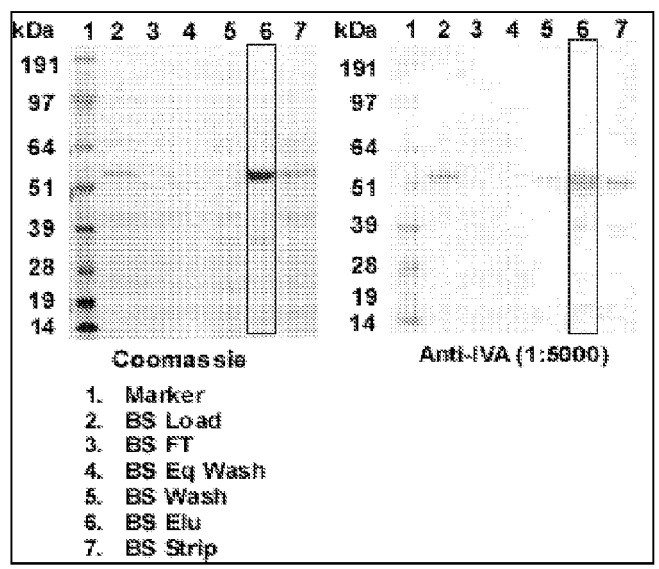
Figure 9 B. Fractogel SE Hi-Cap Chromatography
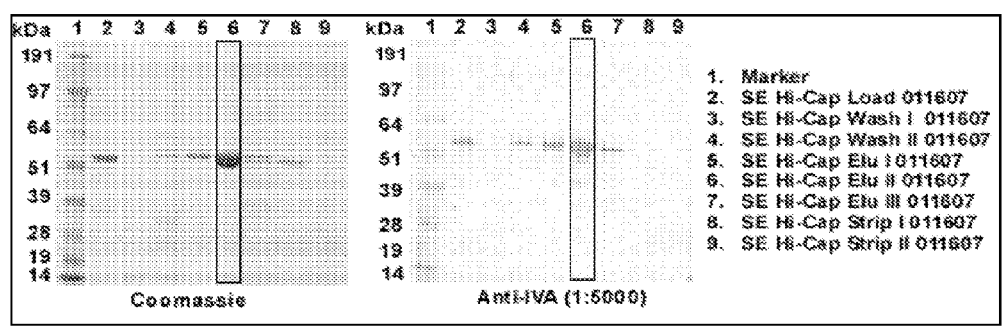

FIGURE 18

| Time 2 month- 5°C | | | | | | | | | | | | | |
|---|---|---|---|---|---|---|---|---|---|---|---|---|---|
| | 15mM L-Arginine-HCl | | | 30mM L-Arginine-HCl | | | 15mM NaCl | | | 30mM NaCl | | | |
| | pH5.0 | pH5.4 | pH 5.8 | pH5.0 | pH5.4 | pH 5.8 | pH5.0 | pH5.4 | pH 5.8 | pH5.0 | pH5.4 | pH 5.8 | Reference |
| BPM7 | 34.3 | 32.3 | 34.9 | 33.9 | 33.2 | 34.3 | 34.0 | 33.3 | 34.3 | 34.1 | 33.4 | 31.7 | 32.1 |
| Time 2 month- 25°C | | | | | | | | | | | | | |
| | 15mM L-Arginine-HCl | | | 30mM L-Arginine-HCl | | | 15mM NaCl | | | 30mM NaCl | | | |
| | pH5.0 | pH5.4 | pH 5.9 | pH5.0 | pH5.4 | pH 5.9 | pH5.0 | pH5.4 | pH 5.9 | pH5.0 | pH5.4 | pH 5.8 | Reference |
| BPM7 | 34.4 | 34.6 | 35.2 | 34.6 | 33.6 | 35.1 | 34.1 | 34.0 | 35.0 | 33.7 | 33.8 | 34.9 | 34.4 |
| Time 2 month- 40°C | | | | | | | | | | | | | |
| | 15mM L-Arginine-HCl | | | 30mM L-Arginine-HCl | | | 15mM NaCl | | | 30mM NaCl | | | |
| | pH5.0 | pH5.4 | pH 5.10 | pH5.0 | pH5.4 | pH 5.10 | pH5.0 | pH5.4 | pH 5.10 | pH5.0 | pH5.4 | pH 5.8 | Reference |
| BPM7 | 30.2 | 29.7 | 32.5 | 30.0 | 30.0 | 31.2 | 33.3 | 30.7 | 33.9 | 30.0 | 30.3 | 31.1 | 34.4 |

MANUFACTURE OF ACTIVE HIGHLY PHOSPHORYLATED HUMAN N-ACETYLGALACTOSAMINE-6-SULFATASE AND USES THEREOF

CROSS-REFERENCE TO RELATED APPLICATIONS

The present application is a continuation of U.S. patent application Ser. No. 14/281,538, filed May 19, 2014, now U.S. Pat. No. 8,940,513, issued Jan. 27, 2015, which is a continuation of U.S. patent application Ser. No. 13/188,907, filed Jul. 22, 2011, now U.S. Pat. No. 8,765,437, issued Jul. 1, 2014, which claims the priority and benefit of U.S. Provisional Application No. 61/366,714, filed Jul. 22, 2010, the disclosure of which is incorporated herein by reference in its entirety.

FIELD OF THE INVENTION

The present invention relates to the technical fields of cellular and molecular biology and medicine, particularly to the manufacture of active highly phosphorylated human lysosomal sulfatase enzymes and their use in the management of the lysosomal storage diseases associated with lysosomal sulfatase enzyme deficiency. In particular, the present invention relates to the manufacture of active highly phosphorylated recombinant human N-acetylgalactosamine-6-sulfatase (GALNS) and its use in the management of Mucopolysaccharidosis IVa (MPS IVa or Morquio A syndrome) and other lysosomal storage diseases associated with a deficiency of GALNS.

BACKGROUND OF THE INVENTION

Lysosomal storage diseases (LSDs) result from the deficiency of specific lysosomal enzymes within the cell that are essential for the degradation of cellular waste in the lysosome. A deficiency of such lysosomal enzymes leads to accumulation within the lysosome of undegraded "storage material," which causes swelling and malfunction of the lysosomes and ultimately cellular and tissue damage. A large number of lysosomal enzymes have been identified and correlated with their related diseases. Once a missing enzyme has been identified, treatment can be reduced to the sole problem of efficiently delivering a replacement enzyme to the affected tissues of patients.

One way to treat lysosomal storage diseases is by intravenous enzyme replacement therapy (ERT) (Kakkis, *Expert Opin. Investig. Drugs* 11(5): 675-685, 2002). ERT takes advantage of the vasculature to carry enzyme from a single site of administration to most tissues. Once the enzyme has been widely distributed, it must be taken up into cells. The basis for uptake into cells is found in a unique feature of lysosomal enzymes. Lysosomal enzymes constitute a separate class of glycoproteins defined by phosphate at the 6-position of terminal mannose residues. Mannose-6-phosphate is bound with high affinity and specificity by a receptor found on the surface of most cells (Munier-Lehmann et al., *Biochem. Soc. Trans.* 24(1): 133-136, 1996; Marnell et al., *J. Cell. Biol.* 99(6): 1907-1916, 1984). The mannose-6-phosphate receptor (MPR), which has two mannose-6-phosphate binding sites per polypeptides chain (Tong et al., *J. Biol. Chem.* 264:7962-7969, 1989), directs uptake of enzyme from blood to tissue and then mediates intracellular routing to the lysosome.

Large-scale production of lysosomal enzymes involves expression in mammalian cell lines. The goal is the predominant secretion of recombinant enzyme into the surrounding growth medium for harvest and processing downstream. In an ideal system for the large-scale production of lysosomal enzymes, enzyme would be efficiently phosphorylated and then directed primarily toward the cell surface (i.e., for secretion), rather than primarily to the lysosome. As described above, this partitioning of phosphorylated lysosomal enzymes is the exact opposite of what occurs in normal cells. Manufacturing cell lines used for lysosomal enzyme production focuses on maximizing the level of mannose-6-phosphate per mole of enzyme, but is characterized by low specific productivity. In vitro attempts at producing lysosomal enzymes containing high levels of mannose-6-phosphate moieties have resulted in mixed success (Canfield et al., U.S. Pat. No. 6,537,785). The in vitro enzyme exhibits high levels of mannose-6-phosphate, as well as high levels of unmodified terminal mannose. Competition between the mannose-6-phosphate and mannose receptors for lysosomal enzyme results in the necessity for high doses of enzyme for effectiveness, and could lead to greater immunogenicity to the detriment of the subject being treated.

Sulfatases constitute a unique subclass of lysosomal enzymes. Sulfatases cleave sulfate esters from a variety of substrates, including, for example, steroids, carbohydrates, proteolgycans and glycolipids. All known eukaryotic sulfatases contain a cysteine residue at their catalytic site. Sulfatase activity requires post-translational modification of this cysteine residue to $C_\alpha$-formylglycine (FGly). The cysteine to FGly post-translational enzyme activation occurs within the endoplasmic reticulum on unfolded sulfatases immediately after translation, prior to targeting of the sulfatases to the lysosome (Dierks et al., *Proc. Natl. Acad. Sci. USA* 94:11963-11968, 1997). The formylglycine-generating enzyme that catalyzes this reaction is sulfatase modifying factor 1 (SUMF1). Highlighting the importance of this unique post-translational modification is the fact that mutations in SUMF1, which result in impaired FGly formation in lysosomal sulfatase enzymes, cause Multiple Sulfatase Deficiency (MSD) in man (Diez-Ruiz et al., *Annu. Rev. Genomics Hum. Genet.* 6:355-379, 2005).

Accordingly, the therapeutic effectiveness of a lysosomal sulfatase enzyme preparation depends on the level of mannose-6-phosphate, and on the presence of active enzyme, in that preparation.

Thus, there exists a need in the art for an efficient and productive system for the large-scale manufacture of therapeutically effective, active highly phosphorylated lysosomal sulfatase enzymes for management of lysosomal storage disorders caused by or associated with a deficiency of such lysosomal sulfatase enzymes.

SUMMARY OF INVENTION

The present invention relates to the discovery that when a CHO-K1 cell line derivative (designated G71) that is defective in endosomal acidification is engineered to express recombinant human sulfatase modifying factor 1 (SUMF1), the modified G71 cells produce high yields of active highly phosphorylated recombinant lysosomal sulfatase enzymes in part by preventing loss of material to the lysosomal compartment of the manufacturing cell line. In one embodiment, the invention provides an END3 complementation group cell line that co-expresses recombinant human SUMF1 and recombinant human N-acetylgalactosamine-6-sulfatase (GALNS), resulting in high yields of active highly phosphorylated enzyme. Exemplary cell lines are G71, G71S, and derivatives thereof, which retain the desired property of G71, i.e., the ability to produce high yields of activate highly phosphorylated recombinant lysosomal sulfatase enzymes. This application of an END3 complementation group modified CHO-K1 cell line co-expressing recombinant human SUMF1 and a recombinant lysosomal sulfatase enzyme would be especially useful for the manufacture of active highly phosphorylated lysosomal sulfatase enzymes to be used for management of lysosomal storage diseases by enzyme replacement therapy (ERT).

In a first aspect, the present invention features a novel method of producing active highly phosphorylated recombinant human lysosomal sulfatase enzymes or biologically active fragments, mutants, variants or derivatives thereof in an END3 complementation group CHO cell or derivative thereof in amounts that enable their therapeutic use. In a broad embodiment, the method comprises the steps of: (a) culturing a CHO-derived END3 complementation group cell or derivative thereof; (b) preparing a first mammalian expression vector capable of expressing the active highly phosphorylated recombinant human lysosomal sulfatase enzyme or biologically active fragment, mutant, variant or derivative thereof in the CHO-derived END3 complementation group cell or derivative thereof; (c) preparing a second mammalian expression vector capable of expressing recombinant human sulfatase modifying factor 1 (SUMF1) or biologically active fragment, mutant, variant or derivative thereof in the CHO-derived END3 complementation group cell or derivative thereof; (d) transfecting the CHO-derived END3 complementation group cell or derivative thereof with the first and second expression vectors; (e) selecting and cloning of a transfectant of a CHO-derived END3 complementation group cell or derivative thereof that expresses the active highly phosphorylated recombinant human lysosomal sulfatase enzyme or biologically active fragment, mutant, variant or derivative thereof; and (f) optimizing a cell culture process method for manufacturing the highly phosphorylated recombinant human lysosomal sulfatase enzyme or biologically active fragment, mutant, variant or derivative thereof. The recombinant human lysosomal sulfatase enzyme is selected from the group consisting of arylsulfatase A (ARSA), arylsulfatase B (ARSB), iduronate-2-sulfatase (IDS), sulfamidase/heparin-N-sulfatase (SGSH), N-acetylglucosamine-sulfatase (G6S) and N-acetylgalactosamine-6-sulfatase (GALNS).

The method involves the steps of transfecting a cDNA encoding all or part of the lysosomal sulfatase enzyme and a cDNA encoding all or part of the human SUMF1 into a CHO-derived END3 complementation group cell or derivative thereof. In some embodiments, the first and second expression vectors, which are capable of expressing the encoding the active highly phosphorylated recombinant human lysosomal sulfatase enzyme and human SUMF1, respectively, are transfected simultaneously into the CHO-derived END3 complementation group cell or derivative thereof. In some embodiments, the first and second expression vectors are transfected into the CHO-derived END3 complementation group cell or derivative thereof sequentially. In some embodiments, a cDNA encoding for a full-length human lysosomal sulfatase enzyme is used, whereas in other embodiments a cDNA encoding for a biologically active fragment, mutant, variant or derivative thereof is used. In some embodiments, a cDNA encoding for a full-length human SUMF1 is used, whereas in other embodiments a cDNA encoding for a biologically active fragment, mutant, variant or derivative thereof is used. In some embodiments, multiple expression vectors are used to transfer the human lysosomal sulfatase enzyme and human SUMF1 cDNAs simultaneously or sequentially into the CHO-derived END3 complementation group cell or derivative thereof. In some embodiments, a single expression vector is used to transfer the human lysosomal sulfatase enzyme and human SUMF1 cDNAs simultaneously into the CHO-derived END3 complementation group cell or derivative thereof. In a preferred embodiment, the CHO-derived END3 complementation group cell or derivative thereof is a G71 cell line, a G71S cell line, or a G71 or G71S derivative.

In a preferred embodiment, the method comprises producing an active highly phosphorylated recombinant human lysosomal sulfatase enzyme, e.g., arylsulfatase A (ARSA), arylsulfatase B (ARSB), iduronate-2-sulfatase (IDS), sulfamidase/heparin-N-sulfatase (SGSH), N-acetylglucosamine-sulfatase (G6S) or N-acetylgalacto samine-6-sulfatase (GALNS), from an END3 complementation group CHO cell line or derivative thereof. In a particularly preferred embodiment, the method comprises producing active highly phosphorylated recombinant human N-acetylgalactosamine-6-sulfatase (GALNS) from an END3complementation group CHO cell line or derivative thereof. An END3 complementation group cell line is any modified CHO cell line that retains the properties of an END3 complementation group cell line, such as defective endosomal acidification. In a preferred embodiment, the CHO-derived END3 complementation group cell or derivative thereof is a G71 cell line, a G71S cell line, or a G71 or G71S derivative.

In a second aspect, the present invention provides an endosomal acidification-deficient mammalian cell line characterized by its ability to produce active highly phosphorylated recombinant human lysosomal sulfatase enzymes in amounts that enable use of the lysosomal sulfatase enzyme therapeutically. In preferred embodiments, the invention provides CHO-K1-derived END3 complementation group cell lines, designated G71, G71S, or derivatives thereof, which are capable of producing high yields of active highly phosphorylated recombinant human lysosomal sulfatase enzymes, thereby enabling the large scale production of such therapeutic lysosomal sulfatase enzymes. In more preferred embodiments, the cell line expresses and secretes a recombinant human lysosomal sulfatase enzyme in amounts of at least about 0.5, preferably at least about 0.75, more preferably at least about 1.0, and even more preferably at least about 1.25 picograms/cell/day.

An END3 complementation group cell line is any modified CHO cell line that retains the properties of an END3 complementation group cell line, such as defective endosomal acidification. In one embodiment, the END3 complementation group CHO cell line is derived from G71 or a derivative thereof and comprises (a) an expression vector for recombinant human sulfatase modifying factor 1 (SUMF1) and (b) an expression vector for a recombinant human lysosomal sulfatase enzyme, wherein the recombinant human lysosomal sulfatase enzyme is selected from the group consisting of arylsulfatase A (ARSA), arylsulfatase B (ARSB), iduronate-2-sulfatase (IDS), sulfamidase/heparin-N-sulfatase (SGSH), N-acetylglucosamine-sulfatase (G6S) and N-acetylgalactosamine-6-sulfatase (GALNS). In a preferred embodiment, the END3complementation group CHO cell line comprises the expression vector for recombinant human N-acetylgalactosamine-6-sulfatase (GALNS). In a more preferred embodiment, the END3 complementation group CHO cell line expresses and secretes recombinant human GALNS. In another preferred embodiment, the END3 complementation group CHO cell line is selected from the group consisting of clone 4, clone 5, clone C6, clone C2, clone C5, clone C7, clone C10, clone C11 and clone C30. In a more preferred embodiment, the END3 complementation group CHO cell line is clone C2. In another preferred embodiment, the END3 complementation group CHO cell line is adapted to growth in suspension.

In a third aspect, the invention provides recombinant human lysosomal sulfatase enzymes produced in accordance with the methods of the present invention and thereby present in amounts that enable using the lysosomal sulfatase enzymes therapeutically. The lysosomal sulfatase enzymes may be full-length proteins, or fragments, mutants, variants or derivatives thereof. In some embodiments, the lysosomal sulfatase enzyme or fragment, mutant, variant or derivative thereof according to the invention may be modified as desired to enhance its stability or pharmacokinetic properties (e.g., PEGylation, mutagenesis, fusion, conjugation). In preferred embodiments, the enzyme is a human lysosomal sulfatase enzyme, a fragment of the human lysosomal sulfatase enzyme having a biological activity of a native sulfatase enzyme, or a polypeptide that has substantial amino acid sequence homology with the human lysosomal sulfatase enzyme. In some embodiments, the lysosomal sulfatase enzyme is a protein of human or mammalian sequence, origin or derivation. In other embodiments, the lysosomal sulfatase enzyme is such that its deficiency causes a human disease, such as Metachromic Leukodystrophy or MLD (i.e., arylsulfatase A (ARSA)), Maroteaux-Lamy syndrome or MPS VI (i.e., arylsulfatase B (ARSB)), Hunter syndrome or MPS II (i.e., iduronate-2-sulfatase (IDS)), Sanfilippo A syndrome or MPS IIIa (i.e., sulfamidase/heparin-N-sulfatase (SGSH)), Sanfilippo D syndrome or MPS IIId (i.e., N-acetylglucosamine-sulfatase (G6S)) and Morquio A syndrome or MPS IVa (i.e., N-acetylgalactosamine-6-sulfatase (GALNS)). In a particularly preferred embodiment, the lysosomal sulfatase enzyme is such that its deficiency causes Morquio A syndrome or MPS IVa (i.e., N-acetylgalactosamine-6-sulfatase (GALNS)). In another particularly preferred embodiment, the lysosomal sulfatase enzyme is such that its deficiency is associated with a human disease, such as Multiple Sulfatase Deficiency or MSD (i.e., N-acetylgalactosamine-6-sulfatase (GALNS)).

The lysosomal sulfatase enzyme can also be of human or mammalian sequence origin or derivation. In yet other embodiments of the invention, in each of its aspects, the lysosomal sulfatase enzyme is identical in amino acid sequence to the corresponding portion of a human or mammalian lysosomal sulfatase enzyme amino acid sequence. In other embodiments, the polypeptide moiety is the native lysosomal sulfatase enzyme from the human or mammal. In other embodiments, the lysosomal sulfatase enzyme polypeptide is substantially homologous (i.e., at least about 80%, 85%, 90%, 95%, 96%, 97%, 98%, or 99% identical in amino acid sequence) over a length of at least about 25, 50, 100, 150, or 200 amino acids, or the entire length of the polypeptide, to the native lysosomal sulfatase enzyme amino acid sequence of the human or mammalian enzyme. In some embodiments, the lysosomal sulfatase enzyme is human N-acetylgalactosamine-6-sulfatase (GALNS). The amino acid sequence of human GALNS is set forth in SEQ ID NO: 4, of which amino acids 27 to 522 correspond to the secreted precursor protein. In some embodiments, this GALNS enzyme comprises or consists of an amino acid sequence at least about 50%, 55%, 60%, 65%, 70%, 75%, 80%, 85%, 90%, 95%, 96%, 97%, 98%, or 99% identical to amino acids 27 to 522 of SEQ ID NO: 4, or a sequence identical to amino acids 27 to 522 of SEQ ID NO: 4. The GALNS enzyme preferably retains the catalytic site amino acids corresponding to the Cys at position 53 of the secreted precursor protein (amino acid 79 of SEQ ID NO: 4), which is capable of being converted to $C_\alpha$-formylglycine. The GALNS enzyme may also retain other amino acids in the active site cavity, including at least 1, 2, 3, 4, 5, 6, 7, 8 or all of the charged amino acids: Asp288, Asn289, Asp39, Asp54, His236, Lys140, His142, Lys310 and the α-helix: Arg83. Sukegawa, *Human Molecular Genetics*, 2000, Vol. 9, No. 9 1283-1290, incorporated herein by reference in its entirety, describes additional mutations that decrease GALNS activity in patients and correlates the severity of various mutations to their respective 3-dimensional location within the enzyme. In other embodiments, the subject to which the lysosomal sulfatase enzyme is to be administered is human.

In preferred embodiments, the lysosomal sulfatase enzyme is a highly phosphorylated recombinant human lysosomal sulfatase enzyme produced by an endosomal acidification-deficient cell line, e.g., a CHO-derived END3 complementation group cell line. An END3 complementation group cell line is any modified CHO cell line that retains the properties of an END3 complementation group cell line, such as defective endosomal acidification. In a preferred embodiment, the CHO-derived END3 complementation group cell or derivative thereof is a G71 cell line, a G71S cell line, or a G71 or G71S derivative. Alternatively, the lysosomal sulfatase enzyme may be produced by any host cell, e.g., any CHO cell or CHO cell-derived line, cultured under conditions that permit expression and secretion of highly phosphorylated recombinant lysosomal sulfatase enzyme at relatively high yield, e.g., in amounts of at least about 0.5, at least about 0.75, at least about 1.0, or at least about 1.25 picograms/cell/day.

In more preferred embodiments, the recombinant human lysosomal sulfatase enzyme has a high level of phosphorylated oligosaccharides (i.e., greater than about 0.25, preferably greater than 0.5, and more preferably greater than about 0.75 bis-phosphorylated oligomannose chains per protein chain).

In some embodiments, the invention provides a recombinant human lysosomal sulfatase enzyme, e.g., GALNS, with a specified high level of phosphorylated oligosaccharides. For example, the lysosomal sulfatase enzyme has from 0.5 to 1.0 bis-phosphorylated oligomannose chains per monomeric protein chain, or from 0.5 to 0.9 bis-phosphorylated oligomannose chains per monomeric protein chain, or from 0.5 to 0.8 bis-phosphorylated oligomannose chains per monomeric protein chain, or from 0.5 to 0.75 bis-phosphorylated oligomannose chains per monomeric protein chain, or from 0.54 to 0.75 bis-phosphorylated oligomannose chains per monomeric protein chain. Other similar ranges are contemplated, e.g., at least 0.4, 0.45, 0.5, 0.55, 0.6 or 0.65 bis-phosphorylated oligomannose chains per monomeric protein chain, up to 0.7, 0.75, 0.8, 0.85, 0.9, 0.95, 0.98, or 1.0 bis-phosphorylated oligomannose chains per monomeric protein chain, or any combination of any of these numbers. In preferred embodiments, the enzyme is a recombinant human N-acetylgalactosamine-6-sulfatase (GALNS), e.g., of SEQ ID NO: 4.

In some embodiments, the recombinant human lysosomal sulfatase enzyme has a high percentage (i.e., at least about 50%, 55%, 60%, or 65%, preferably at least about 70%, 75%, 80%, 85%, 90%, or 95%) of conversion of the active site cysteine residue to $C_\alpha$-formylglycine (FGly). In preferred embodiments, the enzyme is an active recombinant human N-acetylgalactosamine-6-sulfatase (GALNS) and the active site cysteine residue is the Cys at position 53 (position 79 of SEQ ID NO: 4).

In particular embodiments, the recombinant human lysosomal sulfatase enzyme has a high level of phosphorylated oligosaccharides, e.g., any of the ranges or levels of bis-phosphorylated oligomannose chains per monomeric protein chain described herein, together with a high percentage of conversion of the active site cysteine residue to $C_\alpha$-formylglycine (FGly), e.g., any of the percentages described herein. In preferred embodiments, the enzyme is an active highly phosphorylated recombinant human N-acetylgalactosamine-6-sulfatase (GALNS), e.g., of SEQ ID NO: 4.

In any of the preceding embodiments, at least 99.5%, at least 99%, at least 98.5%, at least 98%, at least 97%, at least 95%, at least 90%, at least 85%, at least 80%, at least 75%, at least 70%, or at least 65% of the recombinant human lysosomal sulfatase enzyme, e.g., GALNS (SEQ ID NO: 4), is in the precursor form as determined by COOMASSIE® Blue staining when subjected to SDS-PAGE under reducing conditions or by SDS-capillary gel electrophoresis (SDS-CGE).

In addition, the lysosomal sulfatase enzyme, e.g., GALNS (SEQ ID NO: 4), optionally also exhibits a specific activity that is at least about 30% (e.g., 35%, 40%, 45%, 50%, 55%, 60%, 65%, 70%, 75%, 80%, 85%, 90%, 95%, 2-fold, 2.5-fold, 3-fold, 4-fold, 5-fold, 10-fold, 15-fold, 20-fold, 30-fold, 40-fold or 50-fold) greater than the specific activity of a control lysosomal sulfatase enzyme of the same amino acid sequence that has been produced in host cells (e.g., CHO cells or CHO-derived cells) that do not express recombinant human SUMF1.

In any of the preceding embodiments, the lysosomal sulfatase enzyme described, e.g., GALNS (SEQ ID NO: 4), exhibits a specific uptake (Kuptake) into fibroblasts that is about 0.1 to 10 nM, or about 0.1 to 7 nM, or about 0.5 to 5 nM, or about 1 to 5 nM, or about 1 to 3.5 nM, about 1 nM, about 1.5 nM, about 2 nM, about 2.5 nM, about 3 nM or about 3.5 nM, or any combination of any of these numbers.

In any of the preceding embodiments, at least about 50%, at least about 55%, at least about 60%, at least about 65%, at least about 70%, at least about 75%, or at least about 80% of the recombinant human lysosomal sulfatase enzyme, e.g., GALNS (SEQ ID NO: 4), binds a mannose-6-phosphate receptor column.

According to this aspect, purified preparations of any of these embodiments of the lysosomal sulfatase enzyme are provided in which the lysosomal sulfatase enzyme component, e.g., GALNS (SEQ ID NO: 4) has a purity of at least about 90%, 95%, 97%, 98%, or 99% as determined by COOMASSIE® Blue staining when subjected to SDS-PAGE under non-reducing conditions or by another method of determining purity (e.g., SDS-PAGE under reducing or non-reducing conditions followed by staining with COOMASSIE® Blue or silver, or chromatographic separation by HPLC, including C4 reverse phase (RP) or C3 RP), or size exclusion chromatography (SEC)). In some embodiments, a significant amount of the lysosomal sulfatase enzyme component of the purified preparation is in the secreted precursor form (e.g., at least 65%, 70%, 75%, 80%, 85%, 90%, 95%, 97%, 98%, 98.5%, 99% or 99.5% precursor), as determined by COOMASSIE® Blue staining when subjected to SDS-PAGE under reducing conditions or by another method of detecting precursor (e.g., SDS-PAGE under reducing conditions with COOMASSIE® Blue or silver staining, or chromatographic separation by HPLC (e.g., C4 reverse phase (RP), C3 RP) or size exclusion chromatography (SEC), or a combination of electrophoretic separation and chromatographic separation, e.g., SDS-PAGE followed by capillary gel electrophoresis (SDS-CGE)).

In particular embodiments, the lysosomal sulfatase enzyme component of the purified preparation has a high level of phosphorylated oligosaccharides, e.g., any of the ranges or levels of bis-phosphorylated oligomannose chains per monomeric protein chain described herein, together with a high percentage of conversion of the active site cysteine residue to $C_\alpha$-formylglycine (FGly), e.g., any of the percentages described herein. In more particular embodiments, the purified preparation has a Kuptake as described herein.

In related aspects, the invention provides sterile compositions containing any of the lysosomal sulfatase enzyme or purified preparations described herein, together with a sterile pharmaceutically acceptable diluent, carrier and/or excipient. Such sterile compositions may take the form of solutions or lyophilized powder, optionally in vials, that may be reconstituted by the addition of sterile diluent.

In a fourth aspect, the invention provides a method to purify recombinant human lysosomal sulfatase enzymes produced by the methods of the present invention. In a preferred embodiment, lysosomal sulfatase enzymes are purified using a two-column process (dye-ligand chromatography, e.g., Blue-SEPHAROSE®, and cation exchange chromatography, e.g., SE Hi-Cap) comprising at least five purification steps: (1) filtering the harvest, i.e., culture medium from an END3 complementation group CHO cell line or derivative thereof that expresses human sulfatase modifying factor 1 (SUMF1) and the recombinant human lysosomal sulfatase enzyme; (2) pH adjusting the filtered harvest to pH 4.5 (to induce precipitation of contaminating proteins); (3) loading the pH-adjusted filtered harvest onto a dye-ligand column, e.g., Blue-SEPHAROSE® column, washing the column and eluting the lysosomal sulfatase enzyme from the column; (4) loading the eluate from the dye-ligand column onto a cation exchange column, e.g., SE Hi-Cap column, washing the column and eluting the lysosomal sulfatase enzyme from the column; and (5) ultrafiltrating and diafiltrating the eluate from the cation exchange. Optionally, the filtered harvest in step (1) is concentrated 10-20 fold by ultrafiltration before adjusting the pH. Optionally, the ultrafiltrated and diafiltrated lysosomal sulfatase enzyme in step (5) is formulated in a formulation buffer. In a particularly preferred embodiment, the lysosomal enzyme is a recombinant human N-acetylgalactosamine-6-sulfatase (GALNS).

In another preferred embodiment, lysosomal sulfatase enzymes are purified using a three-column process (capture chromatography, e.g., cation exchange SE Hi-Cap; intermediate chromatography, e.g., dye-ligand CAPTO® Blue, Zinc Chelating SEPHAROSE® FF or CAPTO® Adhere; and polishing chromatography, e.g., TOYOPEARL® Butyl 650M, Phenyl SEPHAROSE® Hi-Sub or Phenyl SEPHAROSE® Low-Sub) comprising at least five purification steps: (1) ultrafiltering the harvest, i.e., culture medium from an END3 complementation group CHO cell line or derivative thereof that expresses human sulfatase modifying factor 1(SUMF1) and the recombinant human lysosomal sulfatase enzyme, by, e.g., SARTOCON® Cassettes, (30 kDa, HYDROSART®); (2) pH adjusting the filtered harvest to pH 4.5 (to induce precipitation of contaminating proteins); (3) loading the pH-adjusted filtered harvest onto a capture column, e.g., FRACTOGEL® EMD SE Hi-CAP (M) cation exchange, washing the column and eluting the lysosomal sulfatase enzyme from the column; (4) loading the eluate from the capture column onto an intermediate column, e.g., dye-ligand CAPTO® Blue, Zinc Chelating SEPHAROSE® FF or CAPTO® Adhere, washing the column and eluting the lysosomal sulfatase enzyme from the column; and (5) loading the eluate on a polishing column, e.g., TOYOPEARL® Butyl 650 M, Phenyl SEPHAROSE® Hi-Sub or Phenyl SEPHAROSE® Low-Sub, washing the column and eluting the lysosomal sulfatase enzyme from the column. The eluted lysosomal sulfatase enzyme from step (5) is formulated in a formulation buffer. Optionally, the eluted lysosomal sulfatase enzyme from step (5) is ultrafiltrated and then formulated in a formulation buffer. Optionally, the lysosomal sulfatase enzyme from the column in step (4) is exposed to pH 3.5 for low pH viral inactivation prior to loading onto the polishing column in step (5). In a particularly preferred embodiment, the lysosomal sulfatase enzyme is a recombinant human N-acetylgalactosamine-6-sulfatase (GALNS).

In another preferred embodiment, lysosomal sulfatase enzymes are purified using a different three-column process (capture or immobilized metal affinity chromatography (IMAC), e.g., dye-ligand CAPTO® Blue, Zinc Chelating SEPHAROSE® FF or CAPTO® Adhere; intermediate chromatography, e.g., FRACTOGEL® EMD SE Hi-Cap cation exchange; and polishing chromatography, e.g., TOYOPEARL® Butyl 650M, Phenyl SEPHAROSE® Hi-Sub or Phenyl SEPHAROSE® Low-Sub) designed to reduce proteolytic digestion (i.e., clipping) of the lysosomal sulfatase enzyme comprising at least six purification steps: (1) filtering the harvest, i.e., culture medium from a mammalian cell line, e.g., an END3 complementation group CHO cell line or derivative thereof, that expresses human sulfatase modifying factor 1 (SUMF1) and the recombinant human lysosomal sulfatase enzyme, ultrafiltering/diafiltering the filtered harvest by, e.g., SARTOCON® Cassettes (30 kDa, HYDROSART®), resulting in a concentrated filtered harvest, e.g., 20× concentrated, and charcoal filtering the concentrated filtered harvest; (2) loading the charcoal filtered, concentrated harvest onto a capture or IMAC column, e.g., dye-ligand CAPTO® Blue, Zinc Chelating SEPHAROSE® FF or CAPTO® Adhere, washing the capture column under conditions such that the lysosmal sulfatase enzyme is retained on the capture column, and eluting the lysosomal sulfatase enzyme from the capture column; (3) optionally, filtering the eluate from the capture column with a filter, e.g., a MUSTANG® Q filter, for removal of viruses; (4) adjusting the pH of the eluate or filtered eluate from the capture column to an acid pH, e.g., pH 4.5±0.1, then filtering the acid pH-adjusted eluate or filtered eluate from the capture column; (5) loading the filtered, acid pH-adjusted eluate or filtered eluate from the capture column onto an intermediate column, e.g., FRACTOGEL® EMD SE Hi-CAP cation exchange column, washing the intermediate column under conditions such that the lysosomal sulfatase enzyme is retained on the intermediate column, and eluting the lysosomal sulfatase enzyme from the intermediate column; (6) adjusting the pH of the eluate from the intermediate column to low pH, e.g., pH 3.5±0.1, for viral inactivation; and (7) loading the low pH viral inactivated eluate from the intermediate cation exchange column onto a polishing column, e.g., hydrophobic interaction chromatography (HIC) column, e.g., TOYOPEARL® Butyl 650M, Phenyl SEPHAROSE® Hi-Sub or Phenyl SEPHAROSE® Low-Sub, washing the polishing column under conditions such that the lysosomal sulfatase enzyme is retained on the polishing column, and eluting the lysosomal sulfatase enzyme from the polishing column. In a preferred embodiment, step (3) is included in the purification process. In another preferred embodiment, step (3) is omitted in the purification process.

Optionally, (8) the eluted lysosomal sulfatase enzyme from step (7) is buffer exchanged into a formulation, e.g., including but not limited to those formulations described herein, such as 20 mM NaOAc/HOAc, 50 mM $NaH_2PO_4$, 30 mM arginine HCl, 2% (w/v) sorbitol, pH 5.4, and the concentration of the eluted lysosomal sulfatase enzyme in the formulation is adjusted to an appropriate concentration, e.g., 3 mg/mL; (9) any residual virus and DNA present in the formulation of purified lysosomal sulfatase enzyme are removed by filtering through a viral filter and a DNA filter; and (10) a non-ionic surfactant, e.g., polysorbate 20 (PS20 or TWEEN®-20), is added to the formulation of purified lysosomal sulfatase enzyme. The final formulation of purified lysosomal sulfatase enzyme (the Bulk Drug Substance) is stored at 2-8° C. or frozen. In a particularly preferred embodiment, steps (8) to (10) are included in the purification process. In a particularly preferred embodiment, the lysosomal sulfatase enzyme is recombinant human N-acetylgalactosamine-6-sulfatase (GALNS).

In some embodiments, the harvest is collected in step (1) at a pH of about 6.5. In some embodiments, the charcoal filter in step (1) is a ZETA PLUS® R55 Activated Carbon filter. In some embodiments, the capture column in step (2) is a Zn-IMAC column. In some embodiments, the Zn-IMAC column is a Zn-chelating SEPHAROSE® FF column. In some embodiments, the filter in step (3) is a MUSTANG® Q filter. In some embodiments, the acid pH of the eluate or filtered eluate from step (2) or (3) is adjusted in step (4) to about 4.5±0.1. In some embodiments, the intermediate column in step (5) is a cation exchange column. In some embodiments, the cation exchange column is a FRACTOGEL® EMD SE Hi-Cap column. In some embodiments, the low pH of the eluate from the intermediate column from step (6) is adjusted in step (6) to about 3.5±0.1. In some embodiments, the polishing column in step (7) is a hydrophobic interaction chromatography (HIC) column. In some embodiments, the HIC column is a TOYOPEARL® Butyl 650M column.

In some embodiments, the formulation comprises 20 mM NaOAc/HOAc, 50 mM $NaH_2PO_4$, 30mM arginine HCl, 2% (w/v) sorbitol, pH 5.4. In some embodiments, the non-ionioc surfactant is polysorbate 20 (PS20). In some embodiments, the concentration of lysosomal sulfatase enzyme in the formulation is adjusted to about 3 mg/mL. In some embodiments, the viral filter is a DV20 filter and the DNA filter is a MUSTANG® Q filter. In some embodiments, the non-ionic surfactant added to the formulation is polysorbate 20 (PS20) to a final concentration of 0.01% (w/v).

In a fifth aspect, the invention provides a purified preparation of active highly phosphorylated recombinant human N-acetylgalactosamine-6-sulfatase (GALNS) or biologically active mutant, variant or derivative thereof useful for treating a subject suffering from a lysosomal storage disease that is caused by (e.g., Mucopolysaccharidosis type IVa (MPS IVa) or Morquio A syndrome) or associated with (e.g., Multiple Sulfatase Deficiency (MSD)) a deficiency in the GALNS enzyme. In a preferred embodiment, the purified preparation of active highly phosphorylated recombinant human GALNS has a GALNS enzyme component having: (a) a purity of at least about 90%, 95%, 97%, 98%, or 99% as determined by COOMASSIE® Blue staining or silver staining when subjected to SDS-PAGE under non-reducing conditions; (b) at least about 80%, 85%, 90%, or 95% conversion of the cysteine residue at position 53 to $C_\alpha$-formylglycine (FGly) (position 79 of SEQ ID NO: 4); (c) N-linked glycosylation at the asparagine residues at positions 178 and 397, wherein some of the oligomannose chains attached to the asparagine residue at position 178 are bis-phosphorylated; (d) from 0.5 to 1.0, or from 0.5 to 0.9, or from 0.5 to 0.8, or from 0.5 to 0.75, or from 0.54 to 0.75 bis-phosphorylated oligomannose chains per monomeric protein chain (e.g., at least 0.4, 0.45, 0.5, 0.55, 0.6, or 0.65 and up to 0.7, 0.75, 0.8, 0.85, 0.9, 0.95, 0.98, or 1.0 bis-phosphorylated oligomannose chains per monomeric protein chain, or any combination of any of these numbers); and (e) at least 65%, or at least 70% (e.g., at least 75%, 80%, 85%, 90%, 95%, 97%, 98%, 98.5%, 99% or 99.5%) of the GALNS enzyme is in the precursor form as determined by COOMASSIE® Blue staining when subjected to SDS-PAGE under reducing conditions or by SDS-capillary gel electrophoresis (SDS-CGE). In addition, the GALNS enzyme may optionally also (f) exhibit a specific activity that is at least about 30% (e.g., 35%, 40%, 45%, 50%, 55%, 60%, 65%, 70%, 75%, 80%, 85%, 90%, 95%, 2-fold, 2.5-fold, 3-fold, 4-fold, 5-fold, 10-fold, 15-fold, 20-fold, 30-fold, 40-fold or 50-fold) greater than the specific activity of a control GALNS enzyme of the same amino acid sequence that has been produced in host cells (e.g., CHO cells or CHO-derived cells) that do not express recombinant human SUMF1. Optionally, the GALNS enzyme exhibits a specific uptake (Kuptake) into fibroblasts that is about 0.1 to 10 nM, or about 0.1 to 7 nM, or about 0.5 to 5 nM, or about 1 to 5 nM, or about 1 to 3.5 nM, about 1 nM, about 1.5 nM, about 2 nM, about 2.5 nM, about 3 nM or about 3.5 nM, or any combination of any of these numbers.

The purified, active highly phosphorylated recombinant human GALNS consists of a major band of about 55-60 kDa (i.e., precursor human GALNS being at least about 75%, or at least 80%, preferably at least about 85%, more preferably at least about 90%, and even more preferably at least about 95%, at least 97%, at least 98%, at least 98.5%, at least 99%, or at least 99.5% of the visible proteins) and minor bands at ~39 kDa and ~19 kDa (i.e., mature or processed human GALNS being less than about 25%, less than about 20%, preferably less than about 15%, more preferably less than about 10%, and even more preferably less than about 5%, less than about 3%, less than about 2%, less than about 1.5%, less than about 1% or less than about 0.5% of the visible proteins) when subjected to SDS-PAGE under reducing conditions, or as determined by SDS-CGE. In a particularly preferred embodiment, the purified, active highly phosphorylated recombinant human GALNS consists essentially of a single band of about 55-60 kDa (i.e., precursor human GALNS) when subjected to SDS-PAGE under reducing conditions, or as determined by SDS-CGE. In one embodiment, the purified, active highly phosphorylated recombinant human GALNS is useful for treating MPS IVa or Morquio A syndrome. In one embodiment, the purified, active highly phosphorylated recombinant human GALNS is useful for treating MSD.

In a sixth aspect, the invention provides a method of treating diseases caused all or in part by deficiency, or are associated with a deficiency, of a lysosomal sulfatase enzyme. The method comprises administering a therapeutic recombinant human lysosomal sulfatase enzyme produced by the methods of the present invention, wherein the lysosomal sulfatase enzyme binds to an MPR receptor and is transported across the cell membrane, enters the cell and is delivered to the lysosomes within the cell.

In one embodiment, the method comprises treating a subject suffering from a deficiency of a lysosomal sulfatase enzyme comprising administering to the subject in need thereof a therapeutically effective amount of said lysosomal sulfatase enzyme, wherein said lysosomal sulfatase enzyme is a recombinant human lysosomal sulfatase enzyme or biologically active fragment, mutant, variant or derivative thereof produced by a CHO-derived END3 complementation group cell or a derivative thereof. In some embodiments, the method comprises administering a therapeutic recombinant human lysosomal sulfatase enzyme, or a biologically active fragment, mutant, variant or derivative thereof, alone or in combination with a pharmaceutically acceptable carrier, diluent or excipient. Preferred embodiments include optimizing the dosage to the needs of the subjects to be treated, preferably mammals and most preferably humans, to most effectively ameliorate the deficiency of the lysosomal sulfatase enzyme.

Such therapeutic lysosomal sulfatase enzymes are particularly useful, for example, in the treatment of patients suffering from lysosomal storage diseases caused by a deficiency of a lysosomal sulfatase enzyme, such as patients suffering from Metachromatic Leukodystrophy or MLD, Mucopolysaccharidosis type VI (MPS VI) or Maroteaux-Lamy syndrome, Mucopolysaccharidosis type II (MPS II) or Hunter syndrome, Mucopolysaccharidosis type IIIa (MPS IIIa) or Sanfilippo A syndrome, Mucopolysaccharidosis type IIId (MPS IIId) or Sanfilippo D syndrome, and Mucopolysaccharidosis type IVa (MPS IVa) or Morquio A syndrome. In a particularly preferred embodiment, the lysosomal storage disease is MPS IVa or Morquio A syndrome and the lysosomal sulfatase enzyme is recombinant human N-acetylgalactosamine-6-sulfatase (GALNS). In yet other embodiments, the invention also provides pharmaceutical compositions comprising the deficient lysosomal sulfatase enzyme causing the lysosomal storage disease and a pharmaceutically acceptable carrier, diluent or excipient.

In another embodiment, the method comprises treating a subject suffering from a lysosomal storage disease that is associated with a deficiency in one or more lysosomal sulfatase enzymes comprising administering to the subject in need thereof a therapeutically effective amount of a lysosomal sulfatase enzyme, wherein said lysosomal sulfatase enzyme is a recombinant human N-acetylgalactosamine-6-sulfatase (GALNS) or biologically active fragment, mutant, variant or derivative thereof produced by a CHO-derived END3 complementation group cell or a derivative thereof. In some embodiments, the method comprises administering therapeutic recombinant human GALNS enzyme or a biologically active fragment, mutant, variant or derivative thereof alone or in combination with a pharmaceutically acceptable carrier, diluent or excipient. In a particularly preferred embodiment, the lysosomal storage disease is Multiple Sulfatase Deficiency (MSD).

In particularly preferred embodiments, the CHO-derived END3 complementation group cell or a derivative thereof is a G71 cell line, a G71S cell line or a G71 or G71S derivative thereof.

In still another embodiment, the present invention provides for a method of enzyme replacement therapy by administering a therapeutically effective amount of lysosomal sulfatase enzyme to a subject in need of the enzyme replacement therapy, wherein the cells of the patient have lysosomes which contain insufficient amounts of the lysosmal sulfatase enzyme to prevent or reduce damage to the cells, whereby sufficient amounts of the lysosomal sulfatase enzyme enter the lysosomes to prevent or reduce damage to the cells. The cells may be within or without the CNS or need not be set off from the blood by capillary walls whose endothelial cells are closely sealed to diffusion of an active agent by tight junctions.

In a particular embodiment, the invention provides compositions and pharmaceutical compositions comprising an active recombinant human lysosomal sulfatase enzyme having a biological activity which is reduced, deficient, or absent in the target lysosome and which is administered to the subject. Preferred active human lysosomal sulfatase enzymes include, but are not limited to, arylsulfatase A, arylsulfatse B, iduronate-2-sulfatase, sulfamidase/heparan-N-sulfatase, N-acetylglucosamine-6-sulfatase, and N-acetylgalactosamine-6-sulfatase. In a preferred embodiment, N-acetylgalactosamine-6-sulfatase is the active recombinant human lysosomal sulfatase enzyme.

In a preferred embodiment, the invention provides a method of treating a subject suffering from MPS IVa or Morquio A syndrome, or MSD, by administering to the subject a therapeutically effective amount of any of the recombinant human N-acetylgalactosamine-6-sulfatase (GALNS), purified preparations and/or sterile compositions described herein.

In a more preferred embodiment, the invention provides a method of treating a subject suffering from MPS IVa or Morquio A syndrome, or MSD, by administering to the subject a therapeutically effective amount of recombinant human N-acetylgalactosamine-6-sulfatase (GALNS) produced by END3complementation group cells, wherein the recombinant human GALNS has a high level of conversion of the active site cysteine residue to $C_\alpha$-formylglycine (FGly) (i.e., at least about 50%, preferably at least about 70%, more preferably at least about 90%, even more preferably at least about 95% conversion), and high levels of phosphorylation (i.e., greater than about 0.25, preferably greater than 0.5, and more preferably greater than about 0.75 bis-phosphorylated oligomannose chains per protein chain).

In a particularly preferred embodiment, the invention provides a method of treating a subject suffering from MPS IVa or Morquio A syndrome, or MSD, by administering to the subject a therapeutically effective amount of a purified, active highly phosphorylated recombinant human GALNS preparation that has a GALNS enzyme component having: (a) a purity of at least about 90%, 95%, 97%, 98% or 99% as determined by COOMASSIE® Blue staining or silver staining when subjected to SDS-PAGE under non-reducing conditions; (b) at least about 80%, 85%, 90% or 95% conversion of the cysteine residue at position 53 to $C_\alpha$-formylglycine (FGly) (position 79 of SEQ ID NO: 4); (c) from 0.5 to 1.0, or from 0.5 to 0.9, or from 0.5 to 0.8, or from 0.5 to 0.75, or from 0.54 to 0.75 bis-phosphorylated oligomannose chains per monomeric protein chain (e.g., at least 0.4, 0.45, 0.5, 0.55, 0.6 or 0.65 and up to 0.7, 0.75, 0.8, 0.85, 0.9, 0.95, 0.98, or 1.0 bis-phosphorylated oligomannose chains per monomeric protein chain, or any combination of any of these numbers); and (d) at least 65%, or at least 70% (e.g., at least 75%, 80%, 85%, 90%, 95%, 97%, 98%, 98.5%, 99% or 99.5%) of the GALNS enzyme is in the precursor form as determined by COOMASSIE® Blue staining when subjected to SDS-PAGE under reducing conditions or by SDS-capillary gel electrophoresis (SDS-CGE). In addition, the GALNS enzyme may optionally also (e) exhibit a specific activity that is at least about 30% (e.g., 35%, 40%, 45%, 50%, 55%, 60%, 65%, 70%, 75%, 80%, 85%, 90%, 95%, 2-fold, 2.5-fold, 3-fold, 4-fold, 5-fold, 10-fold, 15-fold, 20-fold, 30-fold, 40-fold or 50-fold) greater than the specific activity of a control GALNS enzyme of the same amino acid sequence that has been produced in host cells (e.g., CHO cells or CHO-derived cells) that do not express recombinant human SUMF1. Optionally, the GALNS enzyme exhibits a specific uptake (Kuptake) into fibroblasts that is about 0.1 to 10 nM, or about 0.1 to 7 nM, or about 0.5 to 5 nM, or about 1 to 5 nM, or about 1 to 3.5 nM, about 1 nM, about 1.5 nM, about 2 nM, about 2.5 nM, about 3 nM or about 3.5 nM, or any combination of any of these numbers.

The purified, active highly phosphorylated recombinant human GALNS consists of a major band of about 55-60 kDa (i.e., precursor human GALNS being at least about 75%, or at least about 80%, preferably at least about 85%, more preferably at least about 90%, and even more preferably at least about 95%, at least about 97%, at least about 98%, at least about 98.5%, at least about 99% or at least about 99.5% of the visible proteins) and minor bands at ~39 kDa and ~19 kDa (i.e., mature or processed human GALNS being less than about 25%, or less than about 20%, preferably less than about 15%, more preferably less than about 10%, and even more preferably less than about 5%, less than about 3%, less than about 2%, less than about 1.5%, less than about 1% or less than about 0.5% of the visible proteins) when subjected to SDS-PAGE under reducing conditions, or as determined by SDS-CGE. In a more particularly preferred embodiment, the purified, active highly phosphorylated recombinant human GALNS consists essentially of a single band of about 55-60 kDa (i.e., precursor human GALNS) when subjected to SDS-PAGE under reducing conditions, or as determined by SDS-CGE.

In some embodiments, the subject is suffering from MPS IVa or Morquio A syndrome. In some embodiments, the subject is suffering from MSD.

Corresponding use of active highly phosphorylated lysosomal sulfatase enzymes of the invention, which are preferably produced by methods of the invention, in preparation of a medicament for the treatment of the lysosomal storage diseases described above is also contemplated.

In a seventh aspect, the present invention provides pharmaceutical compositions comprising an active highly phosphorylated recombinant human lysosomal sulfatase enzyme as described hereinabove which is useful for treating diseases caused all or in part by, or are associated with, the deficiency in such lysosomal sulfatase enzyme, and one or more pharmaceutically acceptable carriers, diluents or excipients. In a preferred embodiment, the pharmaceutical composition comprises an active highly phosphorylated recombinant human N-acetylgalactosamine-6-sulfatase (GALNS) or biologically active fragment, mutant, variant or derivative thereof produced by the methods of the invention and one or more pharmaceutically acceptable carriers, diluents or excipients. Such pharmaceutical compositions may be suitable for administration by several routes such as intrathecal, parenteral, topical, intranasal, inhalational or oral administration. In a preferred embodiment, the pharmaceutical compositions are suitable for parenteral administration. Within the scope of this aspect are embodiments featuring nucleic acid sequences encoding the full-length lysosomal sulfatase enzymes or fragments, mutants, variants or derivatives thereof, which may be administered in vivo into cells affected with a lysosomal enzyme deficiency.

In a more preferred embodiment, the pharmaceutical composition comprises an active highly phosphorylated recombinant human N-acetylgalactosamine-6-sulfatase (GALNS) or biologically active fragment, mutant, variant or derivative thereof produced by the methods of the invention and one or more pharmaceutically acceptable carriers, diluents or excipients in a formulation comprising one or more buffering agents, and one or more stabilizers. In certain embodiments, the composition comprises an amount of phosphate buffer effective to reduce dephosphorylation of said GALNS enzyme; and a stabilizing amount of one or more stabilizers selected from the group consisting of amino acid salts, amino acid buffers, surfactants and polyols; wherein said formulation is at a pH of about 5.0-5.8.

In some embodiments, the GALNS enzyme comprises an amino acid sequence at least 95% identical to amino acids 27 to 522 of SEQ ID NO:4, and has: (i) a purity of at least about 95% as determined by COOMASSIE® Blue staining when subjected to SDS-PAGE under non-reducing conditions, (ii) at least about 80% conversion of the cysteine residue at position 53 to $C_\alpha$-formylglycine (FGly), and (iii) optionally, between 0.5 to 0.8 bis-phosphorylated oligomannose chains per monomeric protein chain, wherein at least 70% of said GALNS enzyme is in the precursor form as determined by COOMASSIE® Blue staining when subjected to SDS-PAGE under reducing conditions. In some embodiments, the GALNS enzyme is at least 95% pure as determined by RP-HPLC. In some embodiments, at least 80%, at least 85%, at least 90%, at least 95%, at least 97%, at least 98%, at least 98.5%, at least 99% or at least 99.5% of the GALNS enzyme is in the precursor form as determined by COOMASSIE® Blue staining when subjected to SDS-PAGE under reducing conditions. In some embodiments, at least 80%, at least 85%, at least 90%, at least 95%, at least 97%, at least 98%, at least 98.5%, at least 99% or at least 99.5% of the GALNS enzyme is in the precursor form as determined by SDS-capillary gel electrophoresis. In some embodiments, the GALNS enzyme has at least about 90% conversion of the cysteine residue at position 53 to $C_\alpha$-formylglycine (FGly). In some embodiments, between 50% to 80% of the GALNS enzyme binds to a mannose-6-phosphate receptor column. In some embodiments, the GALNS enzyme exhibits a specific uptake (Kuptake) into fibroblasts that is about 1 to 5 nM. In some embodiments, the GALNS enzyme exhibits a specific uptake (Kuptake) into fibroblasts that is about 1 to 3.5 nM.

The concentration of GALNS or biologically active fragment, mutant, variant or derivative thereof in the formulation is from about 0.1 to 10 mg/mL, preferably from about 0.5 to 5 mg/mL and more preferably from about 0.5 to 1.5 mg/mL.

In certain embodiments, formulation comprises an amount of phosphate buffer effective to reduce dephosphorylation of said GALNS enzyme. In related embodiments, the phosphate buffer is $NaH_2PO_4$ or its equivalent. In a further embodiment, the formulation further comprises a second buffer. In one embodiment the second buffer is an acetate buffer. In another embodiment, the acetate buffer is NaOAc/HOAc or its equivalent. Exemplary buffers are described in greater detail in the Detailed Description.

It is contemplated that the concentration of NaOAc/HOAc or its equivalent in the formulation is from about 5 to 100 mM, preferably from about 5 to 50 mM, and more preferably from about 10 to 30 mM. In a related embodiment, the concentration of $NaH_2PO_4$ or its equivalent in the formulation is from about 5 to 100 mM, preferably from about 25 to 100 mM, and more preferably from about 25 to 75 mM. In certain embodiments, the pH of the formulation is about pH 4.5-6.5, preferably about pH 5.0-6.0, and more preferably about pH 5.0-5.8.

In still another embodiment, the formulation comprises a stabilizing amount of one or more stabilizers selected from the group consisting of amino acid salts, amino acid buffers, surfactants and polyols. In one embodiment, the stabilizer is an arginine or histidine salt or buffer, optionally arginine hydrochloride. In a related embodiment, the stabilizer is a polysorbate, optionally polysorbate 20. In a further embodiment, the stabilizer is a trihydric or higher sugar alcohol, optionally sorbitol. Exemplary stabilizers are described in greater detail in the Detailed Description.

In certain embodiments, the stabilizers are selected from Arginine HCl or its equivalent, TWEEN®-20 (Polysorbate 20) or its equivalent, and sorbitol or its equivalent. In some embodiments, the concentration of Arginine HCl or its equivalent in the formulation is from about 5 to 200 mM, preferably from about 10 to 100 mM, and more preferably from about 10 to 50 mM. In another embodiment, the concentration of TWEEN®-20 or its equivalent in the formulation is from about 0.001 to 1.0% (w/v), preferably from about 0.005 to 0.2% (w/v), and more preferably from about 0.005 to 0.015% (w/v). In a related embodiment, the concentration of sorbitol or its equivalent in the formulation is from about 0.1 to 10% (w/v), preferably from about 0.5 to 5% (w/v), and more preferably from about 1.0 to 3.0% (w/v). In one embodiment, the formulation comprises an arginine salt or buffer, a polysorbate, and a polyol.

The invention further provides a method of preventing dephosphorylation of a recombinant human GALNS enzyme comprising mixing GALNS enzyme and a phosphate buffer, to a final concentration of phosphate buffer that is between about 25 mM and 75 mM. In exemplary embodiments, the amount of dephosphorylation is reduced compared to a formulation of the same enzyme in 1 mM phosphate buffer, e.g. when tested after 1 week, 2 weeks, 3 weeks, 1 month, 2 months, 3 months, 4 months, 5 months or 6 months of storage at room temperature (e.g. 25 ° C.).

In a particularly preferred embodiment, the pharmaceutical composition comprises an active highly phosphorylated recombinant human N-acetylgalactosamine-6-sulfatase (GALNS) or biologically active fragment, mutant, variant or derivative thereof produced by the methods of the invention and one or more pharmaceutically acceptable carriers, diluents or excipients in a formulation comprising NaOAc/HOAc and $NaH_2PO_4$ as buffering agents, and Arginine HCl, TWEEN®-20 (Polysorbate 20) and Sorbitol as stabilizers. The concentration of GALNS in the formulation is about 1.0+/−0.5 mg/mL. The concentration of NaOAc/HOAc in the formulation is about 20+/−10 mM, and the concentration of $NaH_2PO_4$ in the formulation is about 50+/−25 mM. The pH of the formulation is pH 5.4+/−0.4. The concentration of Arginine HCl in the formulation is about 30+/−20 mM. The concentration of TWEEN®-20 in the formulation is about 0.01+/−0.005% (w/v). The concentration of sorbitol in the formulation is about 2.0+/−1.0% (w/v).

In another aspect, the invention provides a method for detecting activity of a lysosomal sulfatase enzyme comprising (a) culturing chondrocyte cells from a patient suffering from lysosomal sulfatase enzyme deficiency, e.g., a patient suffering from Morquio syndrome, under conditions that promote maintenance of chondrocyte differentiation; (b) contacting the chondrocytes with a lysosomal sulfatase enzyme that degrades keratan sulfate; and (c) detecting levels of keratan sulfate in the cells, wherein a reduced keratan sulfate level in cells contacted with the lysosomal sulfatase enzyme compared to cells not contacted with the lysosomal sulfatase enzyme is indicative of lysosomal sulfatase enzyme activity. In some embodiments, the lysosomal sulfatase enzyme is N-acetylgalactosamine-6-sulfatase (GALNS). In some embodiments, the culturing is carried out in media comprising insulin growth factor 1 (IGF1), transforming growth factor beta (TGF-β), transferrin, insulin and ascorbic acid. In some embodiments, the keratan sulfate is detected by confocal microscopy, or via binding to anti-keratan sulfate antibody. The method may be carried out with any lysosomal sulfatase enzyme, including naturally occurring or recombinant human enzyme, or fragments or variants thereof, including variants comprising an amino acid sequence at least 80%, 85%, 90%, 95% or 100% identical to the precursor human enzyme, without signal sequence, or the mature form thereof.

In yet another aspect, the invention provides a cell-based assay for measuring the activity of a recombinant human lysosomal enzyme to degrade natural substrates. The method comprises (a) culturing an isolated human cell deficient in the lysosomal enzyme under conditions in which natural substrates for the lysosomal enzyme accumulate; (b) contacting the cell with the lysosomal enzyme; (c) lysing the cell; (d) adding to the cell lysate an enzyme that (i) is specific for the natural substrates, and (ii) cleaves small oligosaccharides from the natural substrates; (e) labeling the small oligosaccharides with a detectable moiety; (f) optionally separating the labeled small oligosaccharides; (g) detecting the labeled small oligosaccharides; and (h) determining the activity of the lysosomal enzyme to degrade the natural substrates by comparing (i) the amount of labeled small oligosaccharide from cells contacted with the lysosomal enzyme with (ii) the amount of labeled small oligosaccharides from cells not contacted with the lysosomal enzyme, wherein a reduction in (h)(i) as compared to (h)(ii) indicates the activity of the lysosomal enzyme to degrade natural substrates. In one embodiment, the small oligosaccharide is a mono-, di, or tri-saccharide. In a related embodiment, the small oligosaccharide is a disaccharide. In some embodiments, the lysosomal enzyme is selected from the group consisting of arylsulfatase B (ARSB), iduronate-2-sulfatase (IDS), sulfamidase/heparin-N-sulfatase (SGSH), N-acetylglucosamine-sulfatase (G6S) and N-acetylgalactosamine-6-sulfatase (GALNS). In some embodiments, the lysosomal enzyme is α-L-iduronidase (IDU). In some embodiments, the lysosomal enzyme is acid α-glucosidase (GAA). In some embodiments, the lysosomal enzyme is β-glucoronidase (GUSB). In some embodiments, the lysosomal enzyme is β-galactosidase (GLB1).

Suitable human cells that can be used in the cell-based assay include any human cell that is deficient in the lysosomal enzyme to be tested, such that can accumulate the natural substrates for the lysosomal enzyme. For example, cells naturally exhibiting a full (100%) or partial deficiency in activity, e.g., 30%, 50%, 70%, 80%, 90%, 95% reduction or more in activity, may be used. Cells expressing a mutant enzyme with diminished activity, or cells derived from patients suffering from a lysosomal storage disease, e.g. a mucopolysaccharidosis, may be used. Cells recombinantly altered to knockout or reduce lysosomal enzyme activity, e.g. through introducing a mutation to the encoding gene or its promoter or other regulatory region, may be used. Cells treated to reduce lysosomal enzyme activity, e.g. treated with antisense or RNAi to reduce enzyme expression, may be used.

Suitable enzymes that cleave (digest) small oligosaccharides from carbohydrates and that are "specific for" (i.e. predominantly digest) the natural substrates of the lysosomal enzyme may be selected by those of ordinary skill in the art. For example, for detection of activity of GALNS or GLB1 (enzymes that degrades keratan sulfate) the enzyme of step (d) may be Keratanase II or any enzyme that acts primarily on keratan sulfate. As another example, for detection of IDU, ARSB, IDS or GUSB (enzymes that degrade dermatan sulfate), the enzyme of step (d) may be Chondroitinase ABC or any enzyme that acts primarily on dermatan sulfate. As another example, for detection of IDU, IDS, SGHS, G6S or GUSB (enzymes that degrade heparan sulfate), the enzyme of step (d) may be Heparanase I or Heparanase II, or both. As yet another example, for detection of GAA (an enzyme that degrades glycogen), the enzyme of step (d) may be α-amylase or any enzyme that acts primarily on glycogen.

This cell-based method is capable of great sensitivity in detecting lysosomal enzyme activity. In some embodiments, the lysosomal enzyme activity is detectable when the concentration of lysosomal enzyme is as low as about 10 nM, or about 5 nM, or about 1 nM, or about 0.75 nM, or about 0.5 nM, or about 0.25 nM, or about 0.1 nM, or about 0.05 nM, or about 0.01 nM, or about 0.005 nM, or about 1 pM, or about 0.5 pM.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

FIG. 1 describes the nucleotide sequence of human sulfatase modifying factor 1 (SUMF1) (SEQ ID NO: 1).

FIG. 2 describes the amino acid sequence of human sulfatase modifying factor 1 (SUMF1) (SEQ ID NO: 2).

FIG. 3 describes the nucleotide sequence of human N-acetylgalactosamine-6-sulfatase (GALNS) (SEQ ID NO: 3).

FIG. 4 describes the amino acid sequence of human N-acetylgalactosamine-6-sulfatase (GALNS) (SEQ ID NO: 4). The signal peptide of 26 amino acids at the N-terminus is absent in processed GALNS.

FIG. 5 depicts the structure and characteristics of processed human N-acetylgalactosamine-6-sulfatase (GALNS) (SEQ ID NO: 5).

FIG. 6A shows a G71S clone screen for active GALNS in 96-wells. FIG. 6B shows G71S clone GALNS productivity in picograms per cell per day.

FIG. 9A shows the purification of human N-acetylgalactosamine-6-sulfatase (GALNS) by Blue SEPHAROSE® 6 Fast Flow chromatography while FIG. 9B shows the purification by FRACTOGEL® SE Hi-CAP chromatography following Blue SEPHAROSE® 6 Fast Flow chromatography. Purity is determined by COOMASSIE® Blue staining of SDS-PAGE (left) and by Western blotting using an anti-GALNS (IVA) antibody (right).

FIG. 18 shows the glycosylation profile of purified human N-acetylgalactosamine-6-sulfatase (GALNS) enzyme upon storage for 2 months at 5° C., at 25° C. or at 40° C. as indicated in a formulation comprising 15 mM Arginine HCl, 30 mM Arginine HCl, 15 mM NaCl or 30 mM NaCl, at pH 5.0, pH 5.4 or pH 5.8, as indicated. Percent bis-phosphorylated mannose 7 (BPM7) was measured by capillary electrophoresis (CE) after digestion of the GALNS enzyme with PNGase F to cleave the asparagine N-linked oligosaccharides. Reference indicates the percent BPM7 for a reference lot of GALNS stored for 2 months at 5° C., at 25° C. or at 40° C. as indicated in a formulation comprising 100 mM phosphate buffer.

DETAILED DESCRIPTION OF THE INVENTION

Figure 6:
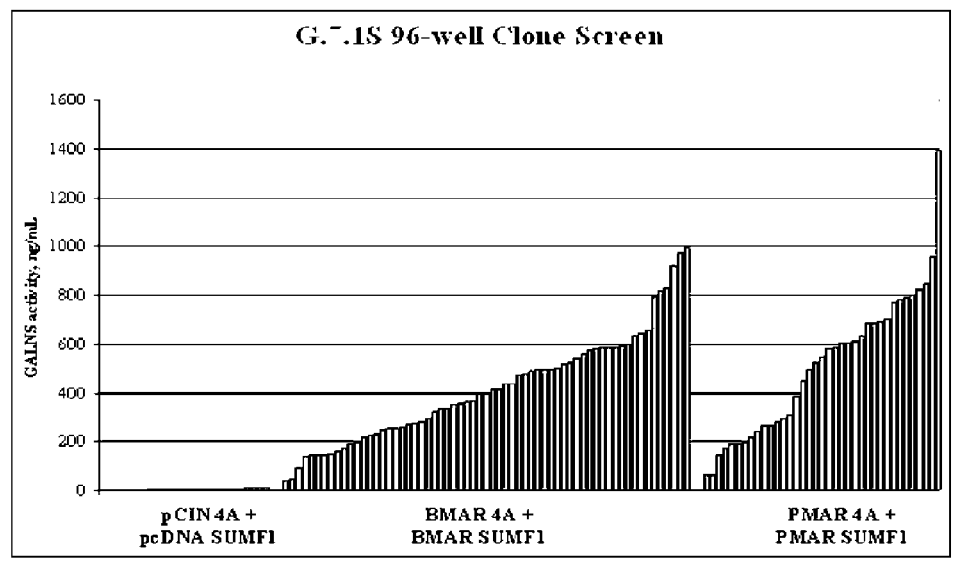
FIG. 6A and FIG. 6B show the expression of human N-acetylgalactosamine-6-sulfatase (GALNS) from G71S cells co-transfected with human sulfatase modifying factor 1 (SUMF1) and human GALNS expression vectors.
Figure 6:
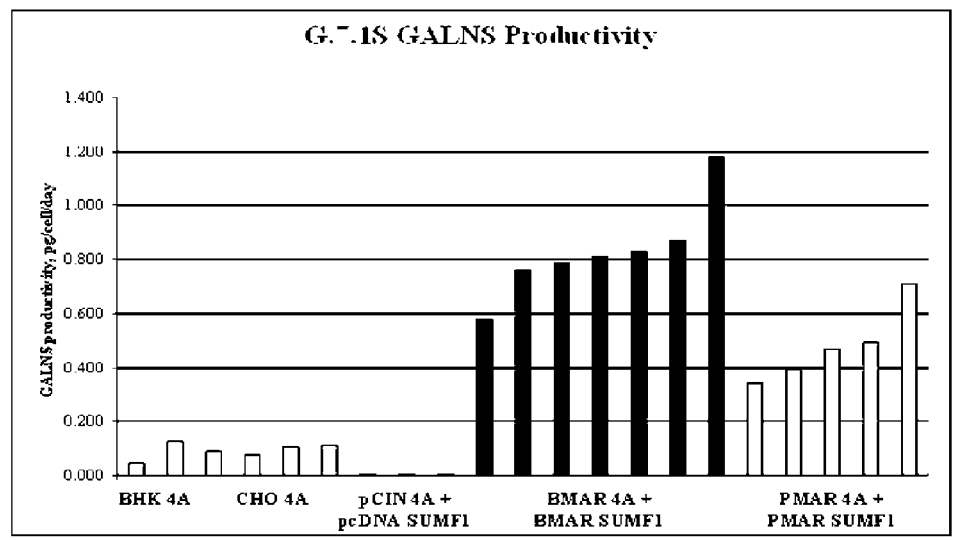

The present invention relates to the discovery of a method that reconciles the need for large-scale manufacture of recombinant lysosomal sulfatase enzymes with the requirement of an active highly phosphorylated lysosomal sulfatase enzyme product that is efficient in targeting lysosomes and hence is therapeutically effective.

The therapeutic effectiveness of a lysosomal enzyme preparation depends on the level of mannose-6-phosphate in that preparation. Phosphate is added to the target glycoprotein by a post-translational modification in the endoplasmic reticulum and early Golgi. Folded lysosomal enzymes display a unique tertiary determinant that is recognized by an oligosaccharide modification enzyme. The determinant is composed of a set of specifically spaced lysines and is found on most lysosomal enzymes despite absence of primary sequence homology. The modification enzyme, UDP-GlcNAc phosphotransferase, binds to the protein determinant and adds GlcNAc-1-phosphate to the 6-position of terminal mannose residues on oligosaccharides proximate to the binding site; a second enzyme, phosphodiester α-GlcNAcase, then cleaves the GlcNAc-phosphate bond to give a mannose-6-phosphate terminal oligosaccharide (Canfield et al., U.S. Pat. No. 6,537,785). The purpose of the mannose-6-phosphate modification is to divert lysosomal enzymes from the secretory pathway to the lysosomal pathway within the cell. Mannose-6-phosphate-bearing enzyme is bound by the MPR in the trans Golgi and routed to the lysosome instead of the cell surface.

In addition to the presence of the mannose-6-phosphate marker on lysosomal enzyme oligosaccharides, lysosomal routing of enzymes depends on the acidification of trafficking endosomes emerging from the end of the trans Golgi stack. Chemical quenching of the acidic environment within these endosomes with diffusible basic molecules results in disgorgement of the vesicular contents, including lysosomal enzymes, into the extracellular milieu (Braulke et al., *Eur. J. Cell Biol.* 43(3): 316-321, 1987). Acidification requires a specific vacuolar ATPase embedded within the membrane of the endosome (Nishi et al., *Nat. Rev. Mol. Cell Biol.* 3(2): 94-103, 2002). Failure of this ATPase is expected to enhance the secretion of lysosomal enzymes at the expense of lysosomal routing. Manufacturing cell lines that carry defects in the vacuolar ATPase would be expected to prevent non-productive diversion of phosphorylated recombinant enzyme to the intracellular lysosomal compartment.

In 1984, Chinese hamster ovary (CHO) cell mutants specifically defective in endosomal acidification were generated and characterized (Park et al., *Somat. Cell Mol. Genet.* 17(2): 137-150, 1991). CHO-K1 cells were chemically mutagenized and selected for survival at elevated temperatures in the presence of toxins. These toxins required endosomal acidification for the full expression of their lethality (Marnell et al., *J. Cell. Biol.* 99(6): 1907-1916, 1984). In the former study, a cocktail of two toxins with different mechanisms of action was chosen to avoid selection of toxin-specific resistance. The principle is that while the probability of serendipitous mutations that result in resistance to one particular toxin is small, the probability of two simultaneous serendipitous mutations specific for two entirely different toxins is non-existent. Selections were carried out at elevated temperature to allow for temperature-sensitive mutations. This genetic screen resulted in two mutants, one of which was designated G.7.1 (G71), that were resistant to toxins at elevated temperatures. The lesion in G71 was not due to the uptake or mechanism of action of the two toxins, but resulted from an inability of the clone to acidify endosomes at elevated temperatures. This inability was also evident at permissive temperatures (34° C.), although to a lesser extent. G71 cells were also found to be auxotrophic for iron at elevated temperatures, despite normal uptake of transferrin from the medium (Timchak et al., *J. Biol. Chem.* 261(30): 14154-14159, 1986). Since iron was released from transferrin only at low pH, auxotrophy for iron despite normal transferrin uptake indicated a failure in endosomal acidification. Another study demonstrated that the acidification defect was manifested primarily in endosomes rather than lysosomes (Stone et al., *J. Biol. Chem.* 262(20): 9883-9886, 1987). The data on G71 were consistent with the conclusion that a mutation resulted in the destabilization of the vacuolar ATPase responsible for endosomal acidification. Destabilization was most evident at elevated temperatures (39.5° C.) but was partially expressed even at lower temperatures (34° C.). A study of the trafficking of two endogenous lysosomal enzymes, cathepsin D and alpha-glucosidase, in G71 cells (Park et al., *Somat. Cell Mol. Genet.* 17(2):137-150, 1991) showed that both enzymes were quantitatively secreted at elevated temperatures, and glycosylation of the enzymes was unaffected. The secretion of phosphorylated acid alpha-glucosidase was significantly enhanced at non-permissive temperatures.

The therapeutic effectiveness of a lysosomal sulfatase enzyme preparation not only depends on the level of mannose-6-phosphate, but also depends on the presence of active enzyme in that preparation. All known sulfatases contain a cysteine residue at their catalytic site; this cysteine residue is post-translationally modified to $C_\alpha$-formylglycine (FGly) to activate the enzyme. This cysteine to FGly post-translational enzyme activation, which is catalyzed by sulfatase modifying factor 1 (SUMF1), occurs within the endoplasmic reticulum on unfolded sulfatases immediately after translation, prior to targeting of the sulfatases to the lysosome (Dierks et al., *Proc. Natl. Acad. Sci. USA* 94:11963-11968, 1997). The importance of this unique post-translational modification is highlighted by the fact that mutations in SUMF1, which result in impaired FGly formation in lysosomal sulfatase enzymes, cause Multiple Sulfatase Deficiency (MSD) in man (Diez-Ruiz et al., *Annu. Rev. Genomics Hum. Genet.* 6:355-379, 2005).

Thus, the ability of G71 cells, mutant CHO cells that are defective in endosomal acidification, to co-express recombinant human sulfatase modifying enzyme (SUMF1) and a human lysosomal sulfatase enzyme provides a mechanism for the large-scale production of active highly phosphorylated recombinant human lysosomal sulfatase enzymes useful for the management of lysosomal storage disorders caused by or associated with a deficiency of such lysosomal sulfatase enzymes.

I. Definitions

Unless otherwise defined, all technical and scientific terms used herein have the same meaning as commonly understood by one of ordinary skill in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

"Allelic variant" refers to any of two or more polymorphic forms of a gene occupying the same genetic locus. Allelic variations arise naturally through mutation, and may result in phenotypic polymorphism within populations. Gene mutations can be silent (i.e., no change in the encoded polypeptide) or may encode polypeptides having altered amino acid sequences. "Allelic variants" also refer to cDNAs derived from mRNA transcripts of genetic allelic variants, as well as the proteins encoded by them.

"Amplification" refers to any means by which a polynucleotide sequence is copied and thus expanded into a larger number of polynucleotide molecules, e.g., by reverse transcription, polymerase chain reaction, and ligase chain reaction.

A first sequence is an "antisense sequence" with respect to a second sequence if a polynucleotide whose sequence is the first sequence specifically hybridizes with a polynucleotide whose sequence is the second sequence.

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'. A nucleotide sequence is "substantially complementary" to a reference nucleotide sequence if the sequence complementary to the subject nucleotide sequence is substantially identical to the reference nucleotide sequence.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);

3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "fragment" when used in reference to polypeptides refers to polypeptides that are shorter than the full-length polypeptide by virtue of truncation at either the N-terminus or C-terminus of the protein or both, and/or by deletion of an internal portion or region of the protein. Fragments of a polypeptide can be generated by methods known in the art.

The term "mutant" when used in reference to polypeptides refers to polypeptides in which one or more amino acids of the protein have been substituted by a different amino acid. The amino acid substitution can be a conservative substitution, as defined above, or can be a non-conservative substitution. Mutant polypeptides can be generated by methods known in the art.

The term "derivative" when used in reference to polypeptides refers to polypeptides chemically modified by such techniques, for example and not for limitation, as ubiquitination, labeling (e.g., with radionuclides or various enzymes), covalent polymer attachment such as pegylation (i.e., derivatization with polyethylene glycol) and insertion or substitution by chemical synthesis of amino acids such as ornithine, which do not normally occur in human proteins. Derivative polypeptides can be generated by methods known in the art.

The term "derivative" when used in reference to cell lines refers to cell lines that are descendants of the parent cell line; for example, this term includes cells that have been passaged or subcloned from parent cells and retain the desired property, descendants of the parent cell line that have been mutated and selected for retention of the desired property, and descendants of the parent cell line which have been altered to contain different expression vectors or different exogenously added nucleic acids.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., Fahrlander et al., *Bio/Technology* 6:1165, 1988). Quantitation of the signal is achieved by, e.g., scintillation counting, densitometry, or flow cytometry.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Equivalent dose" refers to a dose, which contains the same amount of active agent.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Highly phosphorylated," "high level of phosphorylation" and "high level of phosphorylated oligosaccharides"

refer to preparations of lysosomal sulfatase enzymes in which at least 50% of the lysosomal sulfatase enzyme binds to the cation-independent mannose-6-phosphate receptor through phosphorylated oligosaccharides. Binding is further characterized by sensitivity to competition with mannose-6-phosphate. A highly phosphorylated lysosomal sulfatase enzyme may also refer to a lysosomal sulfatase enzyme with at least 0.25, preferably at least 0.5, and more preferably at least 0.75 bis-phosphorylated oligomannose chains per protein chain. Alternatively, a highly phosphorylated lysosomal sulfatase enzyme (GALNS) may refer to an enzyme in which the specific uptake, Kuptake (the concentration of enzyme/ligand that yields half of the maximal uptake value), in fibroblasts is about 0.1 to 10 nM, or about 0.1 to 7 nM, or about 0.5 to 5 nM, or about 1 to 5 nM, or about 1 to 3.5 nM, about 1 nM, about 1.5 nM, about 2 nM, about 2.5 nM, about 3 nM or about 3.5 nM, or any combination of any of these numbers.

"Bis-phosphorylated oligomannose chains" as used herein refers to mannose-containing oligosaccharide chains that are N-linked to asparagine residues in lysosomal sulfatase enzymes and comprise two mannose-6-phosphate residues. Typically, the bis-phosphorylated oligomannose chains have 7 mannose residues, i.e., bis-phosphate mannose 7 (BPM7), which are linked to two GlcNAc residues, which in turn are linked to the asparagine residue in the lysosomal sulfatase enzyme.

"Active," "activated" and "high level of activation" refer to preparations of lysosomal sulfatase enzymes in which at least 50%, 55%, 60%, 65% preferably at least 70%, 75%, 80%, 85%, 90%, or 95% of the protein's active site cysteine residue has been post-translationally modified to $C_\alpha$-formylglycine (FGly). Alternatively, "active," "activated" and "high level of activation" refer to preparations of lysosomal sulfatase enzymes which exhibit a specific activity that is at least about 30% (e.g., 35%, 40%, 45%, 50%, 55%, 60%, 65%, 70%, 75%, 80%, 85%, 90%, 95%, 2-fold, 2.5-fold, 3-fold, 4-fold, 5-fold, 10-fold, 15-fold, 20-fold, 30-fold, 40-fold or 50-fold) greater than the specific activity of a control lysosomal sulfatase enzyme of the same amino acid sequence that has been produced in host cells (e.g., CHO cells or CHO-derived cells) that do not express recombinant human SUMF1. A suitable control preparation of lysosomal sulfatase enzyme preferably has the same amino acid sequence as the highly active preparation, and is expressed by the same gene using the same promoter or regulatory sequence(s) in the same host cell, except that the host cell does not express recombinant human SUMF1, is produced under the same or similar culturing conditions including for the same time period of culture, and optionally is purified to the same or similar extent as the highly active preparation.

"Active highly phosphorylated" refers to refers to preparations of lysosomal sulfatase enzymes in which at least 50%, preferably at least 70%, more preferably at least 90%, and even more preferably at least 95% of the protein's active site cysteine residue has been post-translationally modified to $C_\alpha$-formylglycine (FGly) and with at least 0.25, preferably at least 0.5, and more preferably at least 0.75 bis-phosphorylated oligomannose chains per protein chain.

The term "biologically active" refers to polypeptide (i.e., enzyme) fragments, mutants, variants or derivatives thereof that retain at least a substantial amount (e.g., at least about 50%, preferably at least about 70%, and more preferably at least about 90%) of one or more biological activities of the full-length polypeptide. When used in reference to a lysosomal sulfatase enzyme, a biologically active fragment, mutant, variant or derivative thereof retains at least a substantial amount of sulfatase activity (i.e., cleavage of sulfate esters from its target substrates). When used in reference to sulfatase modifying factor 1 (SUMF1), a biologically active fragment, mutant, variant or derivative thereof retains at least a substantial amount of formylglycine-generating activity (i.e., modification of a lysosomal sulfatase enzyme's active site cysteine residue to $C_\alpha$-formylglycine (FGly)).

The term "purity" or "pure" when used in reference to polypeptides refers to the amount of the polypeptide being analyzed in comparison to any contaminating substances that can be detected using a particular method. For the recombinant lysosomal sulfatase enzymes of the invention, "purity" may be determined by subjecting the sulfatase enzyme preparation to electrophoretic separation by SDS-PAGE under reducing or non-reducing conditions followed by staining with COOMASSIE® Blue or silver, or by chromatographic separation by HPLC (e.g., C4 reverse phase (RP), C3 RP) or by any other chromatographic separation, e.g., size exclusion (SEC) and the like. Using any one of these methods, the purified recombinant lysosomal sulfatase enzymes of the invention have a purity of at least about 80%, or at least about 85%, preferably at least about 90%, more preferably at least about 95%, and even more preferably at least about 97%, 98% or 99%.

The term "precursor" or "precursor form" refers to the form of recombinant lysosomal sulfatase enzyme that is secreted from a mammalian cell, i.e., lacking the signal sequence, but lacking certain modifications, e.g., internal cleavage of the proteins, which normally occur in the lysosome. The term "mature," "mature form," "processed" or "processed form" refers to the form of recombinant lysosomal sulfatase enzyme that normally exists in the lysosome. For the recombinant lysosomal sulfatase enzymes of the invention, the relative abundance of "precursor" or "precursor form" and "mature," "mature form," "processed" or "processed form" may be determined by subjecting the sulfatase enzyme preparation to electrophoretic separation by SDS-PAGE under reducing conditions followed by staining with COOMASSIE® Blue or silver, or by chromatographic separation by HPLC (e.g., C4reverse phase (RP), C3RP) or by any other chromatographic separation, e.g., size exclucion (SEC) and the like, or a combination of electrophoretic separation and chromatographic separation, e.g., SDS-PAGE followed by capillary gel electrophoresis (SDS-CGE). Using these methods, the purified recombinant lysosomal sulfatase enzymes of the invention consist of at least about 65%, 70%, or 75%, preferably at least about 80% or 85%, more preferably at least about 90%, and even more preferably at least about 95%, 97%, 98%, 98.5%, 99% or 99.5% "precursor" or "precursor form." Alternatively, using these methods, the purified recombinant lysosomal sulfatase enzymes of the invention consist of less than about 35%, 30% or 25%, preferably less than about 20% or 15%, more preferably less than about 10%, and even more preferably less than about 5%, 3%, 2%, 1.5%, 1% or 0.5% "mature," "mature form," "processed" or "processed form." In some embodiments, only the "precursor" or "precursor form" is detected (i.e., the sulfatase enzyme preparation consists essentially of a single detectable band when subjected to SDS-PAGE under reducing conditions, or as determined by SDS-CGE, or a single peak when analyzed by HPLC.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Low level of phosphorylation" or "low phosphorylation" refers to a preparation of lysosomal sulfatase enzymes in which the uptake into fibroblast cells has a half maximal concentration of greater than 10 nM or the fraction of lysosomal sulfatase enzymes that binds a mannose-6-phosphate receptor column is less than about 25%.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Pharmaceutical composition" refers to a composition suitable for pharmaceutical use in a subject animal, including humans and mammals. A pharmaceutical composition comprises a pharmacologically effective amount of a therapeutic lysosomal sulfatase enzyme and also comprises one or more pharmaceutically acceptable carriers, diluents or excipients. A pharmaceutical composition encompasses a composition comprising the active ingredient(s), and the inert ingredient(s) that make up the carrier, diluent or excipient, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a lysosomal sulfatase enzyme of the present invention and one or more pharmaceutically acceptable carriers, diluents or excipients.

"Pharmaceutically acceptable carrier, diluent or excipient" refers to any of the standard pharmaceutical carriers, diluents, buffers, and excipients, such as, for example and not for limitation, a phosphate buffered saline solution, 5% aqueous solution of dextrose, and emulsions, such as an oil/water or water/oil emulsion, and various types of wetting agents and/or adjuvants. Suitable pharmaceutical carriers, diluents or excipients and formulations are described in Remington's Pharmaceutical Sciences, 19th Ed. (Mack Publishing Co., Easton, 1995). Preferred pharmaceutical carriers, diluents or excipients depend upon the intended mode of administration of the active agent. Typical modes of administration include, for example and not for limitation, enteral (e.g., oral) or parenteral (e.g., subcutaneous, intramuscular, intravenous or intraperitoneal) injection; or topical, transdermal, or transmucosal administration.

A "pharmaceutically acceptable salt" is a salt that can be formulated into a lysosomal sulfatase enzyme for pharmaceutical use including, e.g., metal salts (sodium, potassium, magnesium, calcium, etc.) and salts of ammonia or organic amines.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Hybridizing specifically to," "specific hybridization," or "selectively hybridize to" refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

A "subject" of diagnosis or treatment is a human or non-human animal, including a mammal or a primate.

The phrase "substantially homologous" or "substantially identical" in the context of two nucleic acids or polypeptides, generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360, 1987. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (Thompson et al., *Nucleic Acids Research* 22: 4673-4680, 1994).

Another example of algorithm that is suitable for determining percent sequence identity and sequence similarity is the BLAST algorithm, which is described in Altschul et al., *J. Mol. Biol.* 215:403-410, 1990. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., *J. Mol. Biol.* 215:403-410, 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915, 1989).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the lysosomal sulfatase enzymes of the invention are substantially pure or isolated. In some embodiments, the lysosomal sulfatase enzymes of the invention are substantially pure or isolated with respect to the macromolecular starting materials used in their synthesis. In some embodiments, the pharmaceutical composition of the invention comprises a substantially purified or isolated therapeutic lysosomal sulfatase enzyme admixed with one or more pharmaceutically acceptable carriers, diluents or excipients.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The lysosomal sulfatase enzymes of the invention may be given as a therapeutic treatment or for diagnosis.

"Therapeutic index" refers to the dose range (amount and/or timing) above the minimum therapeutic amount and below an unacceptably toxic amount.

"Treatment" refers to prophylactic treatment or therapeutic treatment or diagnostic treatment.

The term "unit dosage form," as used herein, refers to physically discrete units suitable as unitary dosages for human and animal subjects, each unit containing a predetermined quantity of lysosomal sulfatase enzyme of the present invention calculated in an amount sufficient to produce the desired effect in association with one or more pharmaceutically acceptable carriers, diluents or excipients. The specifications for the novel unit dosage forms of the present invention depend on the particular lysosomal sulfatase enzyme employed and the effect to be achieved, and the pharmacodynamics associated with each lysosomal sulfatase enzyme in the host.

II. Production of Lysosomal Sulfatase Enzymes

In one aspect, the present invention features a novel method of producing active highly phosphorylated lysosomal sulfatase enzymes in amounts that enable therapeutic use of such enzymes. In general, the method features transformation of a suitable cell line with the cDNA encoding for human sulfatase modifying factor 1 (SUMF1) or a biologically active fragment, mutant, variant or derivative thereof and a cDNA encoding full-length lysosomal sulfatase enzyme or a biologically active fragment, mutant, variant or derivative thereof. Those of skill in the art may prepare expression constructs other than those expressly described herein for optimal production of such lysosomal sulfatase enzymes in suitable transfected cell lines therewith. Moreover, skilled artisans may easily design fragments of cDNA encoding biologically active fragments, variants, mutants or derivatives of the naturally occurring SUMF1 or lysosomal sulfatase enzymes that possess the same or similar biological activity to the naturally occurring full-length enzymes.

Host Cells

Host cells used to produce recombinant lysosomal sulfatase enzymes are endosomal acidification-deficient cell lines characterized by their ability to produce such lysosomal sulfatase enzymes in amounts that enable use of the enzyme therapeutically. The invention provides a CHO-K1-derived, END3 complementation group cell line, designated G71. The invention also provides a G71 cell line that has been adapted for growth in serum-free suspension culture, designated G71S. The invention also provides derivatives of the G71 and G71S cell lines which have been subcloned further or which contain different expression plasmids.

Cells that contain and express DNA or RNA encoding a recombinant protein are referred to herein as genetically modified cells. Mammalian cells that contain and express DNA or RNA encoding the recombinant protein are referred to as genetically modified mammalian cells. Introduction of the DNA or RNA into cells is by a known transfection method, such as, for example and not for limitation, electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of production for cells, including mammalian cells, which express DNA or RNA encoding a recombinant protein are described in co-pending patent applications U.S. Ser. No. 08/334,797, entitled "In Vivo Protein Production and Delivery System for Gene Therapy", by Richard F. Selden, Douglas A. Treco and Michael W. Heartlein (filed Nov. 4, 1994); U.S. Ser. No. 08/334,455, entitled "In Vivo Production and Delivery of Erythropoietin or Insulinotropin for Gene Therapy", by Richard F. Selden, Douglas A. Treco and Michael W. Heartlein (filed Nov. 4, 1994) and U.S. Ser. No. 08/231,439, entitled "Targeted Introduction of DNA Into Primary or Secondary Cells and Their Use for Gene Therapy", by Douglas A. Treco, Michael W. Heartlein and Richard F. Selden (filed Apr. 20, 1994). The teachings of each of these applications are expressly incorporated herein by reference in their entirety.

In preferred embodiments, the host cell used to produce recombinant lysosomal sulfatase enzymes is an endosomal acidification-deficient cell line characterized by its ability to produce such lysosomal sulfatase enzymes in amounts that enable use of the enzyme therapeutically. In preferred embodiments, the invention provides a CHO-K1-derived, END3 complementation group cell line, designated G71, and a G71 cell line that has been adapted for growth in serum-free suspension culture, designated G71S, which co-express human sulfatase modifying factor 1 (SUMF1) and a recombinant lysosomal sulfatase enzyme, and are thus capable of producing high yields of active highly phosphorylated lysosomal sulfatase enzymes, as specified in "DEFINITIONS", thereby enabling the large scale production of therapeutic lysosomal sulfatase enzymes. In most preferred embodiments, the G71 or G71S cell line, or derivative thereof, expresses and secretes recombinant lysosomal sulfatase enzymes in amounts of at least about 0.5, preferably at least about 0.75, more preferably at least about 1.0, and even more preferably at least about 1.25 picograms/cell/day.

Vectors and Nucleic Acid Constructs

A nucleic acid construct used to express the recombinant protein, either human sulfatase modifying factor 1 (SUMF1) or lysosomal sulfatase enzyme or both, can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to recombinant protein-encoding sequences, sequences sufficient for expression of the protein in the cells and, optionally, for replication of the construct. It typically includes a promoter, recombinant protein-encoding DNA and a polyadenylation site. The DNA encoding the recombinant protein is positioned in the construct in such a manner that its expression is under the control of the promoter. Optionally, the construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

In those embodiments in which the DNA construct integrates into the cell's genome, it need include only the recombinant protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker, a matrix attachment region (MAR) or other element known in the art that enhances expression of the region where it is inserted, and/or DNA homologous to genomic DNA in the recipient cell, to target integration of the DNA to a selected site in the genome (to target DNA or DNA sequences).

Cell Culture Methods

Mammalian cells containing the recombinant protein-encoding DNA or RNA are cultured under conditions appropriate for growth of the cells and expression of the DNA or RNA. Those cells which express the recombinant protein can be identified, using known methods and methods described herein, and the recombinant protein can be isolated and purified, using known methods and methods also described herein, either with or without amplification of recombinant protein production. Identification can be carried out, for example, through screening genetically modified mammalian cells that display a phenotype indicative of the presence of DNA or RNA encoding the recombinant protein, such as PCR screening, screening by Southern blot analysis, or screening for the expression of the recombinant protein. Selection of cells which contain incorporated recombinant protein-encoding DNA may be accomplished by including a selectable marker in the DNA construct, with subsequent culturing of transfected or infected cells containing a selectable marker gene, under conditions appropriate for survival of only those cells that express the selectable marker gene. Further amplification of the introduced DNA construct can be effected by culturing genetically modified mammalian cells under appropriate conditions (e.g., culturing genetically modified mammalian cells containing an amplifiable marker gene in the presence of a concentration of a drug at which only cells containing multiple copies of the amplifiable marker gene can survive).

Genetically modified mammalian cells expressing the recombinant protein can be identified, as described herein, by detection of the expression product. For example, mammalian cells expressing active highly phosphorylated lysosomal sulfatase enzymes can be identified by a sandwich enzyme immunoassay. The antibodies can be directed toward the active agent portion.

Variants of Lysosomal Sulfatase Enzymes

In certain embodiments, active highly phosphorylated lysosomal sulfatase enzyme mutants or variants may be prepared and will be useful in a variety of applications in which active highly phosphorylated lysosomal sulfatase enzymes may be used. Amino acid sequence mutants or variants of the polypeptide can be substitutional, insertional or deletion mutants or variants. Deletion mutants or variants lack one or more residues of the native protein that are not essential for function or immunogenic activity. A common type of deletion mutant or variant is one lacking secretory signal sequences or signal sequences directing a protein to bind to a particular part of a cell. Insertional mutants or variants typically involve the addition of material at a non-terminal point in the polypeptide. This may include the insertion of an immunoreactive epitope or simply a single residue. Terminal additions, also called fusion proteins, are discussed below.

Variants may be substantially homologous or substantially identical to the unmodified lysosomal sulfatase enzyme as set out above. Preferred variants are those which are variants of an active highly phosphorylated lysosomal sulfatase enzyme polypeptide that retains at least some of the biological activity, e.g. sulfatase activity, of the lysosomal sulfatase enzyme. Other preferred variants include variants of a human N-acetylgalactosamine-6-sulfatase polypeptide that retain at least some of the sulfatase activity of the human N-acetylgalactosamine-6-sulfatase.

Substitutional mutants or variants typically exchange one amino acid of the wild-type polypeptide for another at one or more sites within the protein, and may be designed to modulate one or more properties of the polypeptide, such as, for example and not for limitation, stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

One aspect of the present invention contemplates generating glycosylation site mutants or variants in which the O- or N-linked glycosylation site of the lysosomal sulfatase enzyme has been mutated. Such mutants or variants will yield important information pertaining to the biological activity, physical structure and substrate binding potential of the active highly phosphorylated lysosomal sulfatase enzyme. In particular aspects, it is contemplated that other mutants or variants of the active highly phosphorylated lysosomal sulfatase enzyme polypeptide may be generated that retain the biological activity but have increased or decreased substrate binding activity. As such, mutations of the active site or catalytic region are particularly contemplated in order to generate protein mutants or variants with altered substrate binding activity. In such embodiments, the sequence of the active highly phosphorylated lysosomal sulfatase enzyme is compared to that of the other related enzymes and selected residues are specifically mutated.

Numbering the amino acids of the mature protein from the putative amino terminus as amino acid number 1, exemplary mutations that may be useful include, for example, substitution of all or some of potentially glycosylated asparagines, including positions 178 and 397 of recombinant human N-acetylgalactosamine-6-sulfatase (GALNS) (see FIG. 5).

Substrate binding can be modified by mutations at/near the active site of the lysosomal sulfatase enzyme. Taking into consideration such mutations are exemplary, those of skill in the art will recognize that other mutations of the enzyme sequence can be made to provide additional structural and functional information about this protein and its activity.

In order to construct mutants or variants such as those described above, one of skill in the art may employ well known standard technologies. Specifically contemplated are N-terminal deletions, C-terminal deletions, internal deletions, as well as random and point mutagenesis.

N-terminal and C-terminal deletions are forms of deletion mutagenesis that take advantage, for example, of the presence of a suitable single restriction site near the end of the C- or N-terminal region. The DNA is cleaved at the site and the cut ends are degraded by nucleases such as BAL31, exonuclease III, DNase I, and S1 nuclease. Rejoining the two ends produces a series of DNAs with deletions of varying size around the restriction site. Proteins expressed from such mutant can be assayed for appropriate biological function, e.g. enzymatic activity, using techniques standard in the art, and described in the specification. Similar techniques may be employed for internal deletion mutants by using two suitably placed restriction sites, thereby allowing a precisely defined deletion to be made, and the ends to be religated as above.

Also contemplated are partial digestion mutants. In such instances, one of skill in the art would employ a "frequent cutter" that cuts the DNA in numerous places depending on the length of reaction time. Thus, by varying the reaction conditions it will be possible to generate a series of mutants of varying size, which may then be screened for activity.

A random insertional mutation may also be performed by cutting the DNA sequence with a DNase I, for example, and inserting a stretch of nucleotides that encode, 3, 6, 9, 12, etc., amino acids and religating the end. Once such a mutation is made the mutants can be screened for various activities presented by the wild-type protein.

Point mutagenesis also may be employed to identify with particularity which amino acid residues are important in particular activities associated with lysosomal sulfatase enzyme biological activity. Thus, one of skill in the art will be able to generate single base changes in the DNA strand to result in an altered codon and a missense mutation.

The amino acids of a particular protein can be altered to create an equivalent, or even an improved, second-generation molecule. Such alterations contemplate substitution of a given amino acid of the protein without appreciable loss of interactive binding capacity with structures such as, for example, antigen-binding regions of antibodies or binding sites on substrate molecules or receptors. Since it is the interactive capacity and nature of a protein that defines that protein's biological functional activity, certain amino acid substitutions can be made in a protein sequence, and its underlying DNA coding sequence, and nevertheless obtain a protein with like properties. Thus, various changes can be made in the DNA sequences of genes without appreciable loss of their biological utility or activity, as discussed below.

In making such changes, the hydropathic index of amino acids may be considered. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte & Doolittle, *J. Mol. Biol.*, 157(1):105-132, 1982, incorporated herein by reference). Generally, amino acids may be substituted by other amino acids that have a similar hydropathic index or score and still result in a protein with similar biological activity, i.e., still obtain a biological functionally equivalent protein.

In addition, the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As such, an amino acid can be substituted for another having a similar hydrophilicity value and still obtain a biologically equivalent and immunologically equivalent protein.

Exemplary amino acid substitutions that may be used in this context of the invention include but are not limited to exchanging arginine and lysine; glutamate and aspartate; serine and threonine; glutamine and asparagine; and valine, leucine and isoleucine. Other such substitutions that take into account the need for retention of some or all of the biological activity whilst altering the secondary structure of the protein will be well known to those of skill in the art.

Another type of variant that is contemplated for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles described above, to engineer second generation molecules having many of the natural properties of lysosomal sulfatase enzymes, but with altered and even improved characteristics.

Modified Glycosylation of Lysosomal Sulfatase Enzymes

Variants of an active highly phosphorylated lysosomal sulfatase enzyme can also be produced that have a modified glycosylation pattern relative to the parent polypeptide, for example, deleting one or more carbohydrate moieties, and/or adding one or more glycosylation sites that are not present in the native polypeptide.

Glycosylation is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a polypeptide by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added by inserting or substituting one or more serine or threonine residues into the sequence of the original polypeptide.

Domain Switching

Various portions of lysosomal sulfatase enzyme proteins possess a great deal of sequence homology. Mutations may be identified in lysosomal sulfatase enzyme polypeptides that may alter its function. These studies are potentially important for at least two reasons. First, they provide a reasonable expectation that still other homologs, allelic variants and mutants of this gene may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule as described above. One way in which this information can be exploited is in "domain switching."

Domain switching involves the generation of recombinant molecules using different but related polypeptides. For example, by comparing the sequence of a lysosomal sulfatase enzyme, e.g. N-acetylgalactosamine-6-sulfatase, with that of a similar lysosomal sulfatase enzyme from another source and with mutants and allelic variants of these polypeptides, one can make predictions as to the functionally significant regions of these molecules. It is possible, then, to switch related domains of these molecules in an effort to determine the criticality of these regions to enzyme function and effects in lysosomal storage disorders. These molecules may have additional value in that these "chimeras" can be distinguished from natural molecules, while possibly providing the same or even enhanced function.

Based on the numerous lysosomal sulfatase enzymes now being identified, further analysis of mutations and their predicted effect on secondary structure will add to this understanding. It is contemplated that the mutants that switch domains between the lysosomal sulfatase enzymes will provide useful information about the structure/function relationships of these molecules and the polypeptides with which they interact.

Fusion Proteins

In addition to the mutations described above, the present invention further contemplates the generation of a specialized kind of insertional variant known as a fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include, but are not limited to, the glutathione S-transferase (GST) system (Pharmacia, Piscataway, N.J.), the maltose binding protein system (NEB, Beverley, Mass.), the FLAG system (IBI, New Haven, Conn.), the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

A particularly useful fusion construct may be one in which an active highly phosphorylated lysosomal sulfatase enzyme polypeptide or fragment thereof is fused to a hapten to enhance immunogenicity of a lysosomal sulfatase enzyme fusion construct. This may be useful in the production of antibodies to the active highly phosphorylated lysosomal sulfatase enzyme to enable detection of the protein. In other embodiments, a fusion construct can be made which will enhance the targeting of the lysosomal sulfatase enzyme-related compositions to a specific site or cell.

Other fusion constructs including a heterologous peptide with desired properties, e.g., a motif to target the lysosomal sulfatase enzyme to a particular organ, tissue, or cell type. In a preferred embodiment, a fusion construct including a bone targeting peptide, e.g., 6 aspartic acid residues (6×Asp or 6D) fused to a lysosomal sulfatase enzyme may target the enzyme to particular sites in bone.

Other fusion constructs including a heterologous polypeptide with desired properties, e.g., an Ig constant region to prolong serum half-life or an antibody or fragment thereof for targeting also are contemplated. Other fusion systems produce polypeptide hybrids where it is desirable to excise the fusion partner from the desired polypeptide. In one embodiment, the fusion partner is linked to the recombinant active highly phosphorylated lysosomal sulfatase enzyme polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Derivatives

As stated above, a derivative refers to polypeptides chemically modified by such techniques as, for example and not for limitation, ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the lysosomal sulfatase enzyme are also useful as therapeutic agents and may be produced by the methods of the invention.

Polyethylene glycol (PEG) may be attached to the lysosomal sulfatase enzyme produced by the methods of the invention to provide a longer half-life in vivo. The PEG group may be of any convenient molecular weight and may be linear or branched. The average molecular weight of the PEG will preferably range from about 2 kiloDaltons ("kDa") to about 100 kDa, more preferably from about 5 kDa to about 50 kDa, most preferably from about 5 kDa to about 10 kDa. The PEG groups will generally be attached to the lysosomal sulfatase enzymes of the invention via acylation or reductive alkylation through a reactive group on the PEG moiety (e.g., an aldehyde, amino, thiol, or ester group) to a reactive group on the protein moiety (e.g., an aldehyde, amino, or ester group). Addition of PEG moieties to polypeptides of interest can be carried out using techniques well known in the art. See, e.g., International Publication No. WO 96/11953 and U.S. Pat. No. 4,179,337.

Ligation of the lysosomal sulfatase enzyme polypeptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Labels

In some embodiments, the therapeutic lysosomal sulfatase enzyme is labeled to facilitate its detection. A "label" or a "detectable moiety" is a composition detectable by spectroscopic, photochemical, biochemical, immunochemical, chemical, or other physical means. For example, labels suitable for use in the present invention include, but are not limited to, radioactive labels (e.g., $^{32}P$), fluorophores (e.g., fluorescein), electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels suitable for use in the present invention include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be coupled directly or indirectly to the desired component of the lysosomal sulfatase enzyme according to methods well known in the art. Preferably, the label in one embodiment is covalently bound to the lysosomal sulfatase enzyme using an isocyanate reagent for conjugation of an active agent according to the invention. In one aspect of the invention, the bifunctional isocyanate reagents of the invention can be used to conjugate a label to a lysosomal sulfatase enzyme to form a label lysosomal sulfatase enzyme conjugate without an active agent attached thereto. The label lysosomal sulfatase enzyme conjugate may be used as an intermediate for the synthesis of a labeled conjugate according to the invention or may be used to detect the lysosomal sulfatase enzyme conjugate. As indicated above, a wide variety of labels can be used, with the choice of label depending on sensitivity required, ease of conjugation with the desired component of the lysosomal sulfatase enzyme, stability requirements, available instrumentation, and disposal provisions. Non-radioactive labels are often attached by indirect means. Generally, a ligand molecule (e.g., biotin) is covalently bound to the lysosomal sulfatase enzyme. The ligand then binds to another molecule (e.g., streptavidin), which is either inherently detectable or covalently bound to a signal system, such as a detectable enzyme, a fluorescent compound, or a chemiluminescent compound.

The lysosomal sulfatase enzymes of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art. Thus, for example, where the label is radioactive, means for detection include a scintillation counter or photographic film, as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

In a preferred embodiment, the method comprises the step of producing active highly phosphorylated lysosomal sulfatase enzymes from cell lines with defects in endosomal trafficking. In a particularly preferred embodiment, the method comprises the step of producing active highly phosphorylated recombinant human N-acetylgalactosamine-6-sulfatase (GALNS) from the CHO cell line G71, or a derivative thereof. Production of lysosomal sulfatase enzymes such as, for example and not for limitation, GALNS, comprises the steps of: (a) developing a G71 or G71 derivative cell line that co-expresses a recombinant human lysosomal sulfatase enzyme, e.g., N-acetylgalactosamine-6-sulfatase (GALNS), and recombinant human sulfatase modifying factor 1 (SUMF1); (b) culturing human lysosomal sulfatase enzyme and SUMF1co-expressing cell lines; and (c) scaling up of the human lysosomal sulfatase enzyme and SUMF1co-expressing cell lines to bioreactor for production of lysosomal sulfatase enzymes. In preferred embodiments, the human lysosomal sulfatase enzyme, e.g., N-acetylgalactosamine-6-sulfatase (GALNS), and human SUMF1 cDNAs are subcloned into mammalian expression vectors basically as described herein below.

For cell line development, G71 or G71S, a G71 clone adapted for growth in serum-free suspension culture, was co-transfected with a human GALNS mammalian expression vector, a human SUMF1 mammalian expression vector and a selectable marker gene, and stable transformants were selected. After a first round of subcloning of stable transfectants, cell lines were selected using the fluorescent substrate and specifically designated. G71 or G71S cell lines were analyzed for cell-specific productivity (pg of product/cell) in spinners with microcarriers or in suspension culture, respectively. The best producers of human GALNS were identified and scaled-up to bioreactor for production of pre-clinical material.

In another embodiment, the invention provides a cell-based assay for measuring the activity of a recombinant human lysosomal enzyme to degrade natural substrates. The method comprises (a) culturing an isolated human cell deficient in the lysosomal enzyme under conditions in which natural substrates for the lysosomal enzyme accumulate; (b) contacting the cell with the lysosomal enzyme; (c) lysing the cell; (d) adding to the cell lysate an enzyme that (i) is specific for the natural substrates, and (ii) cleaves small oligosaccharides from the natural substrates; (e) labeling the small oligosaccharides with a detectable moiety; (f) optionally separating the labeled small oligosaccharides; (g) detecting the labeled small oligosaccharides; and (h) determining the activity of the lysosomal enzyme to degrade the natural substrates by comparing (i) the amount of labeled small oligosaccharide from cells contacted with the lysosomal enzyme with (ii) the amount of labeled small oligosaccharides from cells not contacted with the lysosomal enzyme, wherein a reduction in (h)(i) as compared to (h)(ii) indicates the activity of the lysosomal enzyme to degrade natural substrates. In one embodiment, the small oligosaccharide is a mono-, di, or tri-saccharide. In a related embodiment, the small oligosaccharide is a disaccharide.

In some embodiments, the lysosomal enzyme is selected from the group consisting of arylsulfatase B (ARSB), iduronate-2-sulfatase (IDS), sulfamidase/heparin-N-sulfatase (SGSH), N-acetylglucosamine-sulfatase (G6S) and N-acetylgalactosamine-6-sulfatase (GALNS). In some embodiments, the lysosomal enzyme is α-L-iduronidase (IDU). In some embodiments, the lysosomal enzyme is acid α-glucosidase (GAA). In some embodiments, the lysosomal enzyme is β-glucoronidase (GUSB). In some embodiments, the lysosomal enzyme is β-galactosidase (GLB1).

Suitable human cells that can be used in the cell-based assay include any human cell that is deficient in the lysosomal enzyme to be tested, such that can accumulate the natural substrates for the lysosomal enzyme. For example, cells naturally exhibiting a full (100%) or partial deficiency in activity, e.g. 30%, 50%, 70%, 80%, 90%, 95% reduction or more in activity, may be used. Cells expressing a mutant enzyme with diminished activity, or cells derived from patients suffering from a lysosomal storage disease, e.g. a mucopolysaccharidosis, may be used. Cells recombinantly altered to knockout or reduce lysosomal enzyme activity, e.g. through introducing a mutation to the encoding gene or its promoter or other regulatory region, may be used. Cells treated to reduce lysosomal enzyme activity, e.g. treated with antisense or RNAi to reduce enzyme expression, may be used.

Suitable enzymes that cleave (digest) small oligosaccharides from carbohydrates and that are "specific for" (i.e. predominantly digest) the natural substrates of the lysosomal enzyme may be selected by those of ordinary skill in the art. For example, for detection of activity of GALNS or GLB1 (enzymes that degrades keratan sulfate) the enzyme of step (d) may be Keratanase II or any enzyme that acts primarily on keratan sulfate. As another example, for detection of IDU, ARSB, IDS or GUSB (enzymes that degrade dermatan sulfate), the enzyme of step (d) may be Chondroitinase ABC or any enzyme that acts primarily on dermatan sulfate. As another example, for detection of IDU, IDS, SGHS, G6S or GUSB (enzymes that degrade heparan sulfate), the enzyme of step (d) may be Heparanase I or Heparanase II, or both. As yet another example, for detection of GAA (an enzyme that degrades glycogen), the enzyme of step (d) may be α-amylase or any enzyme that acts primarily on glycogen.

This cell-based method is capable of great sensitivity in detecting lysosomal enzyme activity. In some embodiments, the lysosomal enzyme activity is detectable when the concentration of lysosomal enzyme is as low as about 10 nM, or about 5 nM, or about 1 nM, or about 0.75 nM, or about 0.5 nM, or about 0.25 nM, or about 0.1 nM, or about 0.05 nM, or about 0.01 nM, or about 0.005 nM, or about 1 pM, or about 0.5 pM.

III. Purification of Lysosomal Sulfatase Enzymes

Bioreactor material containing recombinant human GALNS was 0.2 μm sterile filtered and kept at 4° C. The bioreactor material was either loaded onto a capture column directly, or concentrated 10- to 20-fold by ultra-filtration prior to loading onto a capture column. The bioreactor material or concentrated bioreactor material was pH adjusted to pH 4.5 and then loaded onto a Blue-SEPHAROSE® column, washed sequentially with 20 mM acetate/phosphate, 50 mM NaCl, pH 4.5 and 20 mM acetate/phosphate, 50 mM NaCl, pH 6.0 and eluted with 20 mM acetate/phosphate, 100 mM NaCl, pH 7.0. The Blue-SEPHAROSE® column eluate was then loaded onto FRACTO-GEL® SE Hi-Cap, washed sequentially with 20 mM acetate/phosphate, 50 mM NaCl, pH 5.0 and 20 mM acetate/phosphate, 50 mM NaCl, pH 5.5, and eluted with 20 mM acetate/phosphate, 50-350 mM NaCl gradient, pH 5.5. The FRACTOGEL® SE Hi-Cap eluate was formulated in 10 mM NaOAc, 1 mM NaH$_2$PO$_4$, 0.005% TWEEN®-80, pH 5.5.

Alternatively, the bioreactor material containing recombinant human GALNS was concentrated 20-fold by ultrafiltration prior to loading onto a capture column. The concentrated bioreactor material was pH adjusted to pH 4.5, filtered and then loaded onto a FRACTOGEL® SE Hi-Cap column, washed sequentially with 10 mM acetate/phosphate, 50 mM NaCl, pH 4.5 and 10 mM acetate/phosphate, 50 mM NaCl, pH 5.0, and eluted with 10 mM acetate/phosphate, 140 mM NaCl, pH 5.0. The FRACTOGEL® SE Hi-Cap column eluate was then adjusted to 500 mM NaCl, pH 7.0 and loaded onto Zn-chelating SEPHAROSE® (Zn-IMAC) column, washed with 10 mM acetate/phosphate, 125 mM NaCl, 10 mM imidazole, pH 7.0, and eluted with 10 mM acetate/phosphate, 125 mM NaCl, 90 mM imidazole, pH 7.0. The Zn-chelating SEPHAROSE® (Zn-IMAC) column eluate was adjusted to pH 3.5 for low pH viral inactivation, adjusted to 10 mM acetate/phosphate, 2M NaCl, pH 5.0, and then loaded onto a TOYOPEARL® Butyl 650M column, washed with 10 mM acetate/phosphate, 2M NaCl, pH 5.0, and eluted with 10 mM acetate/phosphate, 0.7 M NaCl, pH 5.0. The TOYOPEARL® Butyl 650M eluate was ultra-filtrated and dia-filtrated in 20 mM acetate, 1 mM phosphate, 150 mM NaCl, pH 5.5, and then formulated in 20 mM acetate, 1 mM phosphate, 150 mM NaCl, 0.01% TWEEN®-20, pH 5.5.

Alternatively, the bioreactor material containing recombinant human GALNS was filtered, concentrated 20-fold by ultrafiltration/diafiltration, and then filtered through activated carbon prior to loading onto a capture column. The concentrated bioreactor material was loaded onto a Zn-chelating SEPHAROSE® FF (Zn-IMAC) column at a conductivity ~55±5 mS/cm, washed sequentially with 10 mM acetate/phosphate, 500 mM NaCl, pH 7.0 and 10 mM acetate/phosphate, 125 mM NaCl, pH 7.0 (buffer A), and then eluted with a mixture of 70% of buffer A and 30% of 10 mM acetate/phosphate, 125 mM NaCl, 300 mM imidazole, pH 7.0 (buffer B). The Zn-chelating SEPHAROSE® FF (Zn-IMAC) column eluate was adjusted to a conductivity of ~6.0±0.5 mS/cm and pH 7.0 and loaded onto a MUSTANG® Q filter for potential removal of viruses. The MUSTANG® Q filtrate was adjusted to pH 4.5±0.1, filtered through a CUNO 60ZA filter followed by a 0.2 µm inline filter, and then loaded onto a FRACTOGEL® EMD SE Hi-Cap (M) column, washed sequentially with 10 mM acetate/phosphate, 50 mM NaCl, pH 4.5 and a mixture of 80% of buffer A (10 mM acetate/phosphate, pH 5.0) and 20% of buffer B (10 mM acetate/phosphate, 250 mM NaCl, pH 5.0), and eluted with a linear gradient 20%-75% of buffer B (in 80%-25% of buffer A). The FRACTOGEL® EMD SE Hi-Cap column eluate was then adjusted to pH 3.5±0.1 by addition of 0.2 M citrate buffer, pH 3.4 for low pH viral inactivation. The low pH viral inactivated FRACTOGEL® EMD SE Hi-Cap column eluate was adjusted to 2M NaCl and to pH 5.0 by addition of 0.2 M citrate buffer, pH 6.0, and then loaded onto a TOYOPEARL® Butyl 650M column, washed with 10 mM acetate/phosphate, 2M NaCl, pH 5.0 (buffer A), and then eluted a mixture of 35% of buffer A and 65% of buffer B (10 mM acetate/phosphate, pH 5.0). The TOYOPEARL® Butyl 650M eluate was buffer exchanged to 20 mM NaOAc/HOAc, 50 mM NaH$_2$PO$_4$, 30 mM arginine HCl, 2% (w/v) sorbitol, pH 5.4, and optionally adjusted to a final concentration of 3 mg/mL GALNS. The buffer exchanged and concentration adjusted GALNS was filtered through a viral filter (DV20) and a DNA filter (MUSTANG® Q) to remove any residual virus and DNA. TWEEN®-20 (also known as Polysorbate 20 or PS20) was added to a final concentration of 0.01% (w/v), resulting in the Bulk Drug Substance (BDS). The BDS was stored at 2-8° C. or frozen.

Alternatively, the bioreactor material containing recombinant human GALNS was filtered, concentrated 20-fold by ultrafiltration/diafiltration, and then filtered through activated carbon prior to loading onto a capture column. The concentrated bioreactor material was loaded onto a Zn-chelating SEPHAROSE® FF (Zn-IMAC) column at a conductivity ~50±5 mS/cm, washed sequentially with 10 mM acetate/phosphate, 500 mM NaCl, pH 7.0 and 10 mM acetate/phosphate, 125 mM NaCl, pH 7.0 (buffer A), and then eluted with a mixture of 70% of buffer A and 30% of 10 mM acetate/phosphate, 125 mM NaCl, 300 mM imidazole, pH 7.0 (buffer B). The Zn-chelating SEPHAROSE® FF (Zn-IMAC) column eluate was adjusted to a pH 4.5±0.1 with 1.75 M acetate, pH 4.0, filtered through a Millipore COHC filter, blended with 10 mM acetate/phosphate, pH 4.5 in a 30:70 (v/v) ratio, and then loaded onto a FRACTOGEL® EMD SE Hi-Cap (M) column at a conductivity <7 mS/cm, washed sequentially with 10 mM acetate/phosphate, 50 mM NaCl, pH 4.5 and a mixture of 80% of buffer A (10 mM acetate/phosphate, pH 5.0) and 20% of buffer B (10 mM acetate/phosphate, 250 mM NaCl, pH 5.0), and eluted with a linear gradient 20%-75% of buffer B (in 80%-25% of buffer A). The FRACTOGEL® EMD SE Hi-Cap column eluate was then adjusted to pH 3.5±0.1 by addition of 0.4 M citrate buffer, pH 3.4 for low pH viral inactivation. The low pH viral inactivated FRACTOGEL® EMD SE Hi-Cap column eluate was adjusted to 2M NaCl and to pH 5.0 5±0.1 by addition of 0.4 M citrate buffer, pH 6.0, blended with 10 mM acetate/phosphate, pH 5, containing 5 M NaCl to achieve a concentration of 2 M NaCl, and then loaded onto a TOYOPEARL® Butyl 650M column, washed sequentially with 10 mM acetate/phosphate, 2M NaCl, pH 4.4±0.1 and 10 mM acetate/phosphate, 2.5M NaCl, pH 5.0 (buffer A), and then eluted a linear gradient of 100% to 32% of buffer A and 0% to 68% of buffer B (10 mM acetate/phosphate, pH 5.0) followed by a mixture of 32% buffer A and 68% buffer B. The TOYOPEARL® Butyl 650M eluate was buffer exchanged to 20 mM NaOAc/HOAc, 50 mM NaH$_2$PO$_4$, 30 mM arginine HCl, 2% (w/v) sorbitol, pH 5.4, and optionally adjusted to a final concentration of 3 mg/mL GALNS. The buffer exchanged and concentration adjusted GALNS was filtered through a viral filter (DV20) and a DNA filter (MUSTANG® Q) to remove any residual virus and DNA. TWEEN®-20 (also known as Polysorbate 20 or PS20) was added to a final concentration of 0.01% (w/v), resulting in the Bulk Drug Substance (BDS). The BDS was stored at 2-8° C. or frozen.

The purification of recombinant human GALNS is described in detail infra, and purification of recombinant human GALNS following procedures modified from the above protocols are described in detail infra.

Figure 12:
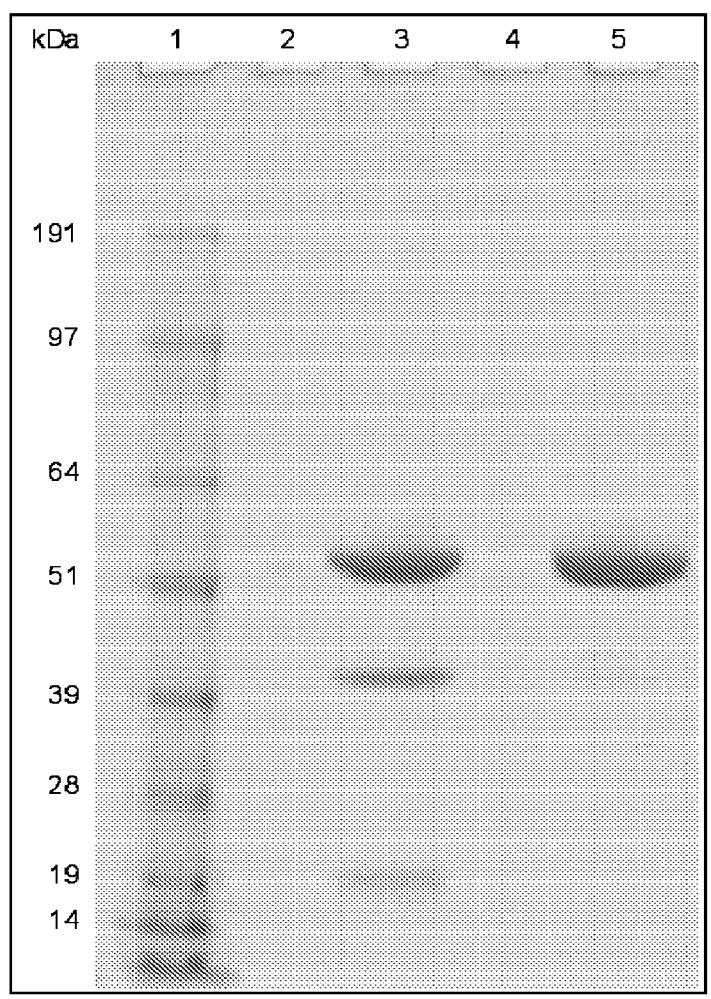
FIG. 12 shows the comparison of human N-acetylgalactosamine-6-sulfatase (GALNS) purified according to the Phase I/II process (lane 3) or the Phase III process (lane 5). Five micrograms (5 µg) of purified GALNS were separated by SDS-PAGE under reducing conditions, and the gel was stained with COOMASSIE® Blue. Lane 1 corresponds to 15 µL of SeeBlue Plus 2 Marker. The molecular weights in kDa are indicated to the left of the stained gel.

Recombinant human GALNS enzyme was expressed in G71S cells as described in Example III and purified as described in Example V or Example VI. The purified recombinant human GALNS of the invention can be compared to other documented preparations of GALNS. Masue et al., *J. Biochem.* 110:965-970, 1991 described the purification and characterization of GALNS from human placenta. The purified enzyme was found to have a molecular mass of 120 kDa, consisting of polypeptides of 40 kDa and 15 kDa, the latter of which was shown to be a glycoprotein. Thus, the Masue et al. GALNS enzyme appears to correspond to the processed form depicted in FIG. 5. Bielicki et al., *Biochem. J.* 279:515-520, 1991 described the purification and characterization of GALNS from human liver. When analysed by SDS-PAGE, the enzyme had a molecular mass of 70 kDa under non-reducing conditions and molecular masses 57 kDa, 39 kDa and 19 kDa under reducing conditions. Bielicki et al., *Biochem J.* 311: 333-339, 1995 described the purification and characterization of recombinant human GALNS from Chinese hamster ovary cells. The purified enzyme on SDS-PAGE was found to have a molecular mass of 58-60 kDa under non-reducing conditions and molecular masses of 55-57 kDa, 39 kDa and 38 kDa under reducing conditions. Thus, the Bielicki et al. GALNS enzymes appear to correspond to a mixture of the pre-processed (precursor) form of the enzyme and the processed form depicted in FIG. 5. In contrast, the recombinant human GALNS enzyme of the invention consists almost entirely of the precursor form of the enzyme (see FIG. 9 and FIG. 12), or predominantly (i.e., at least about 85%) of the precursor form of the enzyme (see FIG. 10).

IV. Lysosomal Sulfatase Enzymes and Lysosomal Storage Diseases

The lysosomal sulfatase enzyme is a full-length enzyme or any fragment, mutant, variant or derivative thereof that retains at least a substantial amount (e.g., at least about 50%, preferably at least about 75%, and more preferably at least about 90%), substantially all, or all of the therapeutic or biological activity (e.g., sulfatase activity) of the enzyme.

In some embodiments, the lysosomal sulfatase enzyme is one that, if not expressed or produced, or if substantially reduced in expression or production, would give rise to a disease, including but not limited to, lysosomal storage diseases. In some embodiments, the lysosomal sulfatase enzyme is one that, if not expressed or produced, or if substantially reduced in expression or production, may not give rise to a disease, but whose absence or reduced expression or production is associated with the disease, including but not limited to, lysosomal storage diseases. Preferably, the lysosomal sulfates enzyme is derived or obtained from a human.

Preferably, in the treatment of lysosomal storage diseases, the lysosomal sulfatase enzyme is an enzyme that is found in a cell that if not expressed or produced or is substantially reduced in expression or production, would give rise to a lysosomal storage disease. Alternatively, in the treatment of lysosomal storage diseases, the lysosomal sulfatase enzyme is an enzyme whose absence or substantially reduced expression or production is associated with the disease, although its absence or substantially reduced expression or production, may not itself give rise to the disease. Preferably, the lysosomal sulfatase enzyme is derived or obtained from a human.

Preferably, the enzyme is a lysosomal sulfatase enzyme, such as arylsulfatase A (ARSA) (Genbank Accession No. NP_000478 (isoform a), Genbank Accession No. NP_001078897 (isoform b) and other variants), arylsulfatase B/N-acetylglucosamine 4-sulfatase (ARSB) (Genbank Accession No. P15848), iduronate-2-sulfatase (IDS) (Genbank Accession No. NP_000193 (isoform a), Genbank Accession No. NP_006114 (isoform b)), sulfamidase/heparin-N-sulfatase (SGSH) (Genbank Accession No. NP_000190), N-acetylglucosamine-sulfatase (G6S) (Genbank Accession No. NP_002067) and Galactose 6-sulfatase/N-acetylgalactosamine-6-sulfatase (GALNS) (Genbank Accession No. NP_000503). A table of lysosomal storage diseases and the lysosomal sulfatase enzymes deficient therein, which are useful as therapeutic agents, follows:

| Lysosomal Storage Disease | Lysosomal Sulfatase Deficiency |
| --- | --- |
| Mucopolysaccharidosis type II Hunter syndrome | Iduronate-2-sulfatase |
| Mucopolysaccharidosis type IIIA Sanfilippo syndrome | Sulfamidase/heparin-N-sulfatase |
| Mucopolysaccharidosis type IIID Sanfilippo syndrome | N-Acetylglucosamine 6-sulfatase |
| Mucopolysaccharidosis type IVA Morquio syndrome | N-Acetylgalactosamine-6-sulfatase |
| Mucopolysaccharidosis type VI | N-Acetylgalactosamine 4-sulfatase |
| Metachromatic leukodystrophy (MLD) | Arylsulfatase A |
| Multiple sulfatase deficiency (MSD) | Multiple sulfatases |

In preferred embodiments, the lysosomal sulfatase enzyme is a recombinant human lysosomal sulfatase enzyme produced by an endosomal acidification-deficient cell line. In more preferred embodiments, the recombinant human lysosomal sulfatase enzyme is active and has a high level of phosphorylated oligosaccharides as specified under "DEFINITIONS". In most preferred embodiments, the lysosomal sulfatase enzyme is an active highly phosphorylated recombinant human N-acetylgalactosamine-6-sulfatase (GALNS).

Thus, the lysosomal storage diseases that can be treated or prevented using the methods of the present invention include, but are not limited to, Metachromic Leukodystrophy or MLD, Maroteaux-Lamy syndrome or MPS VI, Hunter syndrome or MPS II, Sanfilippo A syndrome or MPS IIIa, Sanfilippo D syndrome or MPS IIId, and Morquio A syndrome or MPS IVa. In a particularly preferred embodiment, the lysosomal sulfatase enzyme is such that its deficiency causes Morquio A syndrome or MPS IVa. In another particularly preferred embodiment, the lysosomal sulfatase enzyme is such that its deficiency is associated with a human lysosomal storage disease, such as Multiple Sulfatase Deficiency or MSD.

Thus, per the above table, for each disease the lysosomal sulfatase enzyme would preferably comprise a specific active lysosomal sulfatase enzyme deficient in the disease. For instance, for methods involving MPS II, the preferred enzyme is iduronate-2-sulfatase. For methods involving MPS IIIA, the preferred enzyme is sulfamidase/heparin-N-sulfatase. For methods involving MPS IIID, the preferred enzyme is N-acetylglucosamine 6-sulfatase. Fpr methods involving MPS IVA, the preferred enzyme is galactose 6-sulfatase/N-acetylgalactosamine-6-sulfatase. For methods involving MPSVI, the preferred enzyme is N-acetylgalactosamine 4-sulfatase. For methods involving Metachromatic Leukodystropy (MLD), the preferred enzyme is arylsulfatase A. For methods involving Multiple Sufatase Deficiency (MSD), the enzyme can be arylsulfatase A, arylsulfatase B/N-acetylglucosamine 4-sulfatase, iduronate-2-sulfatase, sulfamidase/heparin-N-sulfatase, N-acetylglucosamine-sulfatase or galactose 6-sulfatase/N-acetylgalactosamine-6-sulfatase, and the preferred enzyme is galactose 6-sulfatase/N-acetylgalactosamine-6-sulfatase.

V. Mucopolysaccharidosis Type IVA (Morquio Syndrome, MPS IVa)

Mucopolysaccharidosis type IVA (Morquio Syndrome, MPS IVa) is an inherited, autosomal recessive disease belonging to the group of mucopolysaccharide storage diseases. Morquio Syndrome is caused by a deficiency of a lysosomal enzyme required for the degradation of two glycosaminoglycans (GAGs), keratan sulfate (KS) and chondroitin-6-sulfate (C6S). Specifically, MPS IVa is characterized by the absence of the enzyme N-acetylgalactosamine-6-sulfatase (GALNS), and the excretion of KS in the urine. The lack of GALNS results in accumulation of abnormally large amounts of mucopolysaccharides in hyaline cartilage, a main component of skeletal tissues. All patients have a systemic skeletal dysplasia. Other symptoms vary in severity from patient to patient, and may include hearing loss, cataracts, spinal instability, heart valvular disease and respiratory issues, among others.

GALNS hydrolyses sulfate ester bonds of galactose-6-sulfate from KS and N-acetylgalactosamine-6-sulfate from C6S. Human GALNS is expressed as a 55-60 kDa precursor protein with only 2 potential asparagine-linked glycosylation sites. Mannose-6-phosphate (M6P) is part of the oligosaccharides present on the GALNS molecule. M6P is recognized by a receptor at the lysosomal cell surface and, consequently, is crucial for efficient uptake of GALNS.

Like all sulfatases, GALNS needs to be processed by a formylglycine-activating enzyme (FGE) encoded by the sulfatase modifying factor 1 (SUMF1) gene to gain activity. Because of this activation step, involving the post-translational modification of an active site cysteine residue to $C_\alpha$-formylglycine (FGly), over-expression of recombinant sulfatases can lead to both production of sulfatase enzymes with low specific activity (i.e., a mix of activated and non-activated sulfatase enzymes) and with low production titer (i.e., degradation and/or non-secretion of non-activated sulfatases).

An object of this invention is to provide an active highly phosphorylated human N-acetylgalactosamine-6-sulfatase enzyme useful for the treatment of Morquio Syndrome and other diseases, e.g., Multiple Sulfatase Deficiency (MSD), that are caused by or associated with a deficiency in the enzyme N-acetylgalactosamine-6-sulfatase. Such an active highly phosphorylated human N-acetylgalactosamine-6-sulfatase enzyme has the ability to localize to tissues in which KS and C6S accumulates, has adequate M6P levels for efficient uptake, has sufficiently high percentage of FGly in for enzyme activity, and has relatively high production levels.

It should be understood that the methods of the invention described herein are applicable to the production of other lysosomal sulfatase enzymes, e.g., arylsulfatase A (ARSA), arylsulfatase B/N-acetylglucosamine 4-sulfatase (ARSB), iduronate-2-sulfatase (IDS), sulfamidase/heparin-N-sulfatase (SGSH) and N-acetylglucosamine-sulfatase (G6S), useful for the treatment of lysosomal storage diseases which are caused or characterized by their deficiency thereof.

VI. Pharmaceutical Compositions and Administration

The lysosomal sulfatase enzymes of the invention may be administered by a variety of routes. For oral preparations, the lysosomal sulfatase enzymes can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The lysosomal sulfatase enzymes of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The lysosomal sulfatase enzymes of the invention can be utilized in aerosol formulation to be administered via inhalation. The lysosomal sulfatase enzymes of the invention can be formulated into pressurized acceptable propellants such as dichlorodifluoromethane, propane, nitrogen and the like.

Furthermore, the lysosomal sulfatase enzymes of the invention can be made into suppositories by mixing with a variety of bases such as emulsifying bases or water-soluble bases. The lysosomal sulfatase enzymes of the invention can be administered rectally via a suppository. The suppository can include vehicles such as cocoa butter, carbowaxes and polyethylene glycols, which melt at body temperature, yet are solidified at room temperature.

Unit dosage forms of the lysosomal sulfatase enzymes of the invention for oral or rectal administration such as syrups, elixirs, and suspensions may be provided wherein each dosage unit, for example, teaspoonful, tablespoonful, tablet or suppository, contains a predetermined amount of a lysosomal sulfatase enzyme containing active agent. Similarly, unit dosage forms for injection or intravenous administration may comprise the lysosomal sulfatase enzyme as a solution in sterile water, normal saline or another pharmaceutically acceptable carrier.

In practical use, the lysosomal sulfatase enzymes of the invention can be combined as the active ingredient in intimate admixture with one or more pharmaceutically acceptable carriers, diluents or excipients according to conventional pharmaceutical compounding techniques. The carrier, diluent or excipient may take a wide variety of forms depending on the preferable form of preparation desired for administration, e.g., oral or parenteral (including intravenous). In preparing the lysosomal sulfatase enzyme compositions for oral dosage form, any of the usual pharmaceutical media may be employed, such as, for example, water, glycols, oils, alcohols, flavoring agents, preservatives, coloring agents and the like in the case of oral liquid preparations, for example, suspensions, elixirs and solutions; or carriers such as starches, sugars, microcrystalline cellulose, diluents, granulating agents, lubricants, binders, disintegrating agents and the like in the case of oral solid preparations, for example, powders, hard and soft capsules and tablets, with the solid oral preparations being preferred over the liquid preparations.

The invention provides formulations of any of the GALNS enzyme preparations described herein, optionally at a concentration of from about 0.1 to 5 mg/mL (or 0.5to 1.5 mg/mL) protein, and optionally at a pH of about 5-5.8, comprising (i) an amount of phosphate buffer effective to reduce dephosphorylation of said GALNS enzyme; and (ii) a stabilizing amount of one or more stabilizers selected from the group consisting of amino acid salts, amino acid buffers, surfactants and polyols. In some embodiments, the formulation may comprise a second buffering agent. In certain embodiments, the formulations comprise any of the purified recombinant human GALNS enzyme preparations described herein, a phosphate buffer at a concentration between about 25 mM and about 75 mM, an acetate buffer at a concentration between about 10 mM and about 30 mM, and a stabilizer that reduces protein aggregation. In some embodiments, the formulation comprises an arginine or histidine salt or buffer, and optionally a non-ionic surfactant, and optionally a trihydric or higher polyol (sugar alcohol). In specific embodiments, the formulation comprises an arginine salt or buffer, a polysorbate, optionally polysorbate 20, and a sorbitol. In any of these embodiments, the phosphate buffer may be NaH$_2$PO$_4$. In any of these embodiments, the acetate buffer may be NaOAc/HOAc.

The second buffering agent may be any agent suitable to maintain a pH within the desired range. Suitable buffers include Tris, citrate, succinate, acetate, gluconate, or other organic acid buffers. In some embodiments, the stabilizer is an amino acid salt or buffer, optionally a salt or buffer of arginine, lysine, glycine, glutamine, asparagine, histidine, alanine, ornithine, leucine, 2-phenylalanine, or glutamic acid. In some embodiments, the stabilizer is a surfactant, optionally a non-ionic surfactant. Suitable surfactants include polysorbates, e.g. polysorbate 20 or polysorbate 80, poloxamers, e.g., polyxamer 188 or 184, polyoxyethylene derivatives, polyoxypropylene derivatives, sodium monolaurate, and SDS. Non-limiting examples of known nonionic surfactants include aliphatic, primary or secondary linear or branched chain alcohols or phenols with alkylene oxides, generally ethylene oxide and generally 6-30 ethylene oxide groups. Other known nonionic surfactants include mono- or di-alkyl alkanolamides, alkyl polyglucosides, and polyhydroxy fatty acid amides. Non-limiting examples of known anionic surfactants include the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Known anionic surfactants include sodium or ammonium lauryl sulfate and sodium or ammoinium lauryl ether sulfate. Non-limiting examples of known amphoteric surfactants include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms.

In some embodiments, the stabilizer is a polyol or sugar, preferably a trihydric or higher sugar alcohol. Suitable polyols include erythritol, arabitol, maltitol, cellobiitol, lactitol, mannitol, threitol, sorbitol, xylitol, ribitol, myoinisitol, galactitol, glycerol, and glycerin. Known polyols also include alcohols derived from lactose, trehalose, and stachyose, Known nonreducing sugars include sucrose, trehalose, sorbose, melezitose and raffinose. Known sugars also include xylose, mannose, fructose, glucose; disaccharides such as lactose, maltose, sucrose, trisaccacharides such as raffinose, and polysaccharides such as dextran.

The invention also provides a method of preventing dephosphorylation of purified recombinant human GALNS enzyme, comprising mixing said GALNS enzyme and an amount of a phosphate buffer effective to reduce dephosphorylation, optionally to a final concentration between about 25 mM and about 75 mM phosphate buffer. In some embodiments, the purified recombinant human GALNS enzyme is also mixed with a second buffering agent, including any of the agents described above. In some embodiments, the enzyme is also mixed with a stabilizing amount of one or more stabilizers selected from the group consisting of amino acid salts, amino acid buffers, surfactants and polyols. In exemplary embodiments, the amount of dephosphorylation is reduced compared to a formulation of the same enzyme in 1 mM phosphate buffer, e.g. when tested after 1 week, 2 weeks, 3 weeks, 1 month, 2 months, 3 months, 4 months, 5 months or 6 months of storage at room temperature (e.g. 25° C.). In specific embodiments, accelerated stability testing is carried out after storage for such periods of time at 40° C.

In certain embodiments, the reduction in dephosphorylation in the GALNS formulation (compared to the 1 mM phosphate buffer) can be at least about 2%, about 3%, about 4%, about 5%, about 10%, about 15%, about 20%, about 30%, about 40% or about 50% or greater. In another embodiment, the the level of bis-phosphorylated mannose 7 (BPM7) on the GALNS in the formulation is from about 25% to about 40%, or about 30% to 35%.

In embodiments of any of the foregoing formulations or methods, the GALNS enzyme may be a recombinant human N-acetylgalactosamine-6-sulfatase (GALNS) enzyme comprising an amino acid sequence at least 95% identical to amino acids 27 to 522 of SEQ ID NO:4, and (i) having a purity of at least about 95% as determined by COOMASSIE® Blue staining when subjected to SDS-PAGE under non-reducing conditions, (ii) having at least about 80% conversion of the cysteine residue at position 53 to Cα-formylglycine (FGly), and (iii) having between 0.5 to 0.8 bis-phosphorylated oligomannose chains per monomeric protein chain, wherein at least 70%, at least 80%, at least 85%, at least 90%, at least 95%, at least 97%, at least 98%, at least 98.5%, at least 99% or at least 99.5% of said GALNS enzyme is in the precursor form as determined by COOMASSIE® Blue staining when subjected to SDS-PAGE under reducing conditions, or by SDS-capillary gel electrophoresis (SDS-CGE).

With respect to transdermal routes of administration, methods for transdermal administration of drugs are disclosed in Remington's Pharmaceutical Sciences, 17th Edition, (Gennaro et al., Eds. Mack Publishing Co., 1985). Dermal or skin patches are a preferred means for transdermal delivery of the lysosomal sulfatase enzymes of the invention. Patches preferably provide an absorption enhancer such as DMSO to increase the absorption of the lysosomal sulfatase enzymes. Other methods for transdermal drug delivery are disclosed in U.S. Pat. Nos. 5,962,012, 6,261,595, and 6,261,595, each of which is incorporated by reference in its entirety.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are also commercially available.

In each of these aspects, the lysosomal sulfatase enzyme compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The lysosomal sulfatase enzyme compositions may be conveniently presented in unit dosage form and prepared by any of the methods well known in the art of pharmacy.

Because of their ease of administration, tablets and capsules represent the most advantageous oral dosage unit form in which case solid pharmaceutical carriers are obviously employed. If desired, tablets may be coated by standard aqueous or non-aqueous techniques. The percentage of an active lysosomal sulfatase enzyme in these compositions may, of course, be varied and may conveniently be between about 2 percent to about 60 percent of the weight of the unit.

Lysosomal sulfatase enzyme compositions of the invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer lysosomal sulfatase enzymes intracellularly and to deliver lysosomal sulfatase enzymes to the target organs. Controlled release of a lysosomal sulfatase enzyme of interest may also be achieved using encapsulation (see, e.g., U.S. Pat. No. 5,186,941).

Any route of administration that dilutes the lysosomal sulfatase enzyme composition into the blood stream, or preferably, at least outside of the blood-brain barrier, may be used. Preferably, the lysosomal sulfatase enzyme composition is administered peripherally, most preferably intravenously or by cardiac catheter. Intrajugular and intracarotid injections are also useful. Lysosomal sulfatase enzyme compositions may be administered locally or regionally, such as intraperitoneally, subcutaneously or intramuscularly. In one aspect, lysosomal sulfatase enzyme compositions are administered with one or more pharmaceutically acceptable carrier, diluent or excipient.

Those of skill will readily appreciate that dose levels can vary as a function of the specific lysosomal sulfatase enzyme, the severity of the symptoms and the susceptibility of the subject to side effects. Preferred dosages for a given lysosomal sulfatase enzyme are readily determinable by those of skill in the art by a variety of means including, but not limited to, dose response and pharmacokinetic assessments conducted in patients, in test animals and in vitro.

Dosages to be administered may also depend on individual needs, on the desired effect, the particular lysosomal sulfatase enzyme used, and on the chosen route of administration. Dosages of a lysosomal sulfatase enzyme range from about 0.2 pmol/kg to about 20 nmol/kg, preferred dosages range from 2 pmol/kg to 2 nmol/kg, and particularly preferred dosages range from 2 pmol/kg to 200 pmol/kg. Alternatively, dosages of the lysosomal sulfatase enzyme may be in the range of 0.01 to 1000 mg/kg, preferred dosages may be in the range of 0.1 to 100 mg/kg, and particularly preferred dosages range from 0.1 to 10 mg/kg. These dosages will be influenced by, for example and not for limitation, the particular lysosomal sulfatase enzyme, the form of the pharmaceutical composition, the route of administration, and the site of action of the particular lysosomal sulfatase enzyme.

The lysosomal sulfatase enzymes of the invention are useful for therapeutic, prophylactic and diagnostic intervention in animals, and in particular in humans. Lysosomal sulfatase enzymes may show preferential accumulation in particular tissues. Preferred medical indications for diagnostic uses include, for example, any condition associated with a target organ of interest (e.g., lung, liver, kidney, spleen).

The subject methods find use in the treatment of a variety of different disease conditions. In certain embodiments, of particular interest is the use of the subject methods in disease conditions where a lysosomal sulfatase enzyme having desired activity has been previously identified, but in which the lysosomal sulfatase enzyme is not adequately delivered to the target site, area or compartment to produce a fully satisfactory therapeutic result. With such lysosomal sulfatase enzymes, the subject methods of producing active highly phosphorylated lysosomal sulfatase enzymes can be used to enhance the therapeutic efficacy and therapeutic index of the lysosomal sulfatase enzyme.

Treatment is meant to encompass any beneficial outcome to a subject associated with administration of a lysosomal sulfatase enzyme including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least no longer suffers from the symptoms that characterize the pathological condition.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Having now generally described the invention, the same may be more readily understood through the following reference to the following examples, which provide exemplary protocols for the production, and purification of active highly phosphorylated lysosomal sulfatase enzymes and their use in the treatment of lysosomal storage diseases. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example I

Mammalian Expression Vectors for Human Sulfatase Modifying Factor 1 (SUMF1) and Human N-Acetylgalactosamine-6-Sulfatase (GALNS)

The objective was to construct mammalian expression vectors appropriate for producing in stably transfected cells adequate amounts of active lysosomal sulfatase enzymes with improved phosphorylation levels.

The full-length human sulfatase modifying factor 1 (SUMF1) cDNA (see United States Patent Application Nos. US 20005/0123949, publication date Jun. 9, 2005, and US 2004/0229250, publication date Nov. 8, 2004, both of which are herein incorporated by reference in their entirety), which encodes a 374 amino acid polypeptide, was cloned into the mammalian expression vector cDNA4 (Invitrogen, Carlsbad, Calif.), which contains the human CMV enhancer-promoter and a multiple cloning site. Efficient transcript termination was ensured by the presence of the bovine growth hormone polyadenylation sequence. The selection marker was a zeocin resistance gene under the control of the EM-7 promoter and SV40 early polyadenylation sequence. The resultant plasmid was designated pcDNA4 SUMF1. The human SUMF1 polynucleotide (SEQ ID NO:1) and polypeptide (SEQ ID NO:2) sequences are shown in FIG. 1 and FIG. 2, respectively.

The full-length human N-acetylgalactosamine-6-sulfatase (GALNS) cDNA (see Tomatsu et al., *Biochem. Biophys. Res. Commun.* 181(2):677-683, 1991), which encodes a 522 amino acid polypeptide including a 26 amino acid signal peptide, was cloned into the mammalian expression vector pCIN (BioMarin), which contains the human CMV enhancer-promoter linked to the rabbit β-globin IVS2 intron and a multiple cloning site. Efficient transcript termination was ensured by the presence of the bovine growth hormone polyadenylation sequence. The selection marker was a neomycin phosphotransferase gene that carries a point mutation to decrease enzyme efficiency. The attenuated marker was further handicapped with the weak HSV-tk promoter. The resultant plasmid was designated pCIN 4A. The human GALNS polynucleotide (SEQ ID NO:3) and polypeptide (SEQ ID NO:4) sequences are shown in FIG. 3 and FIG. 4, respectively.

To increase the expression levels of SUMF1 and GALNS, scaffold/matrix attachment region (MAR) elements (see Mermod et al., U.S. Pat. No. 7,129,062) were cloned into the SUMF1 and GALNS expression plasmids.

BMAR SUMF1 was made by digesting P<1_68 X_X NcoI filled MAR (Selexis) with BamHI and HincII, and then inserting the released MAR fragment into pcDNA4 SUMF1 digested with BglII and NruI.

PMAR SUMF1 was made digesting P<1_68 NcoI filled (MAR) SV40 EGFP (Selexis) with HindIII and XbaI to remove the EGFP gene, and then inserting the SUMF1 gene, which was released from pcDNA4 SUMF1 by digestion with HindIII and XbaI.

BMAR 4A was made by digesting BMAR SUMF1 with PmeI and SpeI to remove the SUMF1gene, and then inserting the GALNS gene, which was released from pCIN 4A by digestion with PmeI and SpeI.

PMAR 4A was made by digesting P<1_68 NcoI filled (MAR) SV40 EGFP (Selexis) with HindIII and XbaI to remove the EGFP gene, and then inserting the GALNS gene, which was released from pCIN 4A by digestion with HindIII and XbaI.

The full-length human GALNS cDNA was also cloned into the mammalian expression vector pcDNA4(Invitrogen, Carlsbad, Calif.). pcDNA4 SUMF1was digested with HindIII and XbaI to remove the SUMF1 cDNA, and pCIN 4A was digested with HindIII and XbaI to isolate the GALNS cDNA. The GALNS cDNA HindIII/XbaI fragment was ligated into the pcDNA4vector HindIII/XbaI fragment. The resultant plasmid was designated pcDNA4-4A.

The integrity of the GALNS gene in the pCIN 4A, BMAR and pCDNA4-4A expression vectors was confirmed by restriction mapping using enzymes obtained from New England Biolabs. The PMAR 4A expression vector was not mapped.

The structure of the fully processed form of human N-acetylgalactosamine-6-sulfatase (GALNS) is depicted in FIG. 5. GALNS is expressed as a 522 amino acid polypeptide with a 26 amino acid signal peptide sequence. A 496 amino acid GALNS polypeptide is secreted as a pre-processed (precursor) form of the enzyme having a molecular weight of about 55-60 kDa. In active GALNS, the cysteine residue at position 53 of the precursor or fully processed GALNS polypeptide (corresponding to position 79 of the full-length GALNS polypeptide) has been converted to $C_\alpha$-formylglycine (FGly) by sulfatase modifying factor 1 (SUMF1). In the lysosome, GALNS is cleaved after position 325 of the fully processed GALNS polypeptide, resulting in GALNS peptide fragments of about 40 kDa and 19 kDa. These GALNS peptides are joined by a disulfide bridge between the cysteine (C) residues at positions 282 and 393 of the fully processed GALNS polypeptide. There are two canonical N-linked glycosylation sites, at positions 178 and 397 of the fully processed GALNS polypeptide. Bis-phosphorylated mannose 7(BPM7), comprising 2mannose-6-phosphate residues, has been found on N178, but not on N397.

Example II

G71S Cell Lines Co-Expressing Human Sulfatase Modifying Factor 1(SUMF1) and Human N-Acetylgalactosamine-6-Sulfatase (GALNS)

The objective was to develop cell lines capable of producing active lysosomal sulfatase enzymes with improved phosphorylation levels.

G71 cells (Rockford K. Draper) were derived directly from CHO-K1(ATCC CCL-61). The G71 cell line is a temperature-sensitive mutant of CHO-K1with respect to acidification of the endosomes, which has been observed to yield differences in total protein secretion and phosphorylation on mannose residues for several enzymes at elevated temperatures (Park et al., *Somat. Cell Mol. Genet.* 17(2): 137-150, 1991; Marnell et al., *J. Cell. Biol.* 99(6): 1907-1916, 1984).

G71 cells were maintained at 34° C. in BioWhittaker ULTRACHO® medium supplemented with 2.5% fetal calf serum, 2mM glutamine, gentamycin and amphotericin.

To allow easier use of cell lines for protein production, the adherent G71 cells were pre-adapted to serum-free growth medium using a protocol for adapting anchorage-dependent, serum-dependent mammalian cells to high density serum-free suspension culture (Sinacore et al., *Mol. Biotechnol.* 15(3):249-257, 2000), resulting in the serum-free suspension culture adapted cell line, G71S. Alternatively, adherent G71 cells, after being stably transfected as described infra, may be adapted to serum-free growth medium as outlined in Sinacore et al.

Paired combinations of the human SUMF1 and human GALNS expression vectors (Example I), either pcDNA4SUMF1 plus pCIN4 4A, BMAR SUMF1plus BMAR 4A, or PMAR SUMF1 plus PMAR 4A, were transfected following the MARtech II protocol as described by Selexis into G71S cells grown in culture medium supplemented with Antibiotic-Antimycotic Solution (100 IU Penicillin, 10 mg Streptomycin, 25 μg Amphotericin B, Cellgro). Transfectant pools were grown in ULTRACHO® medium (Cambrex) supplemented with 5% γ-irradiated fetal bovine serum (FBS, JRH), 200 μg/mL G418 (AG Scientific) and 200 μg/mL Zeocin (Invitrogen), and cloned by limiting dilution in 96-well plates in the same growth medium. Clone growth was monitored by Cell Screen (Innovatis) imaging. All clones were screened using an enzyme capture activity ELISA for active GALNS (see Example IV). Cellular productivity was calculated by dividing enzyme capture activity ELISA for GALNS activity by cell growth (VI-CELL®, Beckman Coulter) per day, over a period of 4 days.

202 G71S clones were generated and screened for active GALNS: 86 clones co-transfected with pcDNA4 SUMF1plus pCIN 4A, 65 clones co-transfected with BMAR SUMF1 plus BMAR 4A, and 51 clones co-transfected with PMAR SUMF1plus PMAR 4A. Clones were initially selected on the basis of high levels of active GALNS from the 96-well tissue culture plates (FIG. 6A). GALNS activity was measured using an enzyme capture activity ELISA and represented in ng/mL (y-axis). The x-axis shows the three co-transfection conditions used for SUMF1and GALNS expression: hCMV promoter without MAR, hCMV promoter with MAR, and SV40 promoter with MAR. Each bar represents a single clone from the respective population. Cell density was not accounted for in this 96-well clone screen and not all of the co-transfected G71S clones are displayed in this figure.

The highest active GALNS producing G71S clones were chosen for productivity analysis (FIG. 6B). Daily cellular productivity was measured in pg/cell/day and obtained by dividing the GALNS activity by the cell density for that day. This figure displays the fourth day (96 hours) after seeding at $5 \times 10^5$ cells/flask. The clones were assayed for GALNS using an enzyme capture activity ELISA in pg/cell/day (y-axis). Positive controls consisted of GALNS expressing BHK and CHO clones (BioMarin). Each vertical bar represents a single clone. Active GALNS was produced by pCIN 4A clones, but only marginally above the background of the assay.

Analysis of clones by the 96-well screen and 4-day productivity assay demonstrated that co-transfection of expression vectors with MAR elements increased the productivity of G71S clones as compared to co-transfection of expression vectors without MAR elements. The BMAR 4A+BMAR SUMF1co-transfected clones demonstrated fast pool generation, rapid clone growth, and ability to produce greater than 2-fold more active GALNS than the highest producing PMAR 4A clones, and up to a 10-fold increase over CHO 4A and BHK 4A clones lacking MAR elements.

The GALNS expressing G71S clones were adapted to serum-free growth medium using the protocol outlined in Sinacore et al., *Mol. Biotechnol.* 15(3):249-257, 2000. The entire adaptation was done in the presence of both selection agents (zeocin at 200 µg/mL and neomycin at 200 µg/mL). The GALNS expressing G71 clones cultured in T-flasks were split as follows: (1) into a 125 mL shaker with the Cambrex ULTRACHO® medium and 5% FBS (lot #8L2242); (2) into a 125 mL shaker with the JRH 302M medium (production medium) and 5% FBS; and (3) into T-flasks as a back-up (ULTRACHO®, 5% FBS). Once suspension cultures were established, adherent cells were discarded, and weaning from FBS was initiated. When the growth rate returned to >0.5 (1/day) for 3 passages and the viability was >95%, the FBS concentration was reduced by 50%. The cells were left at any given FBS concentration for a minimum of 3 passages. Once adapted to growth in 2.5% FBS, the cells were taken directly into serum-free media. Cells were banked in fresh media with 10% (v/v) DMSO. A trial thaw was tested to insure that the cells survived the freeze process. Two GALNS expressing G71S clones from the BMAR 4A+BMAR SUMF1 transfection, clones 4 and 5 took approximately 15 passages for adaptation to serum-free suspension culture. A GALNS expressing clone from the pcDNA4 SUMF1 plus pCIN 4A transfection, C6, was also isolated and adapted to serum-free culture.

Paired combinations of the human SUMF1 and human GALNS expression vectors (Example I), pcDNA4 SUMF1 plus pCDNA4-4A, were transfected into G71S cells basically as described above, except 200 µg/mL Zeocin (Invitrogen) was used for selection. Six GALNS expressing clones, C2, C5, C7, C10, C11 and C30, were isolated and adapted to serum-free suspension culture basically as described above.

Example III

Large-Scale Culture of G71S Cell Lines Expressing Human N-Acetylgalactosamine-6-Sulfatase (GALNS)

The objective was to measure enzyme production from the G71S clones expressing human N-acetylgalactosamine-6-sulfatase (GALNS). Serum-free suspension culture adapted G71S cell lines co-expressing human SUMF1 and human GALNS were cultured in large-scale and assessed for active GALNS enzyme production.

Figure 7:
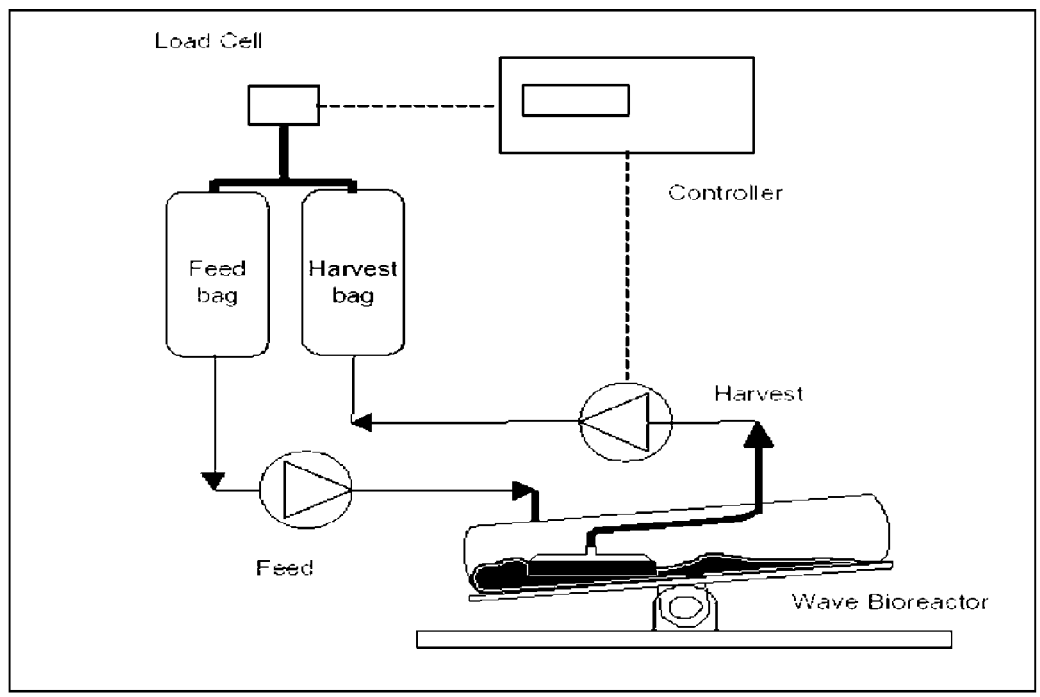
FIG. 7 illustrates a schematic of the WAVE bioreactor controller used for large-scale production of G71S cells expressing human N-acetylgalactosamine-6-sulfatase (GALNS) and variants thereof.

Since adaptation to serum-free suspension culture was relatively quick for the G71S host cell line, it was decided that production could be done in a WAVE bioreactor operated in perfusion mode. The WAVE bioreactor allows greater flexibility in inoculum volume because scale-up can be done directly in the bag, reducing the risk of contamination and expediting the production of material. FIG. 7 shows the schematic of WAVE bioreactor setup. The diagram shows, in perfusion mode, that a load cell monitors the media volume in the bag by determining the weight of the bag and adjusting the feed and harvest rates to maintain the desired volume. In the 10 L bag, the pH is also controlled to the desired set-point by a probe that is inserted into the bag.

The material from the GALNS expressing G71S clones 4and 5was produced at the 1 L scale. The culture pH was not controlled in these runs. The operational limitation of the WAVE bag is a throughput of 3 vessel volumes a day (VV/day). In order to prevent any inactivation of material, the target cell specific perfusion rate (CSPR) was 0.3 nl/cell/day, resulting in an average residence time of eight hours for the GALNS enzymes. Therefore, the cell density in the bag was maintained at approximately 10-12 $\times 10^6$ cells/mL. The growth rate for GALNS expressing G71S clones 4 and 5 was 0.16 and 0.20, respectively. Bleeds to maintain target cell density were done directly from the bag.

The harvest fluid pH was adjusted to a pH between 5.5 and 6.5 to maintain enzymatic activity, since GALNS had previously been shown to be stable at pH 6. This was accomplished by a timed bolus addition of 5% by volume pH 4.0 sodium citrate buffer mixed in line with harvest coming off the reactor. The adjusted harvest fluid was stored at 4° C. prior to downstream processing. The two GALNS expressing G71S clones 4 and 5 averaged titers of about 4.2 mg/L with an associated specific productivity of about 1.25 pg/cell/day.

The GALNS expressing G71S clones, C2, C5, C6, C7, C10, C11 and C30, were similarly cultured in large-scale and assessed for active GALNS enzyme production.

Example IV

Measurement of the Concentration and Activity of Human N-Acetylgalactosamine-6-Sulfatase (GALNS)

Enzyme linked immunosorbant assays (ELISAs) were developed to measure GALNS enzyme concentration and activity from the G71S clones co-expressing human SUMF1 and human N-acetylgalactosamine-6-sulfatase (GALNS).

Enzyme Capture Activity ELISA

The enzyme capture activity ELISA measures the activity of GALNS enzyme in solid phase, following the capture by an anti-GALNS specific antibody bound to an ELISA plate.

Buffers. Buffer A (Carbonate Buffer): dissolve 3.09 grams of $Na_2CO_3$ and 5.88 grams of $NaHCO_3$ in 900 mL of de-ionized (DI) $H_2O$, then add DI $H_2O$ to a final volume of 1000 mL. Check that the pH is between 9.4 and 9.6, then filter-sterilize. To completely coat one 96-well microplate with 100 μL per well, dilute 19 μL of an anti-GALNS antibody into one tube (12 mL). Buffer B (ELISA Blocking Buffer and Serial Dilution Buffer): 1× Acidic PBS, 0.05% TWEEN®-20 and 2% BSA, adjusted to pH 6.5 with acetic acid. Buffer $B^W$ (Wash Buffer): 100 mM NaOAc and 0.05% TWEEN®-20, adjusted to pH 6.5 with acetic acid. Buffer C (Substrate Buffer): 25 mM Sodium Acetate, 1 mM NaCl, 0.5 mg/mL desalted BSA and 0.01% sodium azide, adjusted to pH 4.0 with glacial acetic acid. Buffer D (β-Galactosidase Buffer): 300 mM sodium phosphate dibasic, 0.1 mg/ml BSA, 0.01% sodium azide and 0.01% TWEEN®-20, adjusted to pH 7.2 with phosphoric acid. Buffer E (Stop Buffer): 350 mM glycine and 440 mM carbonate buffer, adjusted to pH 10.7 with 6 M NaOH.

Reagents. Anti-GALNS IgG antibody: polyclonal rabbit antibodies are Protein G purified from serum. In D-PBS, total protein=3.17 mg/mL (BCA). Aliquots (19 μL) are stored at −20° C. for one-time use each. 4MU-Gal-6-S Substrate (Solid; 440 MW): 100 mM stock prepared in DI water and stored at 4° C. β-Galactosidase (Sigma G-4155): dilute to 12 μg/mL in Buffer D prior to use.

Protocol: Bind anti-GALNS antibody to plate: a Nunc MaxiSorp ELISA plate (Nalge/Nunc International, Fisher #12-565-135) is coated with anti-GALNS antibody at a final protein concentration of 5 μg/mL in Buffer A. To prepare this solution, thaw one 19 μL aliquot, spin briefly (10 sec) in a microcentrifuge to collect the liquid. Transfer all 19 μL into 12 mL of Buffer A. Mix vigorously by inversion, then pour into a reservoir, followed by plate loading (100 μL per well) using a multi-channel pipettor. Cover the plate and incubate at 4° C. overnight. Remove unbound anti-GALNS antibody: wash the plate by flooding with Buffer $B^W$ three times. Block: block the plate with Buffer B (320 μL per well), then cover the plate and incubate at 37° C. for 1 hr. Prepare a dilution series of purified GALNS standard and test samples (unknowns) during the block step: the standard is diluted in Buffer B to the high end of the linear range of the assay (128 ng/mL in Row A), then serially diluted (2-fold) in rows B-G on a 96-well plate. Lane H is buffer blank (i.e., no GALNS enzyme). First, prepare 500 μL of a concentration at 128 ng/mL in Buffer B. Then, dilute serial 2-fold in the Buffer B (250 μL into 250 μL) until reaching 2 ng/mL. Remove blocking buffer: after the block step, Buffer B is discarded. Bind GALNS enzyme standard and test samples to anti-GALNS antibody: load the plate with 100 μL/well of the serially diluted standard and test samples (run in duplicate). Cover the plate and incubate at 37° C. for 1 hr. Remove GALNS inhibitors: wash the plate by flooding with Buffer $B^W$, three times. Add GALNS substrate (first reaction): prepare enough final substrate solution for loading 100 μL per well (prepared no more than 1 hour before use). Dilute the 4MU-Gal-6-S stock solution (100 mM) to 1 mM in Buffer C. Load 100 μL per well. Cover the plate and incubate at 37° C. for 30 min. Add β-Galactosidase (second reaction): add 50 μL of 12 μg/ml β-galactosidase in Buffer D to each well. Cover the plate and incubate at 37° C. for 15 min. Stop reaction: add 100 μL of Buffer E (stop buffer) to each well to ionize released 4MU. Transfer to fluoroplate: transfer (8 wells at a time) 200 μL of the 250 μL from each well of the ELISA plate to a black untreated flat-bottom microtiter plate (Fluoroplate, Costar #3915). Read fluorescence: read the plate in a Gemini plate reader (Molecular Devices Corporation) using the SOFTmax PRO program (366 nm excitation, 446 nm emission, 435 nm cutoff).

GALNS ELISA

The GALNS ELISA measures the concentration of the GALNS enzyme in cell culture conditioned medium or other process samples using a sandwich immunoassay.

Buffers. Buffer A (Carbonate Buffer): dissolve 3.09 grams of $Na_2CO_3$ and 5.88 grams of $NaHCO_3$ in 900 mL of de-ionized (DI) $H_2O$, then add DI $H_2O$ to a final volume of 1000 mL. Check that the pH is between 9.4 and 9.6, then filter-sterilize. To completely coat one 96-well microplate with 100 μL per well, dilute 19 μL of anti-GALNS antibody into one tube (12 mL). Buffer B (ELISA Blocking Buffer and Serial Dilution Buffer): 1× acidic PBS, 0.05% TWEEN®-20 and 2% BSA, adjusted to pH 6.5 with acetic acid. Buffer $B^W$ (Wash Buffer): 100 mM NaOAc and 0.05% TWEEN®-20, adjusted to pH 6.5 with acetic acid. Buffer F (Stop Buffer): 2N $H_2SO_4$: in 600 mL total, add 100 mL of 12N $H_2SO_4$ and 500 mL MilliQ water.

Reagents. Anti-GALNS IgG antibody: rabbit polyclonal antibodies are Protein G purified from serum. In D-PBS, total protein=3.17 mg/mL (BCA). Aliquots (19 μL) are stored at −20° C. for one-time use each. HRP-conjugated detecting antibody (RIVAH): the final conjugated antibody is diluted 1:100 into D-PBS/1% BSA and stored in 120 μL aliquots at −20° C. for one-time use. TMB EIA Substrate Kit (BioRad #172-1067).

Protocol. Bind anti-GALNS antibody to the plate: a Nunc MaxiSorp ELISA plate (Nalge/Nunc International, Fisher #12-565-135) is coated with anti-GALNS antibody at a final protein concentration of 5 μg/mL in Buffer A. To prepare this solution, thaw one 19 μL aliquot, spin briefly (10 sec) in a microcentrifuge to collect the liquid. Transfer all 19 μL into 12 mL of Buffer A. Mix vigorously by inversion, then pour into a reservoir, followed by plate loading (100 μL per well) using a multi-channel pipettor. Cover the plate and incubate at 37° C. (convection incubator) for 2 hr. Do not use a hot block. Remove unbound anti-GALNS antibody: wash the plate by flooding with Buffer $B^W$, three times. Block: block the plate with Buffer B (320 μL per well), then cover the plate and incubate at 37° C. for 1 hr. Prepare dilution series of purified GALNS standard and test samples (unknowns) during block step: the standard is diluted in Buffer B to the high end of the linear range of the assay (40 ng/mL in Row A), then serially diluted (2-fold) in rows B-G on a 96-well plate. Lane H is buffer blank (i.e., no GALNS enzyme). First, prepare 500 μL of a concentration at 40 ng/mL in Buffer B. Then, dilute serial 2-fold in the Buffer B (250 μL into 250 μL) until reaching 0.625 ng/mL. Remove blocking buffer: after the block step, Buffer B is discarded. Bind GALNS enzyme standard and test samples to anti-GALNS antibody: load the plate with 100 μL/well of the serially diluted standard and test samples (run in duplicate). Cover the plate and incubate at 37° C. for 1 hr. Wash: wash the plate by flooding with Buffer $B^W$, three times. Bind detecting antibody conjugate: thaw one aliquot (120 μL) of antibody RIVAH, spin briefly (10 sec) in a microcentrifuge to collect the liquid. Dilute all 120 μL into 11.9 mL Buffer B and vigorously invert the tube to mix. Pour into reservoir and add 100 μL per well with the multichannel pipettor. Cover the plate and incubate at 37° C. for 30 min. Wash: wash the plate by flooding with Buffer B$^W$, three times. TMB substrate: prepare the final substrate solution by mixing 1.2 mL of Solution B with 10.8 mL of Solution A. Pour into reservoir and add 100 µL per well with the multichannel pipettor. Cover the plate and incubate at 37° C. for 15 min. Stop solution: Pipette 12 mL of 2N H$_2$SO$_4$ stop solution into reservoir and add 100 µL per well with the multichannel pipettor. Tap gently to mix. Read A450: read plate in the plate reader.

GALNS Specific Activity Assay

The GALNS specific activity assay measures the enzymatic activity of GALNS in solution using a GALNS-specific substrate.

Buffers. MilliQ H$_2$O is used for all buffers. Dilution Buffer (DB): for 1 L of DB, dissolve 1.74 mL acetic acid, 0.75 g sodium acetate, 233.6 mg NaCl, 2 mL of 50% TWEEN®-20 and 10 mL of 1% sodium azide into MilliQ H$_2$O, and adjust the pH to 4.0+/−0.5 with 0.1 M NaOH if the pH is less than 3.95 and with 0.1 M acetic acid if the pH is greater than 4.05. The final concentrations are: 19.5 mM acetic acid, 5.5 mM sodium acetate, 1 mM NaCl, 0.1% TWEEN®-20 and 0.01% sodium azide. Phosphate Buffer (PB): for 1 L PB, dissolve 13.9 g NaH$_2$PO$_4$—H$_2$O and 55g NaHPO$_4$-7H$_2$O in MilliQ H$_2$O, and adjust the pH to 7.2. The final concentration is 300 mM NaPi. Stop Buffer (SB): for 1 L SB, dissolve 26.2 g glycine and 46.6 g sodium carbonate in MilliQ H$_2$O, and adjust the pH to 10.6 with NaOH. Assay Buffer (AB): dilute 4MU-Gal-6S stock 1:50 in DB (2 mM final). β-Galactosidase Buffer (βGB): 25 µg/mL β-Galactosidase in 300 mM NaPi, pH 7.2.

Reagents. 4MU-Gal-6S: 100 mM in H$_2$O (Toronto Research Chemicals Cat. #M334480). β-Galactosidase: Sigma G-4155. 4-methylumbelliferone (4MU standard): Sigma M-1381 (10 mM stock in DMSO).

Protocol. Perform serial dilutions of the GALNS enzyme. For purified and formulated GALNS (~1.5 mg/ml), dilute samples 1:10,000 in low protein adhesion microcentrifuge tubes (USA Scientific Cat#1415-2600) containing DB, prior to 1:1 serial dilutions. Place 100 µL of DB in a low protein-binding 96-well plate. In the first row, pipette 100 µL of GALNS sample. Now serially dilute (1:1) down the plate (A-G on 96-well plates). No sample is added to well H (blank) The linear range of this assay is 1-75 ng/mL. Use the same procedure for preparing the 4MU standard curve. Dilute 10 mM 4MU stock in DMSO 1:100 in DB. Start 4MU standard curve by adding 50 µL of 50 µM 4MU in the first well, then serially dilute. Add 50 µL of the substrate diluted in AB (2 mM 4MU-Galactose-6S in DB) to a 96-well fluorescent plate. Pre-incubate substrate for 10 min at 37° C. Add 50 µL of the 100 µL serial dilutions of GALNS and 4MU standards to the 50 µL of substrate in AB. Incubate at 37° C. for 30 min (this first reaction removes the sulfate from the substrate), quench the first reaction and start the second reaction by adding 50 µL of β-Galactosidase (dilute β-galactosidase stock to 25 µg/mL in βGB. Phosphate inhibits GALNS and the increase in pH also stops the GALNS reaction. The resulting pH is now in the optimum pH range of β-galactosidases. Incubate this second reaction for 15 min at 37° C. Ionize released 4MU by adding 100 µL of SB. Read Ex355 Em460 on 96-well fluorescent plate reader. Enzyme activity calculations (at 37° C. in pH 4.0 buffer): 1 unit=µmol 4MU released/min; activity=µmol 4MU/min/mL; specific activity=µmol 4MU/min/mg. Protein concentration calculation: use extinction coefficient of GALNS (1 mg/mL=1.708 Absorbance Units at 280 nm).

Example V

Purification of Human N-Acetylgalactosamine-6-Sulfatase (GALNS)

The objective was to obtain a large quantity of recombinant human N-acetylgalactosamine-6-sulfatase (GALNS). Stably transfected G71 cells co-expressing human SUMF1 and human GALNS were grown under bioreactor culture conditions, and active GALNS enzyme was purified from the cell medium.

Liquid Chromatography Apparatus. Amersham Pharmacia Biotech AKTA explorer 900 system, utilizing Unicorn control software.

Protein Analytical Methods. Standard procedures were followed for SDS-PAGE, COOMASSIE® Blue staining (B 101-02-COOM), Western blotting and Bradford protein assays. The purification runs were assessed by yield of activity, and the purity of the GALNS product was assessed visually by SDS-PAGE. The presence of processed impurities was detected by Western blotting using an anti-GALNS antibody. Protein concentration was measured using a Bradford protein assay. The concentration of the final purified GALNS protein was measured by A$_{280}$ measurement using an extinction coefficient of 1.708.

Chromatography Resins. Blue SEPHAROSE® 6 FF (GE Healthcare, lot #306346) and FRACTOGEL® SE Hi-Cap (Merck KgaA, FC040894449).

GALNS Enzyme Activity Determinations. The GALNS specific activity was determined using a small fluorescent substrate 4-methylumbelliferyl-6-S-GAL (4-MU-6-S-GAL). The GALNS specific activity assay involves a two-step reaction, wherein addition of β-galactosidase is necessary after incubation of GALNS with the substrate for a certain time to release the fluorescent tag. Measurements are made using a fluorescence plate reader.

A 10 DG desalting column (Bio-RAD) was equilibrated with equilibration buffer (EQB, 50 mM NaOAc, 10 mM NaCl, pH 5.8). MilliQ H$_2$O was used for all buffers. Three (3) mL of purified GALNS (0.5-2 mg/mL) was loaded onto the desalting column, eluted and collected in 4 mL aliquots in separate test tubes using EQB. The protein concentration was calculated using the extinction coefficient of GALNS (1 mg/mL=1.708 Absorbance Units at 280 nm).

Desalted GALNS samples were serially diluted (1:1) in dilution buffer (DB, 50 mM NaOAc, 1 mM NaCl, pH 4.0+0.5 mg/mL BSA). The BSA stock was desalted before using by loading 50 mg/mL BSA stock (no more than 5% CV) onto a G25 column previously equilibrated with milliQ H$_2$O. 100 µL of the desalted GALNS sample was pipetted in the first row of a low protein binding 96-well plate, and the serially diluted GALNS samples were pipetted down the plate (rows A-G on 96-well plates). 100 µL of DB was pipetted into the last well (H). The top end of the linear range of this assay is 200 ng/mL, and the linear range is 3-200 ng/mL. The same procedure was performed for preparing the standard curve with 4-methylumbelliferone (4MU) (Sigma M-1381, 10 mM stock in DMSO). 50 µL of the 100 µL serial dilutions of GALNS and 4MU were transferred to a new 96-well fluorescent plate (black bottom plate). 50 µL of 2 mM 4MU-Galactose-6S (in milliQ H$_2$O) was added to the samples to be assayed, and incubated at 37° C. for 30 minutes. This first reaction was quenched, and a second reaction was initiated by adding 50 µL of β-Galactosidase (Sigma G-4155, stock diluted to 12 µg/mL in 300 mM NaPi, pH 7.2), and incubated at 37° C. for 15 minutes. Released 4MU was ionized by adding 100 µL of stop buffer (Glycine/

Carbonate, pH 10.6). The plates were read on 96-well fluorescent plate reader (excitation 355 nm, emission 460 nm). 1 Unit is defined as 1 μmol 4MU released/min, enzyme activity is given in μmol 4MU/min/mL, and specific activity is given in μmol 4MU/min/mg, all at 37° C. in pH 4.0 buffer.

First Purification Process. A first purification process included an ultrafiltration (UF) step followed by a 2-column purification process.

1. Harvest Filtration (HF): the bioreactor material was 0.2 μm sterile filtered.
2. Ultrafiltration (UF): the bioreactor material was concentrated 10-20× by ultrafiltration through a 30 kD SARTOCON® membrane.
3. pH 4.5 Adjust: the concentrated bioreactor material (UF (20×)) was adjusted to pH 4.5 with pH adjust buffer (1.75 M NaOAc, pH 4.0) at room temperature and sterile filtered before loading on a Blue SEPHAROSE® column.
4. Blue SEPHAROSE® 6 Fast Flow (FF): the pH 4.5 adjusted UF (20×) was loaded onto a Blue SEPHAROSE® column and the GALNS protein was eluted as shown in Table 1 and FIG. 9A.

TABLE 1

Blue SEPHAROSE ® 6 Fast Flow Chromatography

| Step | CV* | Buffer |
|---|---|---|
| Equilibration | 5 | 20 mM acetate/phosphate, 50 mM NaCl, pH 4.5 |
| Load |  | UF product, adjusted to pH 4.5, filtered |
| Wash 1 | 4 | 20 mM acetate/phosphate, 50 mM NaCl, pH 4.5 |
| Wash 2 | 8 | 20 mM acetate/phosphate, 50 mM NaCl, pH 6.0 |
| Elution | 8 | 20 mM acetate/phosphate, 100 mM NaCl, pH 7.0 |
| Strip | 5 | 20 mM acetate/phosphate, 1M NaCl, pH 7.0 |
| Sanitization | 4 | 0.1N NaOH, 0.5 hour |
| Regeneration | 5 | H$_2$O |
| Storage | 3 | 20% ETOH |

*CV: column volumes. Flow rate = 92 cm hr$^{-1}$

5. FRACTOGEL® SE Hi-Cap: the eluate from the Blue SEPHAROSE® column was adjusted to pH 4.3 and loaded onto a FRACTOGEL® SE Hi-Cap column and the GALNS protein was eluted as shown in Table 2 and FIG. 9B.

TABLE 2

FRACTOGEL ® SE Hi-Cap Chromatography

| Step | CV* | Buffer |
|---|---|---|
| Equilibration | 5 | 20 mM acetate/phosphate, 50 mM NaCl, pH 4.3 |
| Load |  | Blue SEPHAROSE ® Eluate adjusted to pH 4.3 and diluted 1:1 with MQ water |
| Wash 1 | 5 | 20 mM acetate/phosphate, 50 mM NaCl, pH 5.0 |
| Wash 2 | 5 | 20 mM acetate/phosphate, 50 mM NaCl, pH 5.5 |
| Elution | 20 | 20 mM acetate/phosphate, 50-350 mM NaCl gradient, pH 5.5 |
| Regeneration 1 | 5 | 20 mM acetate/phosphate, 500 mM NaCl, pH 5.5 |
| Regeneration 2 | 5 | 20 mM acetate/phosphate, 50 mM NaCl, pH 4.3 |
| Sanitization | 5 | 0.5N NaOH, 0.5 hour |
| Regeneration 3 | 4 | H$_2$O |
| Storage | 3 | 20% EtOH |

*CV: column volumes. Flow rate = 150 cm hr$^{-1}$

The GALNS protein in the eluate was collected by fractionation, discarding the pre-elution shoulder and post-elution tail.

6. Final UF/HF: the eluate from the FRACTOGEL® SE Hi-CAP column was concentrated by ultrafiltration and sterile filtered as described above.

Formulation. The purified GALNS protein was formulated in 10 mM NaOAc, 1 mM NaH$_2$PO$_4$, 0.005% TWEEN®-80, pH 5.5.

Figure 8:
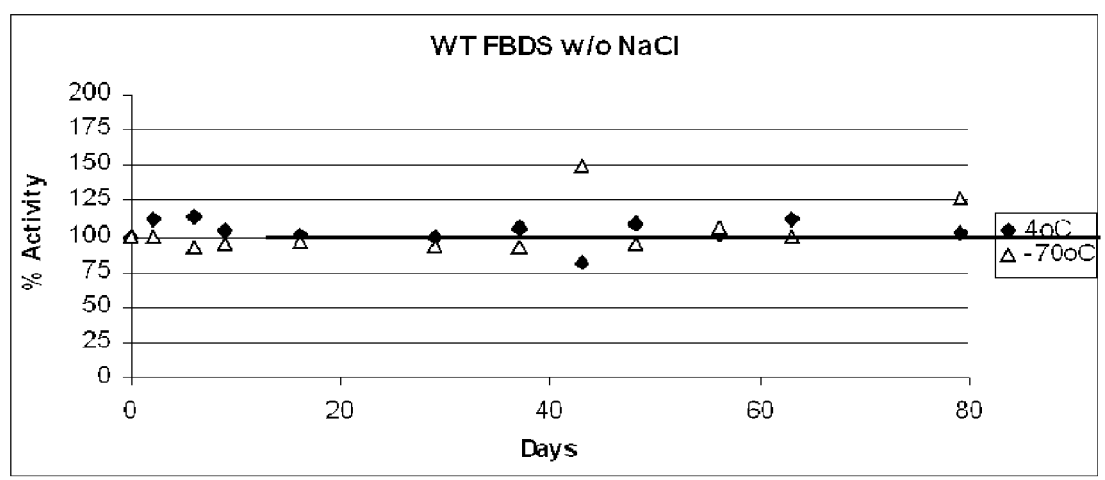
FIG. 8 shows the stability of purified human N-acetylgalactosamine-6-sulfatase (GALNS) enzyme activity upon storage at 4° C. (diamonds) or at −70° C. (triangles).

Stability Studies. Stability of the final formulated purified GALNS was monitored at 4° C. and −70° C. as a function of time by storing small aliquots of the GALNS samples at the respective temperatures. At certain time points, aliquots of frozen samples were quickly thawed in a 37° C. waterbath before activity measurements. FIG. 8 shows that the purified GALNS was stable at 4° C. and −70° C. over a period of up to at least 79 days in the formulation buffer.

First Purification Process Results. Table 3 shows the purification yields for three preparations of GALNS protein produced from G71S clone 4 in a suspension culture bioreactor. Purity was estimated visually by SDS-PAGE to be about 95% in all cases.

TABLE 3

Human N-Acetylgalactosamine-6-Sulfatase (GALNS) Purification Yields from G71S Clone 4 from WAVE Reactor

| Steps | Yield | | | | Std Dev |
|---|---|---|---|---|---|
|  | Prep 1 | Prep 2 | Prep 3 | Average |  |
| UF | N/A | 100 | 100 | 100 | 0 |
| Blue SEPHAROSE ® 6 FF | 93 | 103 | 101 | 99 | 5.3 |
| SE Hi-Cap | 90 | 87 | 90 | 89 | 1.7 |

FIG. 9 shows an SDS-PAGE of the GALNS protein separated by (A) Blue SEPHAROSE® 6 Fast Flow chromatography followed by (B) FRACTOGEL® SE Hi-CAP chromatography. The gels were stained with COOMASSIE® Blue (left) or anti-GALNS antibody (right). For the Western blots, the anti-GALNS rabbit antibody was diluted to 1:5000, and the secondary antibody was an anti-alkaline phosphatase rabbit antibody. The GALNS protein has an apparent molecular weight of ~55-60 kDa on SDS-PAGE, consistent with expected size of the secreted pre-processed (precursor) form of the enzyme lacking the 26 amino acid residue signal peptide, and also lacking the cleavage after position 325.

N-Terminus Characterization. The N-terminus of the purified GALNS protein was determined by LC/MS. The N-terminal sequence was APQPPN, which corresponds to the predicted N-terminus of the secreted form of GALNS lacking the 26 amino acid residue signal peptide (compare the human GALNS polypeptide sequences in FIG. 4 and FIG. 5).

Second Purification Process. A second purification process included an ultrafiltration/diafiltration (UF/DF) step followed by a 3-column purification process.

1. Ultrafiltration (UF/DF): the bioreactor material was concentrated 20× by ultrafiltration/diafiltration through a 30 kD SARTOCON® membrane at pH 5.5.
2. pH 4.5 Adjust: the concentrated bioreactor material (UF/DF (20×)) was adjusted to pH 4.5 with pH adjust buffer (1.75 M NaOAc, pH 4.0) at room temperature and sterile filtered before loading on a FRACTOGEL® EMD SE Hi-Cap column.
3. FRACTOGEL® EMD SE Hi-Cap: the pH 4.5 adjusted UF/DF (20×) was loaded onto a FRACTOGEL® EMD SE Hi-Cap column, washed sequentially with 10 mM acetate/phosphate, 50 mM NaCl, pH 4.5 and 10 mM acetate/phosphate, 50 mM NaCl, pH 5.0, and the GALNS protein was eluted with 10 mM acetate/phosphate, 140 mM NaCl, pH 5.0.
5. Zn-chelating SEPHAROSE® FF: the eluate from the FRACTOGEL® EMD SE Hi-Cap column was adjusted to 500 mM NaCl, pH 7.0 and loaded onto a Zn-chelating SEPHAROSE® FF (Zn-IMAC) column, washed with 10 mM acetate/phosphate, 125 mM NaCl, 10 mM imidazole, pH 7.0, and the GALNS protein was eluted with 10 mM acetate/phosphate, 125 mM NaCl, 90 mM imidazole, pH 7.0.

6. pH 3.5 Adjust: the eluate from the Zn-chelating SEPHAROSE® FF column containing the GALNS protein was adjusted to pH 3.5 for low pH viral inactivation and then adjusted to 10 mM acetate/phosphate, 2 M NaCl, pH 5.0.

7. TOYOPEARL® Butyl 650M: the low pH adjusted eluate from the Zn-chelating SEPHAROSE® FF column, was loaded onto a TOYOPEARL® Butyl 650M column, washed with 10 mM acetate/phosphate, 2 M NaCl, pH 5.0., and the GALNS protein was eluted with 10 mM acetate/phosphate, 0.7 M NaCl, pH 5.0.

8. Final UF/HF: the eluate from the TOYOPEARL® Butyl 650M eluate was ultra-filtered and dia-filtered in 20 mM acetate, 1 mM phosphate, 150 mM NaCl, pH 5.5.

Formulation. The purified GALNS protein was formulated in 10 mM NaOAc/HOAc, 1 mM $NaH_2PO_4$, 150 mM NaCl, 0.01% TWEEN®-20, pH 5.5.

Second Purification Process Results. Table 4 shows the recovery for GALNS protein produced from G71S clone C2 in a suspension culture bioreactor using the second purification process. Purity of the formulated GALNS enzyme (i.e., precursor and mature or processed forms together) was about 98% as determined by C3 RP-HPLC. The percentage of the precursor form of the GALNS enzyme was about 85% as determined by SDS-capillary gel electrophoresis.

TABLE 4

Human N-Acetylgalactosamine-6-Sulfatase (GALNS) Recovery for G71S Clone C2

| Process Step | Recovery (%) |
|---|---|
| pH Adjust | 96 |
| FRACTOGEL ® SE Hi-Cap Column | 98 |
| Zn-IMAC Column | 89 |
| Low pH Viral Inactivation | 89 |
| TOYOPEARL ® Butyl 650M Column | 99 |
| Formulation | 99 |
| Overall | 70 |

Figure 10:
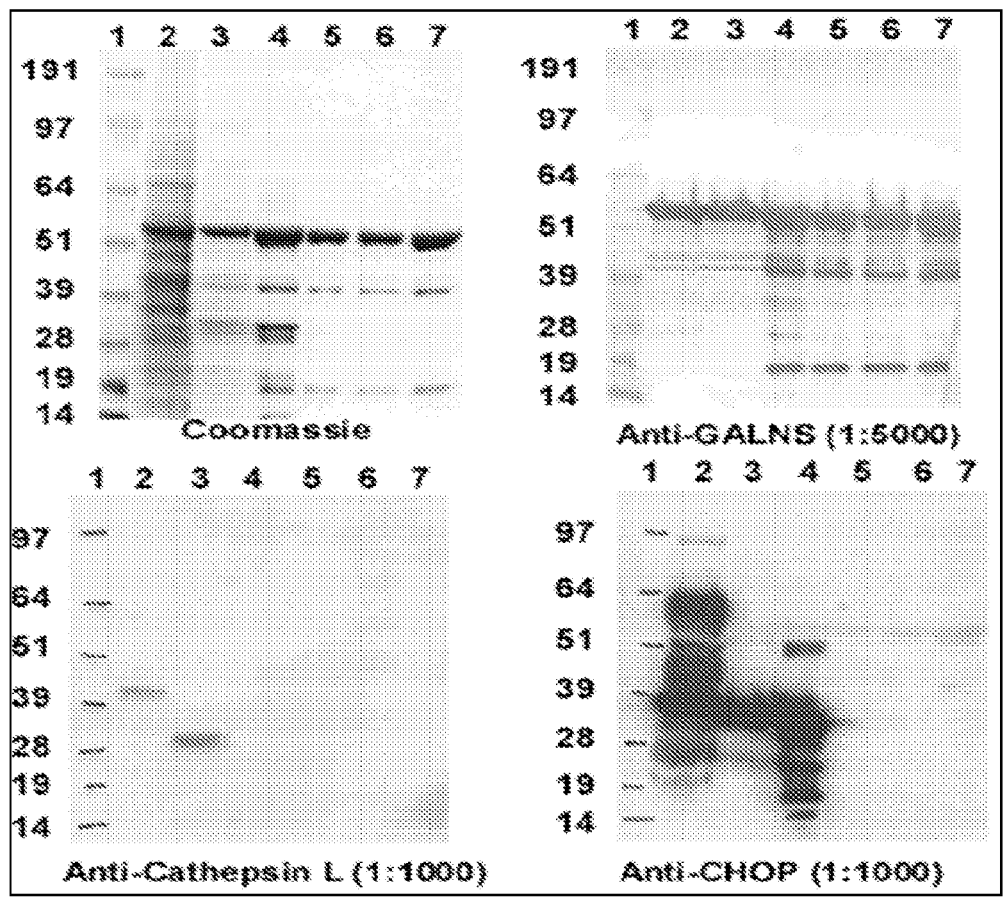
FIG. 10 shows the purification of human N-acetylgalactosamine-6-sulfatase (GALNS) by ultrafiltration/diafiltration (UF/DF), FRACTOGEL® SE Hi-Cap chromatography, Zn-chelating SEPHAROSE® chromatography and TOYO-PEARL® Butyl 650M chromatography. Purity is determined by COOMASSIE® Blue staining of SDS-PAGE (top left) and by Western blotting using an anti-GALNS antibody (top right), an anti-Cathepsin L antibody (bottom left) and an anti-CHOP (Chinese Hamster Ovary cell proteins (bottom right).

FIG. 10 shows an SDS-PAGE of the GALNS enzyme separated by unitrafiltration/diafiltration (UF/DF), FRACTOGEL® SE Hi-CAP chromatography, Zn-chelatng SEPHAROSE® FF chromatography and TOYOPEARL® Butyl 650M chromatography. The gels were stained with COOMASSIE® Blue (top left), anti-GALNS antibody (top right), anti-Cathepsin L (bottom left) and anti-CHO proteins (CHOP, bottom right). For the Western blots, the anti-GALNS rabbit polyclonal antibody was diluted to 1:5000, and the secondary antibody was an anti-rabbit AP conjugate; the anti-Cathepsin L goat polyclonal antibody was diluted to 1:1000, and the secondary antibody was an anti-goat HRP conjugate; and the anti-CHOP rabbit polyclonal antibody was diluted to 1:1000, and the secondary antibody was an anti-rabbit HRP conjugate. The precursor GALNS enzyme has an apparent molecular weight of ~55-60 kDa on SDS-PAGE, and the mature or processed forms of GALNS enzyme have apparent molecular weights of ~39 kDa and ~19 kDa on SDS-PAGE.

Summary of First Purification Process. The GALNS enzyme was purified using a purification train that had been modified from a standard train (see Table 5). Bioreactor harvest material was 0.2 µm sterile filtered and kept at 4° C. before loading onto the Blue-SEPHAROSE® capture column. The filtered bioreactor material was either loaded directly or concentrated up to 15× by ultrafiltration. Modification of the purification train was necessary because the downstream purification steps, SP SEPHAROSE® chromatography followed by Phenyl SEPHAROSE® chromatography, did not yield sufficiently pure GALNS. Using SE Hi-Cap chromatography as a replacement for the two downstream purification columns resulted in a 2-column purification process, with the purity of final material significantly improved, and the overall GALNS recovery increased significantly from to ~22% to ~80%. The purity of the GALNS enzyme (consisting essentially of the precursor form, see FIG. 9), as determined by C4-RP chromatography, was roughly estimated at >95%, and the purified GALNS enzyme remained stable in formulation buffer for more than 79 days at both 4° C. and at −70° C.

TABLE 5

First Human N-Acetylgalactosamine-6-Sulfatase (GALNS) Purification Train

| Step | Normal Process | Modified Process |
|---|---|---|
| 1 | HF (1X) | HF (1X) |
| 2* | UF (5X) | UF (15X) |
| 3 | pH 4.5 Adjust | pH 4.5 Adjust |
| 4 | Blue--SEPHAROSE ® 6 FF | Blue-SEPHAROSE ® 6 FF |
| 5 | SP SEPHAROSE ® | SE Hi-Cap |
| 6 | Phenyl SEPHAROSE ® Hi-Sub | Final UF/DF |
| 7 | Final UF/DF | |

*This step is optional.

Summary of Second Purification Process. The GALNS enzyme was also purified using a second purification train (see Table 6). The overall GALNS recovery was about 70% and the purity of the GALNS enzyme (including both precursor and mature or processed forms, see FIG. 10), as determined by C4-RP chromatography, was roughly estimated to be about 97%.

TABLE 6

Second Human N-Acetylgalactosamine-6-Sulfatase (GALNS) Purification Train

| Step | Process |
|---|---|
| 1 | HF (1X) |
| 2 | UF/DF (20X) |
| 3 | pH 4.5 Adjust |
| 4 | SE Hi-Cap |
| 5 | Zn-chelating SEPHAROSE ® |
| 6 | pH 3.5 Adjust |
| 7 | TOYOPEARL ® Butyl 650M |
| 8 | Final UF/DF |

These assays indicate that the protocols described above for preparing recombinant lysosomal sulfatase enzymes provide an efficient method for production of large quantities of highly purified enzyme, in particular the secreted pre-processed (precursor) form of human N-acetylgalactosamine-6-sulfatase (GALNS).

Example VI

Purification of Human N-Acetylgalactosamine-6-Sulfatase (GALNS) with Minimal Clipping Control of proteolytic digestion of recombinant enzymes is a concern in the production and formulation of protein-based therapeutics. The objective was to obtain a large quantity of recombinant human N-acetylgalactosamine-6-sulfatase (GALNS) in the secreted pre-processed (precursor) form. A production process was developed that would allow for the large scale manufacturing of human GALNS with minimal clipping from proteases, in particular, cathepsin L.

As used herein, "minimal clipping" means that the GALNS is at least 98%, at least 98.5%, at least 99% or at least 99.5% intact in final purified formulations, as judged by SDS-PAGE under reducing conditions followed by COOMASSIE® Blue staining or by SDS-capillary gel electrophoresis (SDS-CGE).

During the development of a production process for large scale manufacturing of GALNS, it was found that the ~55 kDa secreted precursor form of the enzyme was susceptible to proteolytic degradation by proteases, in particular, cathepsin L, which is active at acidic pH. Protease degradation of GALNS generates a mature, clipped form of GALNS, which can be viewed as two bands at ~40 kDa and ~19 kDa on SDS-PAGE under reducing conditions. This proteolytic clipping was exacerbated by the low pH (i.e., 4.5 to 5.0) required for the cation exchange column capture step. This pH range provided conditions that were favorable for activity of acidic proteases, such as cathepsins, present in the cell culture harvest.

Changes were made in the GALNS recovery and purification process to minimize the presence and/or activity of proteases that can clip GALNS secreted into the cell culture medium.

Figure 11:
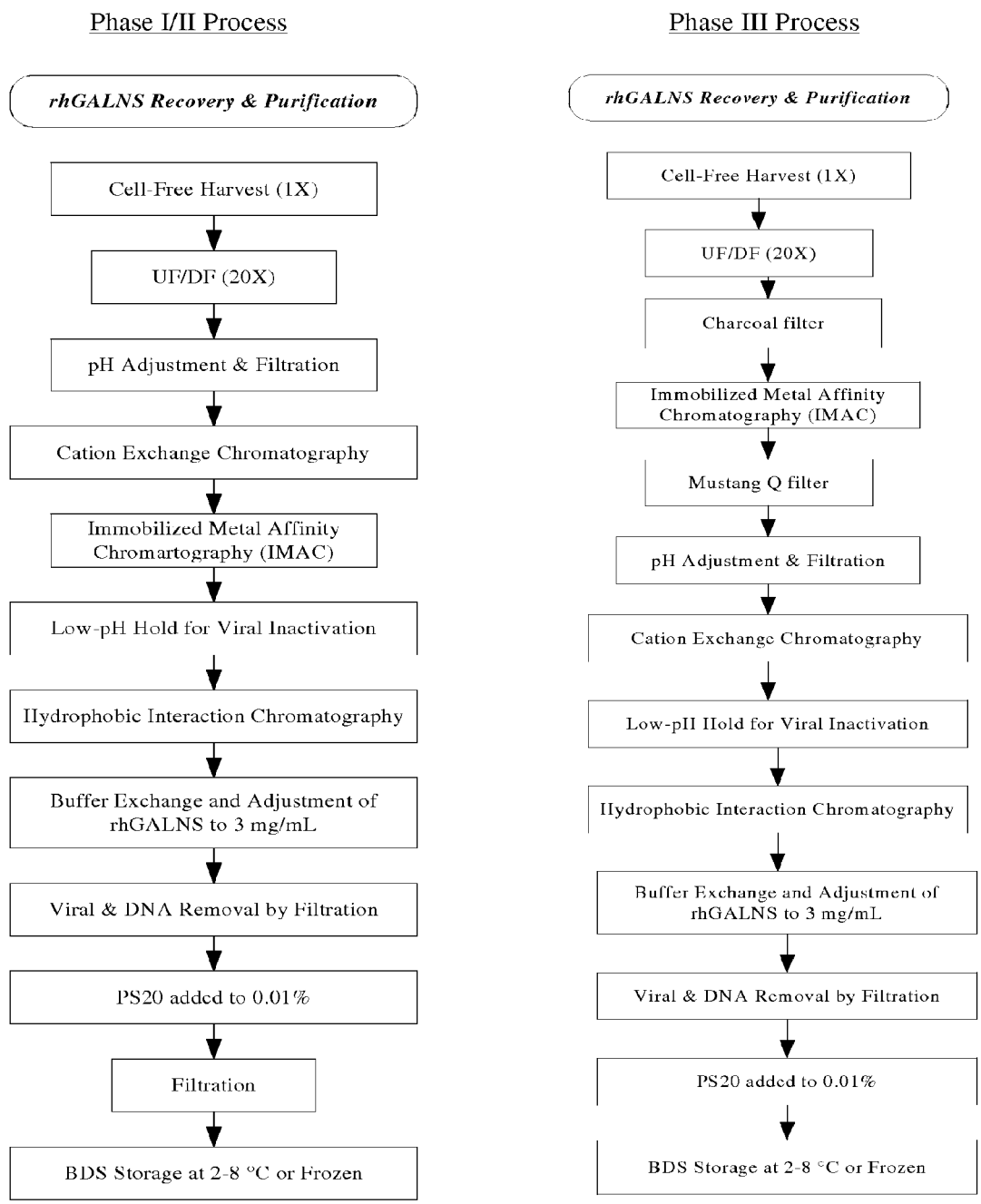
FIG. 11 shows the process flow diagrams for the human N-acetylgalactosamine-6-sulfatase (GALNS) recovery and purification process used for the Phase I/II process (left) and the Phase III process (right).

Flow charts depicting exemplary recovery and purification processes for large scale manufacturing of GALNS are shown in FIG. 11. The process on the left shows the recovery and purification process used in the Phase I/II process, similar to the purification train described above in Example V, which results in a variable amount of clipping, ranging from ~6-30% of the peptide chain due to activation of cathepsin L, as determined by SDS-PAGE run under reducing conditions followed by COOMASSIE® Blue staining (see FIG. 12, lane 3), or ranging from 65.3% to 93.7% intact precursor form of GALNS, as judged by SDS-CGE (see Table 8). The SDS-PAGE method provides visual, but more qualitative, information on protein degradation, whereas the SDS-CGE method provides more quantitative information regarding the % intact protein present in the final purified formulations.

The process on the right in FIG. 11 shows the recovery and purification process used in the Phase III process, which results in minimal clipping, ranging from 98% to 99.6% intact precursor form of GALNS, as judged by SDS-PAGE run under reducing conditions followed by COOMASSIE® Blue staining (see FIG. 12, lane 5) or by SDS-CGE (see Table 8).

Overview of Process Changes. To reduce the extent and variability of GALNS clipping, two factors were taken into account: (i) the proteases are significantly less active at neutral pH; and (ii) both the cation exchange chromatography and immobilized metal affinity chromatography (IMAC) steps separate proteases from GALNS. The Phase III process (see FIG. 11, right) exploits these factors and helps reduce clipping of GALNS during the purification procedure. This was achieved by switching the order of the first two column steps, with capture on the Zn-IMAC column at pH 6.5 to 7.0. This switching of the first two columns also made it convenient to collect and store the cell culture harvests at a higher pH (i.e., pH 6.5) compared to the more acidic pH (i.e., pH 5.5) that was used in the Phase I/II process (see FIG. 11, left). Storage of the cell-free harvest at pH 6.5 reduces the possibility of activation of proteases, e.g., cathepsins, present in the cell culture fluid, thereby preventing or reducing the clipping of GALNS.

Phase III Process. Each of the steps in an exemplary Phase III process recovery and purification for GALNS is summarized below.

1. Cell-Free Harvest (1×). Stably transfected G71 cells co-expressing human SUMF1 and human GALNS were grown under bioreactor culture conditions as described in Example III. The bioreactor material (i.e., cell culture fluid) containing the GALNS was collected at pH 6.5, and filtered using a filtration train of CUNO 30SP02A, followed by CUNO 90ZA08A, and a 0.2 µm CUNO BioAssure filter.

2. UF/DF (20×). The cell culture fluid was ultrafiltered/diafiltered (UF/DF) into 10 mM phosphate/acetate, 50 mM NaCl, pH 6.5 at a conductivity of ≤7 mS/cm. The UF/DF step was performed using SARTOCON® 30 kDa HYDROSART® cassettes. The cell culture fluid was concentrated 20×. For comparison, the Phase I/II process UF/DF step was performed at pH 5.5. The higher pH in the Phase III process reduces the possibility of clipping of GALNS by proteases present in the cell-free harvest.

3. Charcoal Filter. The UF/DF (20×) material was filtered through a ZETA PLUS® R55 Activated Carbon (Z1274) and then sterile filtered using a 0.2 µm filter prior to storage at 2-8° C. The charcoal filter significantly reduced pressure upon loading the subsequent Zn-IMAC column.

4. Immobilized Metal Affinity Chromatography (IMAC). A Zn-immobilized metal affinity chromatography (Zn-IMAC) column was equilibrated in 10 mM phosphate/acetate, 500 mM NaCl, pH 7.0, and loaded at a conductivity of ~55±5 mS/cm with the charcoal filtered UF/DF (20×) material at pH 7.0±0.1 by addition of 50 mM phosphate buffer, pH 9.2 containing 2.5 M NaCl. The loaded column was washed with 10 mM phosphate/acetate, 500 mM NaCl, pH 7.0, followed by 10 mM phosphate/acetate,125 mM NaCl, pH 7.0 (buffer A). The GALNS was eluted from the column with a mixture of 70% buffer A and 30% buffer B (10 mM phosphate/acetate, 125 mM NaCl, 300 mM imidazole, pH 7.0).

5. MUSTANG® Q Filter. The Zn-IMAC column eluate was adjusted to a conductivity of ~6.0±0.5 mS/cm at pH 7.0, and loaded on a MUSTANG® Q filter to remove viruses.

6. pH Adjustment & Filtration. The MUSTANG® Q filtrate was adjusted to pH 4.5±0.1, filtered using a CUNO 60ZA filter followed by a 0.2 µm inline filter, and then loaded on a cation exchange column.

7. Cation Exchange Chromatography. A FRACTOGEL® SE HiCap cation exchange column was equilibrated in 10 mM phosphate/acetate, 50 mM NaCl, pH 4.5, and loaded with the filtered MUSTANG® Q filtrate adjusted to pH 4.5±0.1 at a conductivity of ≤7 mS/cm. The loaded column was washed with 10 mM phosphate/acetate, 50 mM NaCl, pH 4.5, followed by an 80%:20% mixture of 10 mM phosphate/acetate, pH 5.0 (buffer A) and 10 mM phosphate/acetate, 250 mM NaCl, pH 5.0 (buffer B). The GALNS was eluted from the column with a linear gradient of 20 to 75% buffer B in 80% to 25% buffer A (i.e., 50 to 190 mM NaCl).

8. Low-pH Hold for Viral Inactivation. The FRACTO-GEL® SE HiCap eluate was acidified to pH 3.5±0.1 for viral inactivation by addition of 0.2 M citrate buffer, pH 3.4, held at the low pH for ~1 hour, readjusted to pH 5.0±0.1 by addition of 0.2 M citrate buffer, pH 6.0, and then loaded on a hydrophobic interaction chromatography (HIC) polishing column.

9. Hydrophobic Interaction Chromatography (HIC). A TOYOPEARL® Butyl 650M HIC column was equilibrated in 10 mM phosphate/acetate, 2 M NaCl, pH 5.0, and loaded with the low-pH viral inactivated FRACTOGEL® SE HiCap eluate adjusted to 2 M NaCl, pH 5.0. The loaded column was washed with 10 mM phosphate/acetate, 2 M NaCl, pH 5.0 (buffer A). The GALNS was eluted from the column with a mixture of 35% buffer A and 65% buffer B (10 mM phosphate/acetate, pH 5.0).

10. Buffer Exchange & Adjustment of rhGALNS to 3 mg/mL. The TOYOPEARL® Butyl 650M HIC eluate was buffer exchanged into 20 mM acetate, 50 mM phosphate, 30 mM arginine, 2% (v/v) sorbitol, pH 5.4, and then adjusted to a final GALNS concentration of 3 mg/mL in the same buffer.

11. Viral & DNA Removal by Filtration. The buffer exchanged TOYOPEARL® Butyl 650M HIC eluate was filtered to remove any residual viruses and DNA using a viral filter (DV20) and a DNA filter (MUSTANG® Q).

12. PS20 Added to 0.01%. The virus and DNA filtered, buffer exchanged TOYOPEARL® Butyl 650M HIC eluate was adjusted to 0.01% (v/v) polysorbate 20 (PS20 or TWEEN®-20).

13. BDS Storage at 2-8° C. or Frozen. The final formulation of purified GALNS, i.e., the Bulk Drug Substance (BDS), was stored at 2-8° C. or frozen.

Results. As seen in the SDS-PAGE results (see FIG. 12, lane 5), the apparent molecular mass of the main band is ~55 kDa, consistent with the expected value for the GALNS monomer. The bands migrating at the apparent molecular masses of ~40 kDa and ~19 kDa in lot#AP400802, which was generated using the Phase I/II process (lane 3), are the degradation products of GALNS resulting from proteolytic clipping between Q348 and G349. This clipping is greatly reduced in lot#BMN110-0110-001, which was generated using the Phase III process (lane 5). There is a minor band in both preparations migrating slightly slower than the ~40 kDa cleavage product.

Overview of Further Process Changes. A modified Phase III process was developed to address certain challenges: (i) the formation of a precipitate in the concentrated harvest; (ii) the loss of GALNS at the Zn-IMAC capture step; (iii) the loss of GALNS in the wash fraction during the TOYOPEARL® Butyl step; and (iv) the presence of high levels of CHOP impurities in the eluate of the TOYOPEARL® Butyl step.

Modified Phase III Process. Each of the steps in an exemplary Phase III process recovery and purification for GALNS is summarized below.

1. Cell-Free Harvest (1×). Stably transfected G71 cells co-expressing human SUMF1 and human GALNS were grown under bioreactor culture conditions as described in Example III. The bioreactor material (i.e., cell culture fluid) containing the GALNS was collected at pH 6.5, and filtered using a filtration train of Millipore DOHC, followed by Millipore XOHC, and a 0.2 μm Millipore SHC filter.

2. UF/DF (20×). The cell culture fluid was ultrafiltered/diafiltered (UF/DF) into 10 mM phosphate/acetate, 50 mM NaCl, pH 6.5 at a conductivity of ≤7 mS/cm. The UF/DF step was performed using SARTOCON® 30 kDa HYDROSART® cassettes. The cell culture fluid was concentrated 20×.

3. Charcoal Filter. The UF/DF (20×) material was filtered through a ZETA PLUS® R55 Activated Carbon (Z1274) and then sterile filtered using a 0.2 μm filter prior to storage at 2-8° C.

4. Immobilized Metal Affinity Chromatography (IMAC). A Zn-immobilized metal affinity chromatography (Zn-IMAC) column was rinsed with 50 mM acetate buffer, pH 5.0, charged with 50 mM $ZnSO_4$, rinsed with 50 mM acetate buffer, pH 5.0, and then equilibrated in 10 mM phosphate/acetate, 500 mM NaCl, pH 7.0, containing 5 mM imidazole. The equilibrated Zn-IMAC was loaded at a conductivity of ~50±5 mS/cm with the charcoal filtered UF/DF (20×) material at pH 7.0±0.1 by blending in line with 50 mM phosphate buffer, pH 9.2±0.1 containing 2.5 M NaCl in a 75:25 (v/v) ratio during loading the Zn-IMAC column. The loaded column was washed with 10 mM phosphate/acetate, 500 mM NaCl, pH 7.0, followed by 10 mM phosphate/acetate, 125 mM NaCl, pH 7.0 (buffer A). The GALNS was eluted from the column with a mixture of 70% buffer A and 30% buffer B (10 mM phosphate/acetate, 125 mM NaCl, 300 mM imidazole, pH 7.0).

5. pH Adjustment & Filtration. The Zn-IMAC column eluate was adjusted to pH 4.5±0.1 with 1.75 M acetate, pH 4.0, and then filtered using a Millipore COHC filter. The filtered material was blended in line with 10 mM phosphate/acetate, pH 4.5 in a 30:70 (v/v) ratio during loading of the cation exchange column.

6. Cation Exchange Chromatography. A FRACTOGEL® SE HiCap cation exchange column was equilibrated in 10 mM phosphate/acetate, 50 mM NaCl, pH 4.5, and loaded with the pH 4.5-adjusted and filtered Zn-IMAC column eluate at a conductivity of <7 mS/cm. The loaded column was washed with 10 mM phosphate/acetate, 50 mM NaCl, pH 4.5, followed by an 80%:20% mixture of 10 mM phosphate/acetate, pH 5.0 (buffer A) and 10 mM phosphate/acetate, 250 mM NaCl, pH 5.0 (buffer B). The GALNS was eluted from the column with a linear gradient of 20% to 75% buffer B in 80% to 25% buffer A (i.e., 50 to 190 mM NaCl).

7. Low-pH Hold for Viral Inactivation. The FRACTOGEL® SE HiCap eluate was acidified to pH 3.5±0.1 for viral inactivation by addition of 0.4 M citrate buffer, pH 3.4, held at the low pH for ~1 hour (at a temperature of 12-23° C.), readjusted to pH 5.0±0.1 by addition of 0.4 M citrate buffer, pH 6.0, blended with a 10 mM phosphate/acetate buffer, pH 5, containing 5 M NaCl to achieve a final concentration of 2 M NaCl, and then filtered through a 0.2 μm filter before loading on a hydrophobic interaction chromatography (HIC) polishing column.

8. Hydrophobic Interaction Chromatography (HIC). A TOYOPEARL® Butyl 650M HIC column was equilibrated in 10 mM phosphate/acetate, 2 M NaCl, pH 4.4, and loaded with the filtered, low-pH viral inactivated FRACTOGEL® SE HiCap eluate adjusted to 2 M NaCl, pH 4.3-4.4. The loaded column was washed with 10 mM phosphate/acetate, 2 M NaCl, pH 4.4, followed by 10 mM phosphate/acetate, 2.5 M NaCl, pH 5.0 (buffer A). The GALNS was eluted from the column with a linear gradient of 100% to 32% buffer A in 0 to 68% buffer B (10 mM phosphate/acetate, pH 5.0) (i.e., 2.5 to 0.8 M NaCl) followed by a mixture of 32% buffer A and 68% buffer B (i.e., 0.8 M NaCl).

9. Buffer Exchange, DNA &Virus Removal by Filtration, & Adjustment of rhGALNS to 3 mg/mL. The TOYOPEARL® Butyl 650M HIC eluate was buffer exchanged into 20 mM sodium acetate, 50 mM sodium phosphate, 30 mM arginine-HCl, 2% (w/v) sorbitol, pH 5.4. The buffer exchanged TOYOPEARL® Butyl 650M HIC eluate was filtered to remove any residual DNA and viruses using a DNA filter (MUSTANG® Q) and a viral filter (DV20). The filtered, buffer exchanged TOYOPEARL® Butyl 650M HIC eluate was then adjusted to a final GALNS concentration of 3 mg/mL in the same buffer as above.

10. PS20 Added to 0.01%. The DNA and virus filtered, buffer exchanged TOYOPEARL® Butyl 650M HIC eluate was adjusted to 0.01% (v/v) polysorbate 20 (PS20 or TWEEN®-20).

11. BDS Storage at 2-8° C. or Frozen. The final formulation of purified GALNS, i.e., the Bulk Drug Substance (BDS), was passed through a 0.2 µm Millipak 200 filter into the final storage container and stored in bags at 2-8° C. or frozen.

Results. Following this modified Phase III process, binding of GALNS to the Zn-IMAC and TOYOPEARL® Butyl columns is improved, and CHOP impurities in the TOYOPEARL® Butyl eluate are reduced. The GALNS purified by this modified Phase III process is comparable in all of the properties tested (e.g., those in Table 7 below) to the enzyme purified by the Phase III process described above.

Characterization of rhGALNS Made by the Phase III Recovery & Purification Process. GALNS purified using the Phase III process was compared to the enzyme purified by the Phase I/II process. Characterization results are given in Table 7. Although both GALNS preparations looked comparable in all of the properties tested, the enzyme purified by the Phase III process showed significantly less clipping compared to the one purified by the Phase I/II process.

TABLE 7

Comparison of GALNS Purified by the Phase I/II and Phase III Processes

| Property | Assay Method | TPB050109 (Phase III Process) | AP400802 (Phase I/II Process) |
|---|---|---|---|
| Specific activity | Fluorogenic substrate | 10.2 U/mg | 13.9 U/mg |
| Glycosylation profile | CZE | 35.9% BPM7 | 34.9% BPM7 |
| Clipping | SDS-CGE | 98.7% intact | 73.2% intact |
| Size variants | SEC-HPLC | 98.9% intact** | 99.9% intact |
| UV impurities | RP-HPLC | 99.5% pure | 99.7% pure |
| CHOP* | ELISA | <33 ppm | 46 ppm |

*CHOP: Chinese hamster ovary host cell protein contaminants
**SEC-HPLC data for other rhGALNS lots purified from material obtained from the same 200L cMFG reactor using the Phase III process showed >99% intact protein Table 8 compares the percent intact GALNS using the SDS-CGE method in the final purified formulation in lots that were prepared using either the Phase I/II process (65.3-93.7%) or the Phase III process (98-99.6%). The values obtained here support the results obtained from the SDS-PAGE method and show that the extent of clipping is significantly reduced as a result of the modifications made to the purification process.

TABLE 8

Comparison of % Intact GALNS Purified by the Phase I/II and Phase III Processes (by SDS-CGE)

| GALNS Lot # | Process Used | % Intact GALNS |
|---|---|---|
| 11333P53 | Phase I/II | 82.7% |
| 11333P71 | Phase I/II | 85.6% |
| 11333P79 | Phase I/II | 93.7% |

TABLE 8-continued

Comparison of % Intact GALNS Purified by the Phase I/II and Phase III Processes (by SDS-CGE)

| GALNS Lot # | Process Used | % Intact GALNS |
|---|---|---|
| 11333P90 | Phase I/II | 82.6% |
| 11428P15 | Phase I/II | 80.1% |
| NP400801 | Phase I/II | 65.3% |
| AP400802 | Phase I/II | 73.6% |
| AP400803 | Phase I/II | 78.5% |
| AP400804 | Phase I/II | 82.9% |
| P400902 | Phase III | 98% |
| 11615P56 | Phase III | 98.5% |
| 11615P71 | Phase III | 98.4% |
| 11615P78 | Phase III | 98.9% |
| 11615P81 | Phase III | 98.1% |
| 11780P15 | Phase III | 99.6% |

These assays indicate that the protocol described above for preparing recombinant lysosomal sulfatase enzymes with minimal clipping provide an efficient method for production of large quantities of highly purified enzyme, in particular the secreted pre-processed (precursor) form of human N-acetylgalactosamine-6-sulfatase (GALNS).

Example VII

Characterization of Purified Human N-Acetylgalactosamine-6-Sulfatase (GALNS)

The G71 cell lines produce proteins (e.g., lysosomal enzymes) with greater levels of high-mannose phosphorylation than is noted in an average mammalian cell line, and a correspondingly lower level of unphosphorylated high-mannose oligosaccharides. A lysosomal sulfatase enzyme (e.g., recombinant human N-acetylgalactosamine-6-sulfatase (GALNS)), comprising a high level of bis-phosphorylated high-mannose oligosaccharides, as defined herein, is compared to molecules obtained in Canfield et al., U.S. Pat. No. 6,537,785, which do not comprise complex oligosaccharides, and exhibit only high mannose oligosaccharides.

To determine levels of unphosphorylated high-mannose on a lysosomal sulfatase enzyme, one of skill in the art can use exoglycosidase sequencing of released oligosaccharides ("FACE sequencing"), to pinpoint the percentages of unphosphorylated high-mannose oligosaccharide chains. On a normal lot-release FACE profiling gel, unphosphorylated high mannose co-migrates with particular complex oligosaccharides (e.g., oligomannose 6 and fully sialylated biantennary complex). Unphosphorylated high mannose is then differentiated from the other oligosaccharides by enzymatic sequencing.

To determine if the purified lysosomal sulfatase enzyme (e.g., recombinant human N-acetylgalactosamine-6-sulfatase (GALNS)) expressed in G71S cells exhibits increased phosphorylation, the level of mannose-6-phosphate (M6P) on the lysosomal sulfatase enzyme was determined, as well as the enzyme's ability to bind to the M6P receptor (MPR).

Recombinant human GALNS enzyme, expressed in G71S cells and purified, was analyzed by fluorescence assisted carbohydrate electrophoresis (FACE) and by chromatography on MPR-SEPHAROSE® resin. The FACE system uses polyacrylamide gel electrophoresis to separate, quantify, and determine the sequence of oligosaccharides released from glycoproteins. The relative intensity of the oligomannose 7 bis-phosphate (O7P) band on FACE (Hague et al., *Electrophoresis* 19(15): 2612-20, 1998) and the percent activity retained on the MPR column (Cacia et al., *Biochemistry* 37(43): 15154-61, 1998) give reliable measures of phosphorylation level per mole of protein.

Specific Activity. The specific activity of recombinant human N-acetylgalactosamine-6-sulfatase (GALNS) was determined using a small fluorescent substrate 4-methylumbelliferyl-6-S-GAL (4MU-Gal-6S) at 37° C. Using this assay, the specific activity of the purified GALNS was 165 μmol/min/mg (0.165 U/mg).

Human Serum Stability. The ex vivo serum stability of the GALNS was determined. Human serum (Sigma H-4522) was filter sterilized through a 0.2 μm PES filter, and 4 mL of the filter sterilized human serum was pre-incubated in a T-25 cell culture flask for 1 hour at 37° C. in an atmosphere of 10% $CO_2$ (pH at this point is 7.4±0.1). 0.4 mL of desalted, purified GALNS (2 mg/mL purified GALNS was desalted into PBS using Bio-RAD 10DG columns) was added to the pre-incubated human serum, or a PBS control containing 0.5 mg/L BSA. 100 μL samples were withdrawn at designated time points (e.g., 0, 1, 3.5, 7.5 and 26 hours) and added to 900 mL of quench buffer (QB, 50 mM NaOAc, pH 5.6+150 mM NaCl+0.5 mg/mL BSA+0.001% TWEEN®-80). Samples were stored at 4° C. until ready for measuring GALNS enzyme activity.

The GALNS enzyme activity was measured using the enzyme capture activity ELISA. By extrapolating the exponential decay curve of % residual GALNS enzyme activity, the ex vivo serum half-life of the purified GALNS was estimated to be 217 hours.

Uptake into Synoviocytes (Chrondrocytes). The ability of GALNS to be taken up into synoviocytes (chrondrocytes) was determined.

Chondrocytes (ATCC Number CRL-1832) are cultured in growth media (Ham's F12+10% FBS) at 37° C. in 5% $CO_2$ in 12-well dishes. The analysis of uptake of three samples requires 4×12 well plates. The purified GALNS samples and a GALNS reference were diluted to 1 μM in acPBS/BSA (acidic PBS+200 μg/mL BSA). From the 1 μM stocks, uptake dilution curves for GALNS samples and reference were prepared: 50.5 μL (1 μM rhASB) into 5 mL uptake assay diluent (UAD, DMEM+2 mM L-glutamine+0.5 mg/mL BSA), resulting in 10 nM GALNS samples and reference, which were further serially diluted to 5, 2.5, 1.25, 0.62, 0.31 and 0.16 nM by serial two-fold dilutions in UAD. The growth medium from the 12-well dishes of confluent chondrocytes was aspirated, 1 mL of either UAD (blank) or serial dilutions of GALNS samples or references were added to the wells, and incubated for 4 hours at 37° C. in a 10% $CO_2$ incubator. The uptake medium was aspirated, tilting each dish for completeness, and each well was rinsed once with 1 mL PBS. The PBS was aspirated and the chondrocytes were detached by adding 0.5 mL trypsin/EDTA (0.25% Trypsin/0.1% EDTA (Mediatech 25-053-CI, lot 25053025)) per well. After detachment from the plate, the chondrocytes were aliquoted into prechilled-on-ice Eppendorf tubes (30 tubes total). The trypsinized chondrocytes were cooled and then pelleted at low speed in a microfuge (4000 rpm for 3 minutes). The trypsin was aspirated completely, the cell pellet was rinsed with 1 mL PBS, repeating the microfuge and aspiration steps once. 200 μL of cell lysis buffer (CLB, 50 mM sodium acetate, pH 5.6+0.1% Triton X-100) was added to each tube. Cell pellets were resuspended by pulse-vortexing three times. After resuspension, the cell lysis mixtures were stored overnight at ~80° C., or analyzed directly.

The cell lysates were thawed at room temperature and transferred to ice when thawed. The cell lysates were vortexed to resuspend any visible solid material, and then spun in the microfuge at 14 Krpm for 10 minutes at 4° C. to pellet the insoluble material. The supernatants were transferred to a fresh set of tubes and the pellet was discarded. Then GALNS activity assay was performed on the supernatants. A seven-point dilution curve (serial two-fold dilutions starting at 10 nM and ending at 0.16 nM) is usually performed which brackets the expected $K_{uptake}$ fairly evenly on both sides. The molarity of the starting samples is calculated by using the protein-only molecular weight.

The purified GALNS had a Kd for uptake into synoviocytes, based on single-site ligand binding, of 4.9 nM.

Mannose-6-Phosphate (M6P) Receptor Plate Binding Assay. The ability of GALNS to bind to the mannose-6-phosphate (M6P) receptor was determined in a plate binding assay. FluoroNunc high binding plates were coated with 4 μg/mL M6P receptor. The coated plates were washed twice with 250 μL/well of wash buffer (WB, TBS+0.05% TWEEN®-20) and nonspecific binding was blocked with 200 μL/well of blocking and dilution buffer (BDB, Pierce SuperBlock buffer, lot #CA46485). Plates were incubated for 1 hour at room temperature (RT). During this block step, purified GALNS samples (0.5-2 mg/mL stored at 4° C. for 2 weeks) were diluted to 10 nM in BDB, and then serially diluted in dilution buffer (DB, 50 mM NaOAc, 1 mM NaCl, pH 4.0+0.5 mg/mL BSA) (250 μL+250 μL) down to 5, 2.5, 1.25, 0.62, 0.31 and 0.16 nM. Blocked plates were washed with WB as above, and diluted GALNS samples were dispensed into the wells in duplicate at 100 μL/well and incubated 1 hour at RT. During this incubation step, 2 mM activity substrate was prepared by diluting 0.1 mL of the 100 mM 6S-galactose-4MU stock (stored in $H_2O$, −20° C.) into 5 mL DB, and prewarmed in a 37° C. water bath. After incubation, plates were washed twice with WB as above, and 100 μL diluted substrate was added and the GALNS specific activity was determined Using the assay, the purified GALNS had a Kd for binding to the M6P receptor, based on single-site binding, of 2.4 nM.

Mannose-6-Phosphate (M6P) Receptor Column Binding. The ability of GALNS to bind to the mannose-6-phosphate (M6P) receptor was determined in a column binding assay. A M6P receptor column was prepared per the manufacturer's instructions. M6P receptor was from Peter Lobel's laboratory, the column resin was NHS activated resin (Bio-RAD Affi-Gel 15), and the column size was 0.7 mL. The M6P receptor column was equilibrated with 10 column volumes (CV) of equilibration buffer (EQ, acidic PBS, pH 6.0 containing 5 mM β-glycerophosphate, 0.05% TWEEN®-20, 5 mM glucose-1-phosphate and 0.02% $NaN_3$) at a flow rate of 0.25 mL/min. 6 μg of purified GALNS (per 200 μl) was loaded onto the M6P receptor column at a flow rate of 0.1 mL/min. Unbound GALNS was washed off the column with 10 CV of EQ at a flow rate of 0.25 mL/min. Bound GALNS was eluted off the column using a 0-100% elution buffer (EL, acidic PBS, pH 6.0 containing 5 mM β-glycerophosphate, 0.05% TWEEN®-20, 5 mM mannose-6-phosphate and 0.02% $NaN_3$) gradient (10 CV), followed by 2 CV of 100% EL. The column was re-equilibrated with 3 CV of EQ.

Using the GALNS ELISA, the percent of purified GALNS that bound to the M6P receptor was determined to be 56%.

Total Oligosaccharides Analysis by Capillary Electrophoresis (CE). To determine the level of mannose-6-phosphorylation on GALNS, the N-linked carbohydrate profile of the total oligosaccharides on the GALNS was determined by capillary electrophoresis (CE) as described in IIIa et al., Anal. Chem. 71(22):5185-5192, 1999. The method used PNGase F to cleave asparagine N-linked oligosaccharides. The cleaved oligosaccharides were isolated and derivatized with fluorescent dye, and applied to a G10 spin column to remove excess dye. The purified, fluorescently labeled oligosaccharides were separated electrophoretically and peaks subsequentluy quantified using the MDQ-CE software (32 Karat Ver. 7.0).

Using this assay, the amounts of bis-phosphorylated mannose 7 (BPM7), mono-phosphorylated mannose 6 (MPM6) and sialic acid containing oligosaccharides for purified GALNS were 0.58 mol/mole enzyme, 0.08 mol/mol enzyme and not detectable, respectively. The percent of GALNS proteins containing BPM7 was estimated to be 29%.

Bis7 Oligosaccharide Characterization. The location of the bis-phosphorylated mannose 7 (BPM7) oligosaccharides on the GALNS was determined. The asparagine (Asn) residue at position 178 was N-linked glycosylated to BPM7. The Asn residue at position 397 was not N-linked glyosylated to BPM7, but was found to be predominantly oligo-mannose-type sugars.

Hydroxyapatite Affinity. An in vitro bone model was developed to determine whether the GALNS had the ability to target to bone. A 4 mg/mL HTP-DNA grade hydroxyapatite (Bio-RAD) suspension was prepared and equilibrated in DBS+50 µg/mL BSA, pH 7.4. The purified GALNS, after adding 50 µg/mL BSA, was desalted in DBS, pH 7.4. The desalted GALNS, at a final concentration of approximately 2 mg/mL, was serially diluted in DBS+50 µg/mL BSA, pH 7.4 in a 96-well plate. 50 µL of the serially diluted GALNS were transferred to 96-well filter plate (Millipore #MSGVN2210, hydrophilic PVDF, low protein binding, 22 µm pore size). 50 µL of the hydroxyapatite suspension was added to the wells of the filter plate containing the serially diluted GALNS and incubated for 1 hour at 37° C. with mild shaking. The plate was subjected to vacuum filtration.

The vacuum filter supernatants were analyzed by either HPLC or GALNS enzyme activity as described above. The purified GALNS had a Kd for hydroxyapatite of 3-4.0 µM.

The G71S cell line expressing human sulfatase modifying factor 1 (SUMF1) produces lysosomal sulfatase enzymes with higher amounts of activation (i.e., conversion of the active site cysteine residue to $C_\alpha$-formylglycine (FGly)).

To determine if the purified recombinant lysosomal sulfatase enzyme (e.g., human N-acetylgalactosamine-6-sulfatase (GALNS)) co-expressed with SUMF1 in G71S cells exhibits increased activation, the amount of conversion of active site cysteine residue to FGly on the purified lysosomal sulfatase enzyme was determined.

GALNS Activation. The percent activation, i.e., percent conversion of the active site cysteine (Cys) cysteine residue $C_\alpha$-formylglycine (FGly), of the GALNS was determined by LC/MS (TFA). The TIC/1000 for Cys, FGly and Gly were 39, 1840 and 183, respectively, indicating that about 90% of the purified GALNS is in an active (i.e., FGly) form.

Summary. Table 9 shows a summary of the characterization of recombinant GALNS expressed in G71S clone 4 cells. Table 10 shows a summary of the characterization of recombinant GALNS expressed in G71S clone C2 cells.

TABLE 9

Characterization of Human N-Acetylgalactosamine-6-Sulfatase (GALNS) Produced from G71S Clone 4

| Assay Category | GALNS |
|---|---|
| Specific Activity: Activity/Antigen by ELISA | 0.165 U/mg |
| Specific Activity: Activity/Protein | 7.7 U/mg |
| Purity by C4-RP | >95% (6 lots tested) |

TABLE 9-continued

Characterization of Human N-Acetylgalactosamine-6-Sulfatase (GALNS) Produced from G71S Clone 4

| Assay Category | GALNS |
|---|---|
| Size by SEC | 115 kDa (homodimer) |
| Serum Stability at 37° C. | 217 Hours |
| Uptake: Chondrocytes | 4.9 nM |
| Uptake: Fibroblasts | 5.0 nM |
| Uptake: Osteoblasts | 7.8 nM |
| Productivity | 1.3 pg/cell/day |
| Titer | 4.2 mg/L |
| M6P Receptor Plate Binding | 2.4 nM |
| M6P Receptor Column Binding: % Bound | 56% |
| M6P Content by CE: % of Total Carbohydrate | 29% |
| M6P Content: mol M6P/mol GALNS | 0.58 |
| Sialic Acid Content be CE | 1% |
| Hydroxyapatite Affinity | 4 µM |
| Activation: % FGly | 90% |

TABLE 10

Characterization of Human N-Acetylgalactosamine-6-Sulfatase (GALNS) Produced from G71S Clone C2

| Assay Category | GALNS |
|---|---|
| Specific Activity: Activity/Protein | 6.4 U/mg |
| Purity by C4-RP | 97% |
| Size by SEC | 115 kDa (homodimer) |
| Uptake: Fibroblasts | 3.4 nM |
| Titer | 6.4 mg/L (4 lots tested) |
| M6P Receptor Plate Binding | 5.7 nM |
| M6P Content by CE: % of Total Carbohydrate | 34.5% |
| M6P Content: mol M6P/mol GALNS | 0.69 |

These results demonstrate that the purified recombinant human GALNS has a high level of activation, and high levels of mannose 6-phosphate phosphorylation. Thus, G71S cells co-expressing SUMF1 and a lysosomal sulfatase enzyme (i.e., GALNS) efficiently produce active highly phosphorylated lysosomal sulfatase enzyme. The increased level of high mannose residues on such lysosomal sulfatase enzymes leads to increased uptake by the MPR on cells.

Example VIII

Uptake and Activity of Recombinant Human N-Acetylgalactosamine-6-Sulfatase (GALNS) in Morquio Chondrocytes In Vitro The uptake of recombinant human N-acetylgalactosamine-6-sulfatase (GALNS) by lysosomes of Morquio chondrocytes and the ability of GALNS to degrade keratan sulfate (KS) in vitro was evaluated.

Chondrocytes from patients with Mucopolysaccharidosis Type IVa (MPS IVa, Morquio Syndrome) have reduced GALNS activity and exhibit lysosomal accumulation of KS. An in vitro model of MPS IVa was established using chondrocytes isolated from iliac crest biopsies of a MPS IVa patient. Primary chondrocytes, however, de-differentiate and lose their chondrocyte characteristics in culture. Thus, culture conditions were established to induce chondrocyte differentiation in vitro.

Chondrocytes isolated from an MPS IVa patient, designated MQCH, were cultured in alginate beads in the presence of IGF-1, TGF-β, transferrin, insulin and ascorbic acid (Chondrocyte Growth Medium, Lonza #CC-3225). The culture medium was changed twice per week for the duration of the experiments, from 6 to 15 weeks. These culture conditions induced expression of the chondrocyte phenotype and differentiation. These MQCH cells expressed chondrocyte markers, including sex determining region Y-box 9 (Sox 9), collagen II, collagen X, cartilage oligomeric matrix protein and aggrecan mRNA, as measured by quantitative RT-PCR analysis using RNA isolated from cultures of MQCH cells. These cultured MQCH cells also elaborated extracellular matrix.

Confocal microscopy was performed to confirm that the MQCH cells accumulated KS. The MQCH cells in an 8-week culture were trypsinized, cytospun onto glass slides, fixed in acetone, and frozen until use. After thawing, the cells were rehydrated and stained using, as primary and secondary antibodies, an anti-KS monoclonal antibody (Chemicon) and an Alexa-488 (green) conjugated goat anti-rabbit antibody, respectively. The MQ-CH cells displayed punctate intracellular staining, consistent with lysosomal KS accumulation.

To determine whether purified recombinant human GALNS could be taken up by MQCH cells into lysosomes and degrade KS, a 6-week MQCH cell culture was incubated with 10 nM recombinant human GALNS twice per week for 9 weeks. GALNS uptake and KS clearance were measured by confocal microscopy. The primary antibodies used were: (a) an anti-GALNS rabbit polyclonal antibody and an anti-Lysosomal Associated Membrane Protein-1 (LAMP-1) monoclonal antibody, or (b) an anti-KS monoclonal antibody and an anti-LAMP-1 polyclonal antibody. The secondary antibodies used were: Alexa-488 (green) conjugated antibodies to detect anti-GALNS or anti-KS antibodies, or Alexa-555 or -594 (red) conjugated antibodies to detect anti-LAMP-1 antibodies. MQCH cell preparations were mounted in mountant containing DAPI, which stains nuclei.

Significant co-localization of the GALNS enzyme and KS with the lysosome marker, LAMP-1, was observed in GALNS-treated MQCH cells. Upon exposure of MQCH to recombinant human GALNS, the amount of intracellular KS was decreased.

GALNS uptake was also measured using a GALNS enzyme capture ELISA and a GALNS specific activity ELISA, both described in Example IV above. Normal human chondrocytes (NHKC), which express GALNS, were used as a positive control. As shown in Tables 11 and 12, untreated MQCH cells had no detectable GALNS enzyme or activity, whereas MCQH cells treated for 9 weeks with 10 nM GALNS had significant GALNS enzyme and activity.

TABLE 11

GALNS Enzyme Capture ELISA Using MQCH Cells

| | MQCH Cells | NHKC |
|---|---|---|
| No treatment | N.D.[a] | 0.12[b] |
| 10 nM GALNS for 9 wks | 3.99 | 0.88 |

[a]Not detected;
[b]ng GALNS antigen/μg total protein

TABLE 12

GALNS Specific Activity Assay Using MQCH Cells

| | MQCH Cells | NHKC |
|---|---|---|
| No treatment | N.D.[a] | 2.76[b] |
| 10 nM GALNS for 9 wks | 3.68 | 5.15 |

[a]Not detected;
[b]GALNS activity/ng antigen

These results demonstrate that purified recombinant human GALNS is taken up by Morquio chondrocytes into lysosomes and can degrade lysosomal KS in vitro. These Morquio chondrocytes are useful as an in vitro efficacy model to test lysosomal sulfatase enzymes, such as GALNS, which degrade KS.

Example IX

Activity of Recombinant Human Lysosomal Enzymes to Degrade Natural Substrates in a Cell-Based Assay In Vitro Cell-based in vitro assays were developed to measure the activity of recombinant human lysosomal enzymes, e.g., lysosomal sulfatase enzymes, to degrade natural substrates.

The enzymatic activity of recombinant human lysosomal enzymes, e.g., lysosomal sulfatase enzymes, is typically measured by a cell-free in vitro assay using an artificial fluorogenic substrate (see Example 4 for GALNS). However, the enzyme activity measured is dependent on the size of the artificial substrate, i.e., number of monosaccharide units. In addition, the enzyme activity is measured in an environment that is not reflective of the situation in vivo. Thus, the cell-free in vitro assay does not take into account either the lysosomal enzyme's ability to cleave natural substrates, or its ability to be taken up into target cells and localize to lysosomes.

A cell-based in vitro assay was developed to measure the activity of two recombinant human lysosomal enzymes, alpha-L-iduronidase (IDU) and arylsulfatase B (ARSB), to degrade their natural substrates, i.e., intracellular dermatan sulfate (DS)-containing substrates. DS contains variably sulfated iduronic acid $\beta(1-3)$-N-acetyl-galactosamine $\beta(1-4)$ disaccharide units.

ARSB-deficient GM00519 human fibroblast cells or IDU-deficient GM01391 human fibroblast cells were cultured to confluency in 12-well plates, and the cultures were maintained post-confluency for 3-6 weeks to allow for accumulation of intracellular DS.

Post-confluent GM00519 or GM01391 cells were then exposed to saturating doses of recombinant human ARSB (10 nM) or recombinant human IDU (25 nM), respectively, for 4-5 days. Untreated and lysosomal sulfatase enzyme-treated cells were harvested, lysed and centrifuged.

Lysosomal enzyme activity in the cell lysates was measured by determining the residual DS content of the cells by: (1) lysing the cells; (2) specifically digesting DS-containing substrates into disaccharides using chondroitin ABC lyase (EC 4.2.2.4) in the cell lysate; (3) labeling DS disaccharides with a fluorescent dye (e.g., 2-amino-acridone, AMAC); (4) separating the DS disaccharides (e.g., by capillary zone electrophoresis, CZE); and (5) detecting the labeled DS disaccharides (e.g., by laser-induced fluorescence, LIF). Such methods are described, for example, in Zinellu et al., Electrophoresis 2:2439-2447, 2007, and Lamari et al., J. Chromatogr. B 730:129-133, 1999 (reviewed in Volpi et al., Electrophoresis 29:3095-3106, 2008).

Table 13 shows the percent degradation of DS using GM00519 cells treated with ARSB, as determined by measuring the amount of disaccharide containing N-acetylgalactosamine-4-sulfate (4S disaccharide), which is the predominant DS disaccharide. Similar results were obtained using GM01391 cells treated with IDU.

TABLE 13

Depletion of DS by ARSB in a Cell-Based In Vitro Assay

| Age of Cells (Weeks) | GM00519 Cells (% Degradation)[a] |
| --- | --- |
| 3 | 86 |
| 4 | 92 |
| 5 | 92 |
| 6 | 89 |

[a]Percent degradation was calculated by measuring the area under the curve of the 4S disaccharide detected in the CZE-LIF scan in lysates from ARSB-treated as compared to untreated cells The above assay indicated that target cells take up recombinant human ARSB and IDU, which are then localized to lysosomes, where they degrade their natural substrate, intracellular DS.

A dose finding experiment was performed to determine the concentration at which IDU becomes rate limiting in this cell-based assay. GM01391 cells were cultured in 12-well plates. At 4 weeks post-confluency, the cells were exposed to various concentrations of IDU, from 0.8 nM to 25 nM, for 6 or 26 hours. Cell lysates were prepared and processed as described above. IDU was determined not to become rate limiting below 1 nM.

Figure 13:
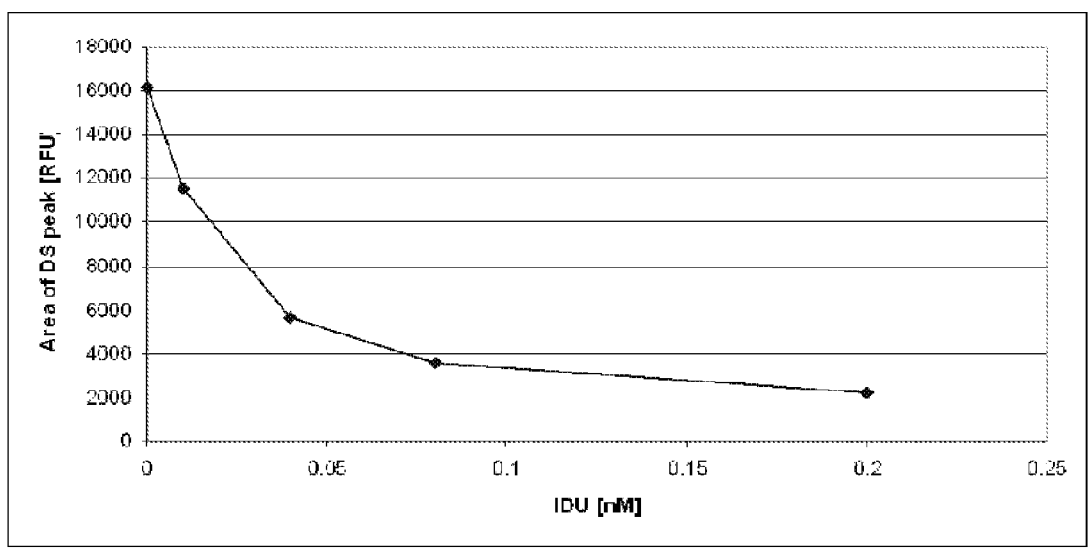
FIG. 13 shows a dose dependent decrease in the amount of dermatan sulfate substrate was observed in the IDU-treated GM01391 cells.

In a second dose finding experiment, GM01391 cells at 3 weeks post-confluency were exposed to various concentrations of IDU, from 0.01 to 0.2 nM, for 2 days. Cell lysates were prepared and processed as described above. In this experiment, a known amount of an internal standard monosaccharide, GlcNAc-6S, was spiked into the cell lysates to control for recovery during processing. As shown in FIG. 13, a dose dependent decrease in the amount of DS substrate was observed in the IDU-treated GM01391 cells.

Figure 14:
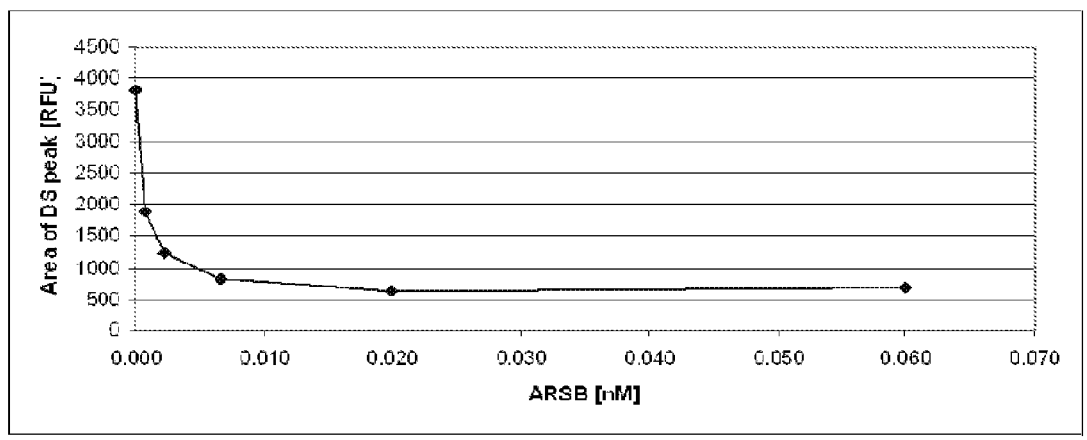
FIG. 14 shows a dose dependent decrease in the amount of dermatan sulfate substrate was observed in the ARSB-treated GM00519 cells.

In a similar dose finding experiment, GM00519 cells at 3 weeks post-confluency were exposed to various concentrations of ARSB, from 0.001 to 0.06 nM, for 5 days. Cell lysates were prepared and processed as described above. In this experiment, a known amount of an internal standard monosaccharide, GlcNAc-6S, was spiked into the cell lysates to control for recovery during processing. As shown in FIG. 14, a dose dependent decrease in the amount of DS substrate was observed in the ARSB-treated GM00519 cells.

A cell-based in vitro assay was developed to measure the activity of a recombinant human lysosomal sulfatase enzyme, GALNS, to degrade its natural substrate, i.e., intracellular keratan sulfate (KS)-containing substrates.

GALNS-deficient MQCH cells were cultured as described in Example 8 above and treated with recombinant human GALNS at 1 or 10 nM. After treatment, MQCH cell lysates were prepared and digested with Keratanase II (EC 3.2.1), which breaks down larger KS oligosaccharides into KS disaccharides. The KS disaccharides were labeled with AMAC, separated by CZE and detected by LIF, as described above for DS disaccharides. GlcNAc-6S, a KS monosaccharide, was spiked into the cell lysates as internal standard to control for recovery during processing. The amounts of two characteristic KS disaccharides, Gal6S-GlcNAc6S and Gal-GlcNAc6S were measured, and the data obtained was corrected by the amount of GlcNAc6S recovered. Table 14 shows the percent degradation of KS using MQCH cells treated with GALNS, as determined by measuring the amount of the two characteristic KS disaccharides.

TABLE 14

Depletion of KS by GALNS in a Cell-Based In Vitro Assay

| | Gal6S-GlcNAc6S | Gal-GlcNAc6S |
| --- | --- | --- |
| 1 nM GALNS | 85.7[a] | 78.5[b] |
| 10 nM GALNS | 88.6 | 81.5 |

[a,b]Percent degradation was calculated by measuring the area under the curve of the Gal6S-GlcNAc6S and Gal-GlcNAc6S detected in the CZE-LIF scan in lysates from GALNS-treated as compared to untreated MQCH cells, and adjusting for the area under the curve of the spike control GlcNAc6S The above assay indicated that target cells take up recombinant human GALNS, which is then localized to lysosomes, where GALNS degraded its natural substrate, intracellular KS.

Overall, these results demonstrated that the activity of recombinant human lysosomal enzymes, ARSB, IDU and GALNS, to degrade their natural substrates can be measured and quantified in cell-based in vitro assays. It should be appreciated that this cell-based in vitro assay can be readily modified to measure and quantify the activity of other lysosomal sulfatase enzymes, as well as a wide variety of recombinant lysosomal enzymes.

Example X

Delivery of Recombinant Human N-Acetylgalactosamine-6-Sulfatase (GALNS) to Specific Tissues The ability of recombinant human N-acetylgalactosamine-6-sulfatase (GALNS), expressed in G71 cells and purified, to be delivered to specific tissues affected by, or associated with, deficiency of GALNS upon its administration into mice was evaluated.

The highly specific distribution of keratan sulfate gives the very characteristic phenotype of Mucopolysaccharidosis Type IVa (MPS IVA) or Morquio Syndrome. Keratan sulfate is primarily found in cartilage (joints bone growth plates, the heart valve, larynx and nasal septum) and cornea, and it is these tissues that exhibit keratan sulfate accumulation in MPS IVA patients. Thus, for N-acetylgalactosamine-6-sulfatase (GALNS), which is deficient in MPS IVA or Morquio Syndrome, it is important to show delivery of the GALNS enzyme to the growth plate of long bones, the heart valve, cornea, larynx and nose. To look at these specific tissues, which are poorly vascularized targets, delivery of a fluorescent GALNS was investigated in mice.

Two immunohistochemical staining methods were tested in mice: (1) human GALNS conjugated with Alexa 488 and (2) unconjugated human GALNS. The conjugation of human GALNS to Alexa 488 was performed using Molecular Probes Alexa Fluor 488 $C_5$ maleimide labeling kit (A-10254). The maleimide conjugation chemistry resulted in a 1:1 labeling to protein ratio.

Figure 15:
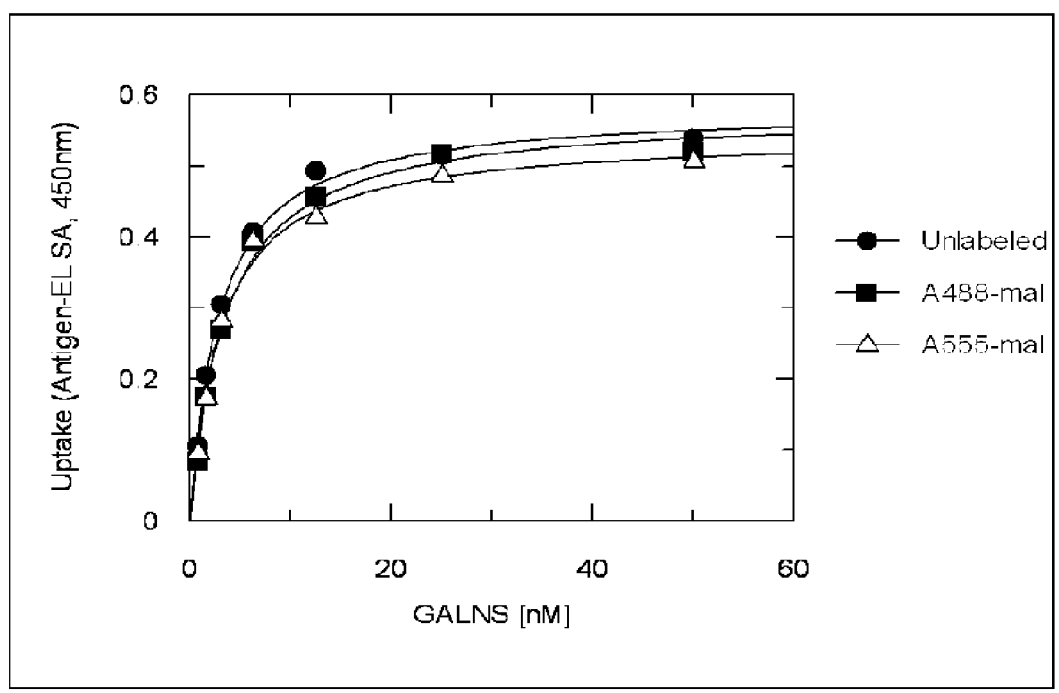
FIG. 15 shows the uptake of human N-acetylgalactosamine-6-sulfatase (GALNS), either unlabeled (circles) or conjugated with A488 (squares) or A555 (triangles), by cultured synoviocytes.

To confirm that the fluorescent tag did not interfere with uptake of GALNS, an immunocytochemistry experiment was done using cultured synoviocytes (ATCC #CRL-1832). A standard uptake assay was used to compare the unconjugated GALNS with conjugated GALNS (GALNS-A488 or GALNS-A555). Cells were incubated with GALNS enzyme for 4 hours with a subsequent chase with α-L-iduronidase (IDU) for 2 hours. The results showed that the Alexa 488 conjugation did not interfere with cellular uptake. FIG. 15 shows the estimated Kd for GALNS, GALNS-A488, and GALNS-A555. The uptake was measured by antigen ELISA of the cell lysate rather than enzyme activity because the labeling inactivated the enzyme. The Kd of the unconjugated and conjugated GALNS enzymes were determined to be about equal.

To determine the stability of the fluorescent tag once the GALNS enzyme was incorporated into the cell, immunostaining on unconjugated and conjugated GALNS was performed. The primary antibody used for the staining was a protein G-purified anti-GALNS rabbit antibody at a concentration of 1 µg/mL. All images were taken on a Leica IRE2 widefield epi-fluorescent microscope using META-MORPH® software. Deconvolution of the image stacks was required to measure co-localization in these images due to the presence of out-of-plane light. The deconvolution was done using AutoQuant/AutoDeblur visualization software using a theoretical point spread function (blind algorithm).

The immunostaining showed fairly good overlap with signal that was amplified over the GALNS-A488 material. The observed increase in sensitivity was due to the primary and the secondary antibody both being polyclonal.

To determine if the GALNS enzyme was targeted to the lysosome, immunostaining of the cultured synoviocytes with Molecular Probes Lysotracker or another enzyme that localizes in the lysosome was performed. Lysotracker appeared to show some overlap with the GALNS-488 enzyme; however, the staining wasn't uniform. A 2 hr chase with recombinant human N-acetylgalactose amine-4-sulfatase (rhASB), a lysosomal enzyme, did show some co-localization with GALNS.

The above experiments showed that GALNS-A488 enzyme is taken up by cells and localizes to the lysosome, and can be used to determine biodistribution in vivo.

Two in vivo studies were conducted. A first pilot study was a single dose (10 mg/kg) bolus injection in the tail vein of normal Balb/c mice, followed by a second study with multiple (5) injections every other day of 10 mg/kg in the tail vein of normal Balb/c mice. Table 15 and Table 16 describe the experimental plans for the first and second studies, respectively.

TABLE 15

Experimental Design of First Pilot Study

| Group | Total | 2 hr Time Point | 24 hr Time Point |
|---|---|---|---|
| PBS Control | 4 | 2 | 2 |
| GALNS-A488 | 4 | 2 | 2 |
| Unlabeled GALNS | 4 | 2 | 2 |
| Unlabeled ASB | 1 | 1 | 0 |

TABLE 16

Experimental Design of Second Study

| Group | Total | 2 hr Time Point | 4 hr Time Point | 8 hr Time Point |
|---|---|---|---|---|
| PBS Control | 2 | 1 | 0 | 1 |
| PBS/Cys Control | 4 | 2 | 0 | 2 |
| GALNS-A488 | 9 | 3 | 3 | 3 |
| Unlabeled GALNS | 6 | 3 | 0 | 3 |
| Unlabeled ASB | 3 | 2 | 0 | 1 |

In the first pilot study, the heart, the liver and the tibia/femur joint were harvested at 2 hour and 24 hour time points. In the second study, the heart, the kidney, the liver, and the bone with quadricep and soleus were harvested at 2 hour, 4 hour and 8 hour time points. For both studies, the heart, kidney, and liver were immersion fixed in 4% paraformaldehyde (PFA) for 4 days, paraffin embedded, then sectioned to 7 µm thickness. The bone, including the muscle in the second study, was immersion fixed in 4% PFA for 8 days, decalcified, paraffin embedded, and sectioned to 7 µm thickness.

Images of the GALNS-A488 injected mice were acquired on a Zeiss laser scanning confocal microscope. For the analysis in the first pilot study, one confocal stack per sample was acquired for the heart valve and liver and used for volumetric analysis. Two confocal stacks/sample were acquired for the growth plate and used for volumetric analysis. In the second study, one confocal stack/sample for heart valve, kidney and liver was acquired and used for volumetric analysis; two confocal stacks/sample for growth plate and zone of rest cartilage (zrc) were acquired and used for volumetric analysis.

The conclusions from the confocal microscopy imaging studies were: (1) it was possible to detect fluorescent GALNS in vivo; (2) the signal was specific (absence of background) and the localization was lysosomal; (3) the presence of GALNS was demonstrated in the sinusoidal cell in the liver; (5) in the heart, the GALNS enzyme was present in the septum and the atrium, but more importantly it was clearly visible at the level of the heart valve, where it was more deeply distributed after multiple injections; (6) at the femur/tibia junction, the GALNS enzyme was present in the mineralized part of the bone (epiphysis), as well as the marrow. GALNS was present in the growth plate. More particularly, GALNS was abundant in the chondrocytes of the resting zone (or zone of reserve cartilage), present at the beginning of the proliferative zone, and reappeared abundantly in the ossification zone at the end of the growth plate. Although difficult to quantify the cumulative effect of multiple injections, the second study seemed to display a broader distribution. Table 17 shows a summary of the confocal microscopy imaging studies.

TABLE 17

Biodistribution of GALNS in Mice

| Tissue | Localization |
|---|---|
| Bone (Femur) | |
| Mineralized region | Yes |
| Bone Marrow | Yes |
| Growth Plate | Yes |
| Heart | |
| Heart valve | Yes |
| Atrium | Yes |
| Septum | Yes |
| Liver | |
| Hepatocyte | No |
| Sinusoidal Cell | Yes |

For secondary staining, the initial step was optimization of the GALNS primary antibody. Various tissues were stained with dilutions of 1:100 to 1:400 with the protein G-purified anti-GALNS rabbit antibody. Results in the first pilot study indicated that a dilution of 1:100 was optimal for a high signal to noise ratio. This result was confirmed in the second study. The remaining slides were processed at a primary antibody dilution of 1:100 and a secondary antibody dilution of 1:1000.

Signal for Balb/c mice dosed with GALNS had a signal above control (i.e., PBS-Cys dosed mice) when stained with the protein G-purified anti-GALNS antibody. To confirm that the GALNS enzyme was localized in the lysosome, the sections were stained with an anti-LAMP1 antibody. LAMP1 is a marker for lysosomes. The images showed overlap between the anti-LAMP1 and anti-GALNS antibodies, indicating that the GALNS enzyme was localized in the lysosome.

Overall, the two in vivo studies indicate that GALNS biodistribution is linked to vascularization, i.e., the more vascularized tissues contain more fluorescent signal. More importantly, the studies demonstrate the presence of GALNS at the sites of keratan sulfate accumulation in Morquio Syndrome, even if these sites are poorly vascularized.

Example XI

Formulations of Human N-Acetylgalactosamine-6-Sulfatase (GALNS)

The objective was to investigate the effect of various excipients, e.g., buffers, isotonicity agents, and stabilizers, on the activity and structure of recombinant human N-acetylgalactosamine-6-sulfatase (GALNS) in formulations of the invention.

The GALNS enzyme was prepared as described in EXAMPLE V.

The GALNS enzyme was characterized as described in EXAMPLE VII.

In EXAMPLE V, the purified, recombinant human GALNS enzyme was formulated in 10 mM NaOAc/HOAc, 1 mM $NaH_2PO_4$, 150 mM NaCl, and 0.005% or 0.01% TWEEN®-20, at pH 5.5. It was noted that upon storage in the low concentration phosphate buffer, dephosphorylation of the GALNS enzyme occurred. Accordingly, the phosphate buffer concentration was increased to 100 mM $NaH_2PO_4$. Upon storage in the high concentration phosphate buffer, no significant dephosphorylation of the GALNS enzyme was observed. However, soluble aggregates of GALNS were observed upon storage at 5° C., 25° C. or 40° C., and insoluble aggregates of GALNS were observed upon storage at 40° C.

In a first study, the effect of stabilizer concentration and pH on stability of the recombinant GALNS was evaluated. Purified recombinant GALNS enzyme was formulated in 20 mM NaOAc/HOAc, 50 mM $NaH_2PO_4$, 0.01% TWEEN®-20, and 4% sucrose or 2% sorbitol. Stabilizers tested: 15 mM or 30 mM arginine hydrochloride (Arginine HCl); and 15 mM or 30 mM NaCl. pH tested: 5.0, 5.4 and 5.8. The pH 5.8 formulations were determined to vary from pH 5.8 to 6.0. After storing the enzyme formulations for up to 2 months at 5° C., 25° C. or 40° C., the GALNS enzyme was analyzed using various assays described in EXAMPLE VI.

Figure 16:
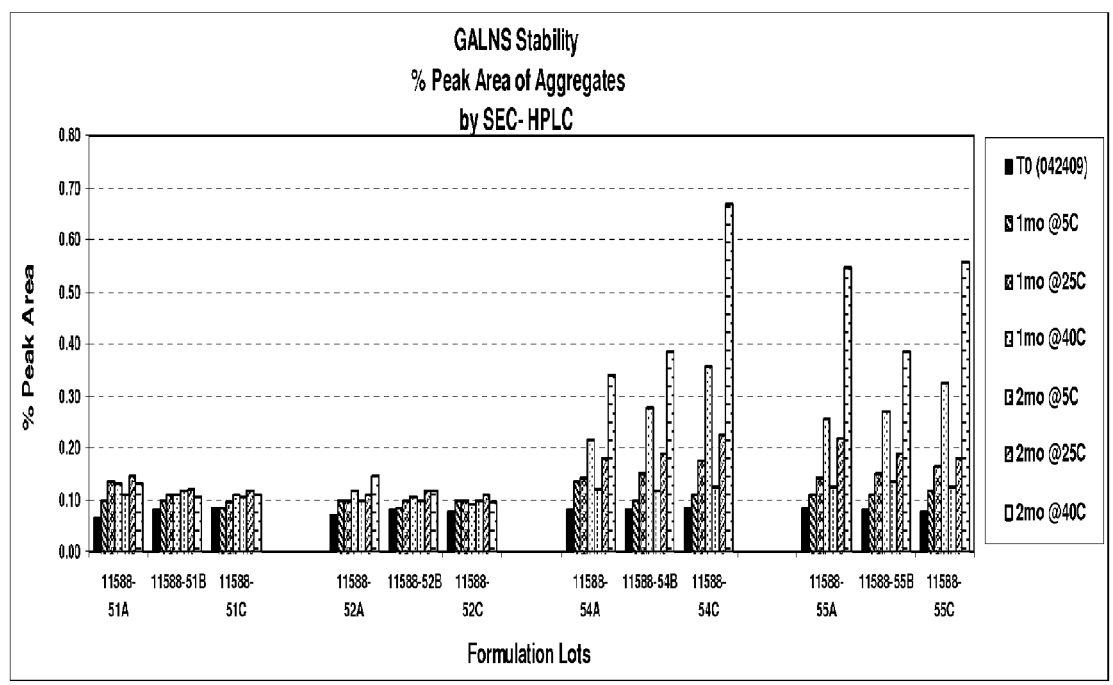
FIG. 16 shows the stability of purified human N-acetylgalactosamine-6-sulfatase (GALNS) enzyme upon storage for 1 or 2 months at 5° C., at 25° C. or at 40° C. as indicated in a formulation comprising 15 mM Arginine HCl, 30 mM Arginine HCl, 15 mM NaCl or 30 mM NaCl (panels designated 51, 52, 54 or 55, respectively) at pH 5.0, pH 5.4 or pH 5.8 (panels designated A, B or C, respectively). Stability was measured by the percent (%) peak area of GALNS aggregates in the formulation after storage as determined by size exclusion chromatography-high performance liquid chromatography (SEC-HPLC).

The formation of soluble aggregates in the various formulations was determined by profiling the GALNS enzyme by size exclusion chromatography-high performance liquid chromatography (SEC-HPLC). The presence of both 15 mM and 30 mM Arginine HCl suppressed the growth of soluble aggregates as determined by SEC-HPLC (FIG. 16).

Figure 17:
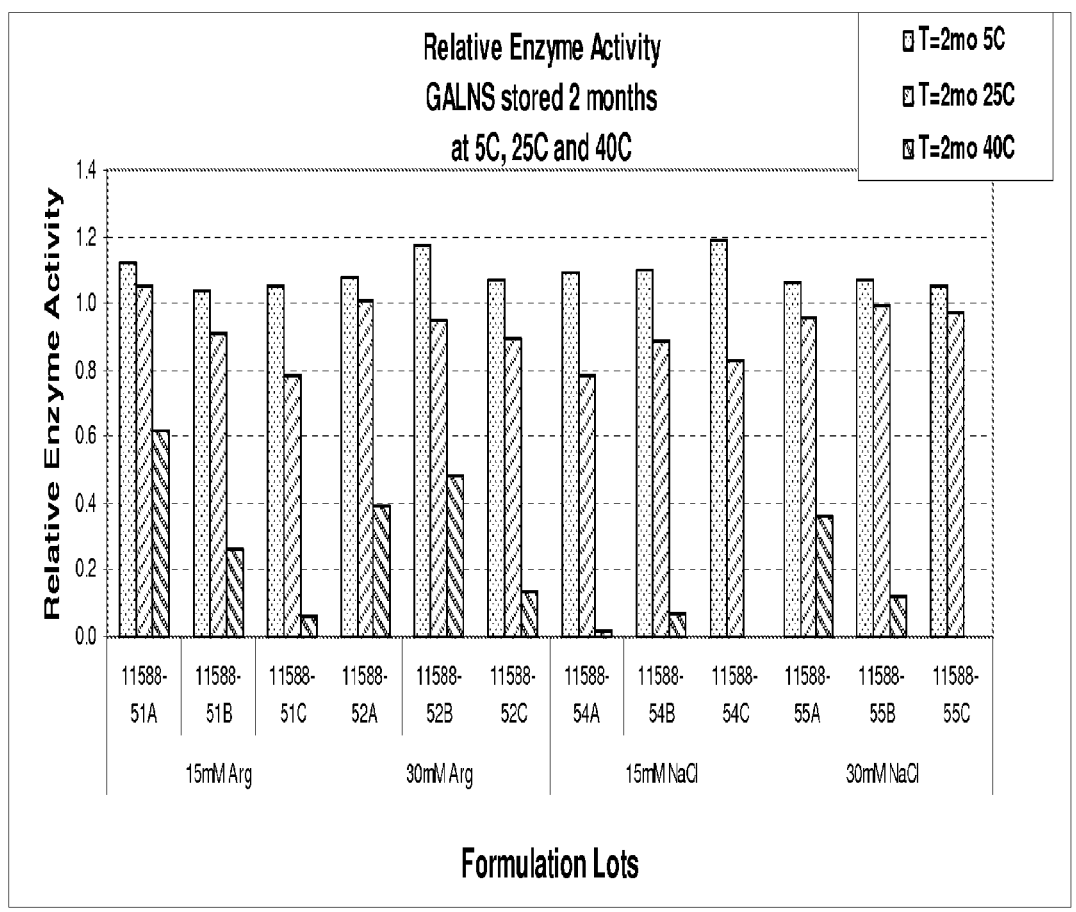
FIG. 17 shows the stability of purified human N-acetylgalactosamine-6-sulfatase (GALNS) enzyme activity upon storage for 2 months at 5° C., at 25° C. or at 40° C. as indicated in a formulation comprising 15 mM Arginine HCl, 30 mM Arginine HCl, 15 mM NaCl or 30 mM NaCl (panels designated 51, 52, 54 or 55, respectively) at pH 5.0, pH 5.4 or pH 5.8 (panels designated A, B or C, respectively).

The stability of GALNS enzyme activity in the formulations was measured using the in vitro enzyme activity assay. At 5° C., GALNS enzyme activity was stable in the presence of Arginine HCl or NaCl; at 25° C., GALNS enzyme activity was slightly decreased in the presence of either Arginine HCl or NaCl; and at 40° C., GALNS enzyme activity in the NaCl containing formulations exhibited the least stability (FIG. 17).

Dephosphorylation of the GALNS enzyme in the formulations was investigated by measuring the percent of bis-phosphorylated mannose 7 (BPM7) by capillary electrophoresis (CE) after digestion of the enzyme with PNGase F to cleave the asparagine N-linked oligosaccharides. After 2 months at 5° C., 25° C. or 40° C., the GALNS enzyme in all of the enzyme formulations had a glycosylation profile in terms of % BPM7 that was comparable to the glycosylation profile of a reference lot of GALNS that is used in the phase I clinical formulation (FIG. 18).

Figure 19:
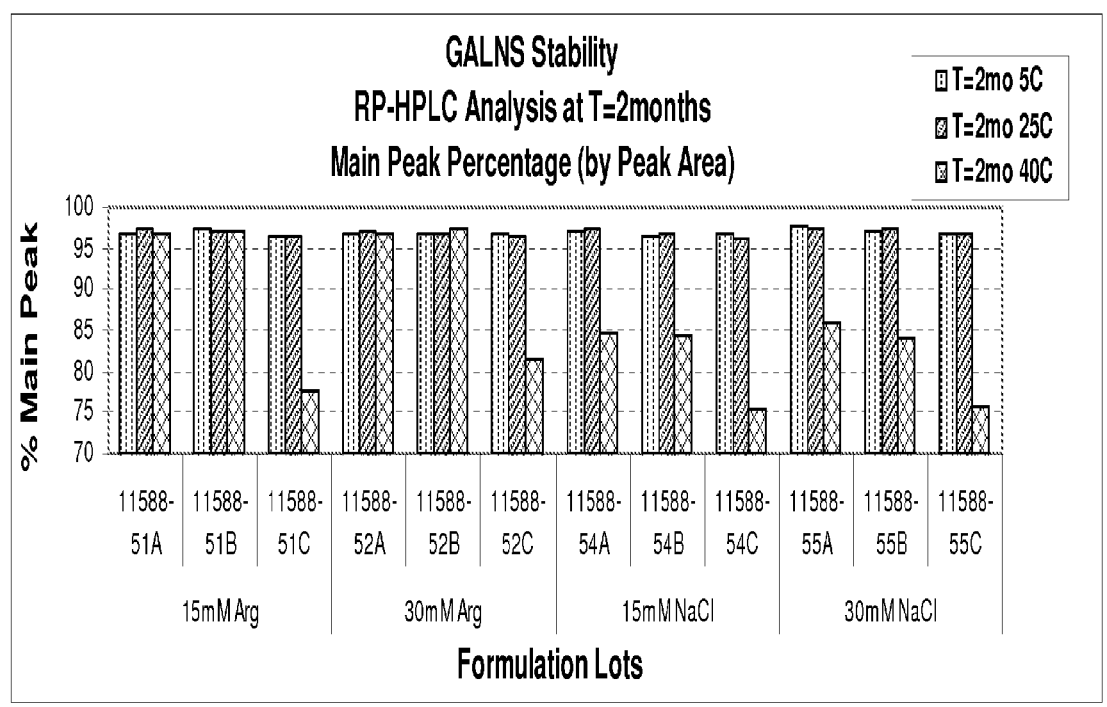
FIG. 19 shows the stability of purified human N-acetylgalactosamine-6-sulfatase (GALNS) enzyme upon storage for 2 months at 5° C., at 25° C. or at 40° C. as indicated in a formulation comprising 15 mM Arginine HCl, 30 mM Arginine HCl, 15 mM NaCl or 30 mM NaCl (panels designated 51, 52, 54 or 55, respectively) at pH 5.0, pH 5.4 or pH 5.8 (panels designated A, B or C, respectively). Stability of GALNS enzyme was measured percent (%) peak area of GALNS enzyme in the formulation after storage as determined by reverse phase-high performance liquid chromatography (RP-HPLC).

Purity of the GALNS enzyme in the formulations was determined by profiling the enzyme by reverse phase-high performance liquid chromatography (RP-HPLC). After 2 months at 5° C. or 25° C., none of the formulations exhibited any peak area changes; at 40° C., the Arginine HCl containing formulations at pH 5.0 and pH 5.4 also did not exhibit any peak area changes, but the NaCl containing formulations at pH 5.0 and pH 5.4 and all of the formulations at pH 5.8 exhibited a decrease in peak area (FIG. 19). In the RP-HPLC chromatograms, a post-peak shoulder was observed in the formulations. The GALNS formulation containing 30 mM Arginine HCl exhibited the least prominent post-peak shoulder.

Example XII

Exemplary Formulations of Human N-Acetylgalactosamine-6-Sulfatase (GALNS)

The following example provides guidance on the parameters to be used to formulate compositions comprising recombinant human N-acetylgalactosamine-6-sulfatase (GALNS) or biologically active fragments, mutant, variants or analogs thereof, which are useful for treatment of Morquio Syndrome or MPS IVa. Parameters to be used to formulate GALNS compositions of the invention include, but are not limited to, buffering agents to maintain pH, isotonicity-adjusting agents, absence or presence of stabilizers, and absence or presence of other excipients, vehicles, diluents, and the like.

In EXAMPLE XI, the recombinant GALNS was formulated at a concentration of about 1 mg/mL. A preferred GALNS is formulated at a concentration ranging from about 0.1 to 10 mg/mL, preferably from about 0.5 to 5 mg/mL, and more preferably from about 0.5 to 1.5 mg/mL. In one embodiment, a formulation of the GALNS composition of the invention has a GALNS enzyme concentration of about 1+/−0.5 mg/mL.

In EXAMPLE XI, the recombinant GALNS enzyme was formulated in 20 mM NaOAc/HOAc, 50 mM $NaH_2PO_4$, at pH 5.0, 5.4 and 5.8. A preferred buffering agent is NaOAc/HOAc, or its equivalent, and $NaH_2PO_4$, or its equivalent, with the NaOAc/HOAc concentration ranging from about 5 to 100 mM, preferably from about 5 to 50 mM, and more preferably from about 10 to 30 mM, and the $NaH_2PO_4$ concentration ranging from about 5 to 100 mM, preferably from about 25 to 100 mM, and more preferably from about 25 to 75 mM. In an exemplary embodiment, a formulation of the GALNS composition of the invention has a NaOAc/HOAc buffer concentration of about 20+/−10 mM and a $NaH_2PO_4$ buffer concentration of about 50+/−25 mM.

A preferred pH of the formulation is about pH 4.5-6.5, preferably about pH 5.0-6.0, and more preferably about pH 5.0-5.8. In one embodiment, a formulation of the GALNS composition of the invention has a pH of about pH 5.4+/−0.4.

In EXAMPLE XI, the recombinant GALNS enzyme was formulated in 15 mM or 30 mM Arginine HCl or NaCl. A preferred stabilizing agent is Arginine HCl, or its equivalent, with a concentration ranging from about 5 to 200 mM, preferably from about 10 to 100 mM, and more preferably from about 10 to 50 mM. In an exemplary embodiment, a formulation of the GALNS composition of the invention has an Arginine HCl concentration of about 30+/−20 mM.

In EXAMPLE XI, the recombinant GALNS enzyme was formulated in 0.01% TWEEN®-20. A preferred stabilizing agent is TWEEN®-20 (also known as Polysorbate-20), or its equivalent, with a concentration ranging from about 0.001 to 1.0% (w/v), preferably from about 0.005 to 0.2% (w/v), and more preferably from about 0.005 to 0.015% (w/v). In one embodiment, a formulation of the GALNS composition of the invention has a TWEEN®-20 concentration of about 0.01%+/−0.005% (w/v).

In EXAMPLE XI, the recombinant GALNS enzyme was formulated in 4% sucrose or 2% sorbitol. A preferred stabilizing/cryoprotectant/tonicity agent is sorbitol, or its equivalent, with a concentration ranging from about 0.1 to 10% (w/v), preferably from about 0.5 to 5% (w/v), and more preferably from about 1.0 to 3.0% (w/v). An exemplary formulation of the GALNS compositions of the invention has a sorbitol concentration of about 2.0%+/−1.0% (w/v).

Accordingly, an exemplary formulation of the GALNS enzyme compositions of the invention is shown in Table 18.

TABLE 18

Exemplary Formulations of Recombinant Human GALNS

| Ingredient Class | Ingredient Type | Concentration Range |
|---|---|---|
| Active Substance | Recombinant human GALNS | 1.0 +/− 0.5 mg/mL |
| Buffering Agent | NaOAc/HOAc<br>Sodium Acetate, Trihydrate* | 20 mM +/− 10 mM<br>(2.72 mg/mL +/− 1.36 mg/mL)<br>and pH 5.4 +/− 0.4 |
| Buffering Agent | NaH$_2$PO$_4$<br>Sodium Phosphate, Monobasic Monohydrate | 50 mM +/− 25 mM<br>(6.90 mg/mL +/− 3.45 mg/mL) |
| Stabilizer | Arginine HCl | 30 mM +/− 20 mM<br>(6.32 mg/mL +/− 4.11 mg/mL) |
| Stabilizer | TWEEN ®-20 | 0.01% (w/v) +/− 0.005% (w/v)<br>(0.1 mg/mL +/− 0.05 mg/mL) |
| Stabilizer, Cryoprotectant and Tonicity Agent | Sorbitol | 2.0% (w/v) +/− 1.0% (w/v)<br>(20 mg/mL +/− 10 mg/mL) |

*pH is adjusted by titration with glacial acetic acid (HOAc) or 1N sodium hydroxide (NaOH)

Example XIII

Effects of Recombinant Human N-Acetylgalactosamine-6-Sulfatase (GALNS) and Other Lysosomal Sulfatase Enzymes in Mice Deficient in Lysosomal Sulfatase Enzyme Activity The effects of the active highly phosphorylated human lysosomal sulfatase enzymes of the invention, e.g., recombinant human N-acetylgalactosamine-6-sulfatase (GALNS), in mice deficient in lysosomal sulfatase enzyme activity are evaluated.

The recombinant human GALNS protein is expressed in G71S cells and purified. Other recombinant human lysosomal sulfatase enzymes can be expressed and purified basically according to methods described herein or by procedures known in the art.

Several mouse models of human lysosomal sulfatase enzyme deficiency have been described, including: Metachromatic Leukodystrophy (MLD) (arylsulfatase A deficiency), (Hess et al., *Proc. Natl. Acad. Sci. USA* 93:14821-14826, 1996), Mucopolysaccharidosis type VI (MPS VI) or Maroteaux-Lamy syndrome (arylsulfatase B deficiency) (Evers et al., *Proc. Natl. Acad. Sci. USA* 93:8214-8219, 1996), Mucopolysaccharidosis type II (MPS II) or Hunter syndrome (iduronate-2-sulfatase deficiency) (Muenzer et al., *Acta Paediatr. Suppl.* 91(439):98-99, 2002; Cardone et al., *Hum. Mol. Genet.* 15:1225-1236, 2006), Mucopolysaccharidosis type IIIa (MPS IIIa) or Sanfilippo A syndrome (sulfamidase/heparan-N-sulfatase deficiency) (Bhaumik et al., *Glycobiology* 9(12):1389-1396, 1999), Mucopolysaccharidosis type IVa (MPS IVa) or Morquio A syndrome (N-acetylgalactosamine-6-sulfatase deficiency) (Tomatsu et al., *Hum. Mol. Genet.* 12:3349-3358, 2003), and Multiple Sulfatase Deficiency (MSD) (sulfatase modifying factor 1 deficiency) (Settembre et al., *Proc. Natl. Acad. Sci. USA* 104:4506-4511, 2007). A mouse model of Mucopolysaccharidosis type IIId (MPS IIId) or Sanfilippo D syndrome (N-acetylglucosamine-6-sulfatase deficiency) has yet to be described.

Mouse models of human lysosomal sulfatase enzyme deficiency can be used to assess the feasibility of enzyme replacement therapy (ERT) as a means for treating lysosomal storage disorders. For example, MPS IVa knock-out mice (GALNS$^{-/-}$ mice; Tomatsu et al., *Hum. Mol. Genet.* 12:3349-3358, 2003) have no detectable GALNS enzyme activity and display increased urinary glycosaminoglycans (GAGs), i.e., keratin sulfate and chondroitin-6-sulfate, and accumulation of GAGs in multiple tissues and organs, e.g., liver, kidney, spleen, heart, brain, bone marrow and cartilage. The GALNS$^{-/-}$ mice do not, however, display skeletal abnormalities associated with the human disease. Another MPS IVa mouse model was developed that expresses an inactive human GALNS and a mutated, inactive endogenous mouse GALNS (GALNS$^{tm(hC79S.mC76S)slu}$ mice; Tomatsu et al., *Hum. Mol. Genet.* 14:3321-3335, 2005). In GALNS$^{tm(hC79S.mC76S)slu}$ mice, which have no detectable GALNS enzyme activity, urinary GAG excretion is increased, GAGs accumulate in multiple tissues, including visceral organs, brain, cornea, bone, ligament and bone marrow, lysosomal storage is marked in multiple tissues, and bone storage is evident. The pathological alterations in GALNS$^{tm(hC79S.mC76S)slu}$ mice are different from those observed in GALNS$^{-/-}$ mice. However, like the GALNS$^{-/-}$ mice, GALNS$^{tm(hC79S.mC76S)slu}$ mice do not display skeletal abnormalities associated with the human disease. Thus, GALNS$^{-/-}$ or GALNS$^{tm(hC79S.mC76S)slu}$ mice can be used to investigate the effect of administration of recombinant human GALNS on increased urinary GAGs and accumulation of GAGs in the tissues.

Four week old GALNS$^{-/-}$, GALNS$^{tm(hC79S.mC76S)slu}$ or wild-type mice are given weekly intravenous injections (n=at least 6 or 8 per group) of various doses of recombinant human GALNS (e.g., 0.1, 0.3, 1, 3, 10 mg/kg) or a vehicle control through 16-20 weeks of age, and then sacrificed for histological examination. Urine is collected from mice and urinary GAG excretion is determined as described (Tomatsu et al., *Hum. Mol. Genet.* 12:3349-3358, 2003). Pathological examination of various tissues is performed as described (Tomatsu et al., *Hum. Mol. Genet.* 12:3349-3358, 2003).

Using the GALNS$^{-/-}$ or GALNS$^{tm(hC79S.mC76S)slu}$ mice, the recombinant human GALNS of the invention is expected to demonstrate the ability to reduce: (1) urinary GAG excretion; (2) accumulation of GAGs in multiple tissues, e.g., visceral organs, brain, cornea, bone, ligament and bone marrow; (3) lysosomal storage in multiple tissues; and (4) bone storage.

The effect of recombinant human GALNS is investigated in a mouse model of Multiple Sulfatase Deficiency (MSD) (SUMF1$^{-/-}$ mice; Settembre et al., *Proc. Natl. Acad. Sci. USA* 104:4506-4511, 2007). Because SUMF1$^{-/-}$ mice display frequent mortality early in life, injections of these mice with recombinant human GALNS is initiated earlier than that described above for GALNS$^{-/-}$ mice.

Following procedures known in the art, the effects of other recombinant human lysosomal sulfatase enzymes, i.e., arylsulfatase A, arylsulfatse B, iduronate-2-sulfatase, sulfamidase/heparan-N-sulfatase, and N-acetylglucosamine-6-sulfatase, are investigated in mouse models of MLD (ASA$^{-/-}$ mice; Hess et al., *Proc. Natl. Acad. Sci. USA* 93:14821-14826, 1996), MPS VI (As1-s$^{-/-}$ mice; Evers et al., *Proc. Natl. Acad. Sci. USA* 93:8214-8219, 1996), MPS II (ids$^{y/-}$ mice; Cardone et al., *Hum. Mol. Genet.* 15:1225-1236, 2006), MPS IIIa (Bhaumik et al., *Glycobiology* 9(12):1389-1396, 1999) and MSD (SUMF1$^{-/-}$ mice; Settembre et al., *Proc. Natl. Acad. Sci. USA* 104:4506-4511, 2007).

Example XIV

Treatment of Human Patients with Mucopolysaccharidis Type IVA (or Morquio Syndrome) or other Lysosomal Sulfatase Enzyme Deficiencies with Recombinant Human N-Acetylgalactosamine-6-Sulfatase (GALNS) and other Lysosomal Sulfatase Enzymes Human patients manifesting a clinical phenotype of lysosomal sulfatase enzyme deficiency, such as in patients diagnosed with Mucopolysaccharidosis Type IVA (MPS IVa or Morquio Syndrome), are contemplated for enzyme replacement therapy with the recombinant enzyme, i.e., human N-acetylgalactosamine-6-sulfatase (GALNS). All patients suffering from a lysosomal sulfatase enzyme deficiency manifest some clinical evidence of excessive or harmful visceral and soft tissue accumulation of storage material in their lysosomes as manifested by varying degrees of functional impairment or worsening health status associated with a particular lysosomal storage disease. All the MPS IVa patients manifest some clinical evidence of bone deformity, short stature and abnormal gait, and/or accumulation of glycosaminoglycan (GAG) in the blood or urine, with varying degrees of functional impairment.

Preferably, enzyme levels are monitored in a patient suffering from a lysosomal sulfatase enzyme deficiency to confirm the absence or reduced activity of the lysosomal sulfatase enzyme in their tissues. Patients with less than 10%, preferably less than 5%, more preferably less than 2% and even more preferably less than 1% of the lysosomal enzyme activity in an otherwise normal subject are suitable candidates for treatment with the appropriate lysosomal sulfatase enzyme. Data may be collected to determine the patient's lysosomal sulfatase enzyme activity before, during and after therapy.

Efficacy is determined by measuring the percentage reduction in urinary excretion of the substrate, i.e., glycosaminoglycan (GAG) of the lysosomal sulfatase enzyme over time. The urinary GAG levels in patients suffering from a lysosomal sulfatase enzyme deficiency are compared to normal excretion levels and/or levels in untreated patients suffering from the same lysosomal sulfatase enzyme deficiency and/or levels in the same patient before therapy with the lysosomal sulfatase enzyme. A greater than 25% reduction, preferably greater than 50% reduction, in excretion of undegraded GAGs following therapy with the lysosomal sulfatase enzyme is a valid means to measure an individual's response to therapy.

Efficacy can also be determined according to the reduced signs and symptoms of pathology associated with the lysosomal storage disease. Efficacy can be determined by tissue biopsy and examination of cells and/or lysosomes to determine the extent by which GAGs have been reduced in the lysosomes, cells or tissues. Efficacy can be determined by functional assessments, which may be objective or subjective (e.g., reduced pain or difficulty in function, increased muscle strength or stamina, increased cardiac output, exercise endurance, changes in body mass, height or appearance, and the like).

A pharmaceutical composition comprising recombinant human GALNS, expressed in G71S cells and purified, and formulated according to procedures known in the art. It is preferred to administer the pharmaceutical compositions of the invention intravenously.

The basic design of an initial clinical study to investigate the effect of administration of recombinant human GALNS to MPS IVa patients involves an open label, dose escalation safety/efficacy study in which various doses of enzyme are administered intravenously to the patients at a fixed interval, for example and not for limitation, weekly enzyme injections.

For MPS IVa patients, efficacy is determined by measuring, for example, decreased blood or urinary GAG, which is likely to be observed within weeks of ERT, increased endurance in tests of cardiac, pulmonary and/or motor function, which is likely to be observed within months of ERT, and/or skeletal changes and/or body growth, which is likely to be observed within years of ERT.

Urinary GAG measurements are useful for establishing an appropriate dose regimen, as well as for determining efficacy, by measuring the percentage reduction in urinary GAG excretion over time.

A variety of endurance tests may be employed, including for example and not for limitation, walk tests (distance walked in 6 or 12 minutes), stair climb (stairs per minute), and pulmonary/respiratory function, including cardiac function (ECG, echocardiogram), pulmonary function (FVC, FEV$_1$, peak flow).

For younger patients undergoing treatment for extended periods of time, growth (height) may be measured.

The lysosomal storage diseases associated with deficiency in lysosomal sulfatase enzyme activity that can be treated or prevented using the methods of the present invention are:

Metachromatic Leukodystrophy (MLD), Mucopolysaccharidosis type VI (MPS VI) or Maroteaux-Lamy syndrome, Mucopolysaccharidosis type II (MPS II) or Hunter syndrome, Mucopolysaccharidosis type IIIa (MPS IIIa) or Sanfilippo A syndrome, Mucopolysaccharidosis type IIId (MPS IIId) or Sanfilippo D syndrome, Mucopolysaccharidosis type IVa (MPS IVa) or Morquio A syndrome, or Multiple Sulfatase Deficiency (MSD). For each lysosomal storage disease, the recombinant lysosomal sulfatase enzyme would comprise a specific lysosomal sulfatase enzyme.

For methods involving MLD, the preferred lysosomal sulfatase enzyme is arylsulfatase A. For methods involving MPS VI, the preferred lysosomal sulfatase enzyme is arylsulfatse B. For methods involving MPS II, the preferred lysosomal sulfatase enzyme is iduronate-2-sulfatase. For methods involving MPS IIIA, the preferred lysosomal sulfatase enzyme is sulfamidase/heparan-N-sulfatase. For methods involving MPS IIID, the preferred lysosomal sulfatase enzyme is N-acetylglucosamine-6-sulfatase. For methods involving MPS IVA, the preferred lysosomal sulfatase enzyme is N-acetylgalactosamine-6-sulfatase. For methods involving MSD, the preferred lysosomal sulfatase enzyme is N-acetylgalactosamine-6-sulfatase.

Numerous modifications and variations of the invention as set forth in the above illustrative examples are expected to occur to those skilled in the art. Consequently only such limitations as appear in the appended claims should be placed on the invention.

What is claimed:

1. A method of purifying a recombinant human N-acetyl-galactosamine-6-sulfatase (GALNS) enzyme, said GALNS enzyme comprising an amino acid sequence at least 95% identical to amino acids 27 to 522 of SEQ ID NO:4, wherein said GALNS enzyme:

has a purity of at least about 95% as determined by Coomassie Blue staining when subjected to SDS-PAGE under non-reducing conditions, has at least about 50% conversion of the cysteine residue at position 53 to $C_a$-formylglycine (FGly), and optionally, has between 0.5 to 0.8 bis-phosphorylated oligomannose chains per monomeric protein chain, and wherein at least 97% of said GALNS enzyme is in the precursor form as determined by SDS-capillary gel electrophoresis (SDS-CGE), comprising:

a) filtering a culture medium containing the GALNS enzyme secreted from a mammalian cell line that expresses human sulfatase modifying factor 1 (SUMF1) and the recombinant human GALNS enzyme, ultrafiltering/diafiltering the filtered culture medium, and charcoal filtering the ultrafiltered/diafiltered culture medium;

b) loading the charcoal filtered ultrafiltered/dialfiltered culture medium from step a) onto a capture column, washing the capture column under conditions such that the GALNS enzyme is retained on the capture column, and eluting the GALNS enzyme from the capture column;

c) optionally, filtering the eluate from the capture column in step b) through a filter to remove viruses;

d) adjusting the pH of the eluate from the capture column from step b) or the filtrate from step c) to an acid pH, and filtering the acid pH-adjusted eluate from the capture column or acid pH-adjusted filtrate;

e) loading the acid pH-adjusted eluate from the capture column or acid pH-adjusted Q filtrate from step d) onto an intermediate column, washing the intermediate column under conditions such that the GALNS enzyme is retained on the intermediate column, and eluting the GALNS enzyme from the intermediate column;

f) adjusting the eluate from the intermediate column in step e) to low pH for viral inactivation;

g) loading the low pH viral inactivated eluate from step f) onto a polishing column, washing the polishing column under conditions such that the GALNS enzyme is retained on the polishing column, and eluting the GALNS enzyme from the polishing column; and h) buffer exchanging the eluate from the polishing column in step g) into a formulation comprising
(i) an amount of phosphate buffer effective to reduce dephosphorylation of said GALNS enzyme, wherein the phosphate buffer is $NaH_2PO_4$ at a concentration from about 25 mM to 75 mM; and
(ii) a stabilizing amount of the following stabilizers: an arginine salt or buffer, optionally arginine hydrochloride, wherein the arginine salt or buffer is at a concentration from about 10 mM to 50 mM; a polysorbate, optionally polysorbate 20; and a trihydric or higher sugar alcohol, optionally sorbitol; wherein said formulation is at a pH of about 5.0-5.8.

2. The method of claim 1, wherein the culture medium is concentrated about 20× in step a).

3. The method of claim 1, wherein step c) is performed and the filter is a Mustang Q filter.

4. The method of claim 1, further comprising:
   i) removing any residual virus and DNA by filtering the buffer exchanged formulation from step h) with a viral filter and a DNA filter; and
   j) adding a non-ionic surfactant to the formulation from step i).

5. The method of claim 1, wherein the formulation in step h) comprises 20 mM NaOAc/HOAc, 50 mM NaH$_2$PO$_4$, 30 mM arginine HCl, 2% (w/v) sorbitol, pH 5.4.

6. The method of claim 1, wherein the GALNS enzyme in the formulation in step h) is adjusted to about 3 mg/mL.

7. A method of purifying a recombinant human N-acetylgalactosamine-6-sulfatase (GALNS) enzyme, said GALNS enzyme comprising an amino acid sequence at least 95% identical to amino acids 27 to 522 of SEQ ID NO:4, wherein said GALNS enzyme:
   has a purity of at least about 95% as determined by Coomassie Blue staining when subjected to SDS-PAGE under non-reducing conditions, has at least about 50% conversion of the cysteine residue at position 53 to $C_a$-formylglycine (FGly), and optionally, has between 0.5 to 0.8 bis-phosphorylated oligomannose chains per monomeric protein chain, and wherein at least 97% of said GALNS enzyme is in the precursor form as determined by SDS-CGE, comprising:
   a) filtering a culture medium containing the GALNS enzyme secreted from a mammalian cell line that expresses human sulfatase modifying factor 1 (SUMF1) and the recombinant human GALNS enzyme, ultrafiltering/diafiltering the filtered culture medium, whereby the ultrafiltered/diafiltered culture medium is concentrated about 20×, and charcoal filtering the 20× concentrated ultrafiltered/diafiltered culture medium;
   b) loading the charcoal filtered 20× ultrafiltered/dialfiltered culture medium from step a) onto a Zn-chelating Sepharaose FF capture column, washing the column under conditions such that the GALNS enzyme is retained on the column, and eluting the GALNS enzyme from the column;
   c) optionally, filtering the eluate from the Zn-chelating Sepharaose FF capture column in step b) through a filter to remove viruses;
   d) adjusting the pH of the eluate from the Zn-chelating Sepharose FF capture column from step b) or the filtrate from step c) to about pH 4.5±0.1, and filtering the pH 4.5-adjusted eluate from the Zn-chelating Sepharose FF capture column or filtrate;
   e) loading the pH 4.5-adjusted eluate from the Zn-chelating FF capture column or filtrate from step d) onto a Fractogel EMD SE Hi-Cap cation exchange column, washing the column under conditions such that the GALNS enzyme is retained on the column, and eluting the GALNS enzyme from the column;
   f) adjusting the pH of the eluate from the Fractogel EMD SE Hi-Cap cation exchange column from step e) to about pH 3.5±0.1 for viral inactivation;
   g) loading the pH 3.5 viral inactivated eluate from step f) onto a ToyoPearl Butyl 650 M polishing column, washing the column under conditions such that the GALNS enzyme is retained on the column, and eluting the GALNS enzyme from the column;
   h) buffer exchanging the eluate from the ToyoPearl Butyl 650 M polishing column from step g) into a formulation comprising 20 mM NaOAc/HOAc, 50 mM NaH$_2$PO$_4$, 30 mM arginine HCl, 2% (w/v) sorbitol, pH 5.4, and adjusting the concentration of the GALNS enzyme in the formulation to about 3 mg/mL;
   i) removing any residual virus and/or DNA by filtering the buffer exchanged formulation in step h) with a DV20 filter and a Mustang Q filter; and
   j) adding polysorbate 20 (PS20) to the formulation in step i) to a final concentration of 0.01% (w/v).

8. A composition purified according to claim 1, said composition comprising
   (a) a recombinant human N-acetylgalactosamine-6-sulfatase (GALNS) enzyme, said GALNS enzyme comprising an amino acid sequence at least 95% identical to amino acids 27 to 522 of SEQ ID NO:4, wherein said GALNS enzyme:
   has a purity of at least about 95% as determined by Coomassie Blue staining when subjected to SDS-PAGE under non-reducing conditions, has at least about 50% conversion of the cysteine residue at position 53 to $C_a$-formylglycine (FGly), and optionally, has between 0.5 to 0.8 bis-phosphorylated oligomannose chains per monomeric protein chain, and wherein at least 98% of said GALNS enzyme is in the precursor form as determined by SDS-CGE; and
   (b) one or more pharmaceutically acceptable carriers, diluents or excipients comprising:
      (i) an amount of phosphate buffer effective to reduce dephosphorylation of said GALNS enzyme, wherein the phosphate buffer is NaH$_2$PO$_4$ at a concentration from about 25 mM to 75 mM; and
      (ii) a stabilizing amount of the following stabilizers: an arginine salt or buffer, optionally arginine hydrochloride, wherein the arginine salt or buffer is at a concentration from about 10 mM to 50 mM; a polysorbate, optionally polysorbate 20; and a trihydric or higher sugar alcohol, optionally sorbitol; wherein said composition is at a pH of about 5.0-5.8.

9. A formulation comprising
   (a) recombinant human N-acetylgalactosamine-6-sulfatase (GALNS) enzyme, said GALNS enzyme comprising an amino acid sequence at least 95% identical to amino acids 27 to 522 of SEQ ID NO:4, and
   having a purity of at least about 95% as determined by Coomassie Blue staining when subjected to SDS-PAGE under non-reducing conditions, having at least about 50% conversion of the cysteine residue at position 53 to $C_a$-formylglycine (FGly), and optionally, having between 0.5 to 0.8 bis-phosphorylated oligomannose chains per monomeric protein chain, wherein at least 97% of said GALNS enzyme is in the precursor form as determined by SDS-CGE, and
   (b) one or more pharmaceutically acceptable carriers, diluents or excipients comprising:
      (i) an amount of phosphate buffer effective to reduce dephosphorylation of said GALNS enzyme, wherein the phosphate buffer is NaH$_2$PO$_4$ at a concentration from about 25 mM to 75 mM; and
      (ii) a stabilizing amount of the following stabilizers: an arginine salt or buffer, optionally arginine hydrochloride, wherein the arginine salt or buffer is at a concentration from about 10 mM to 50 mM; a polysorbate, optionally polysorbate 20; and a trihydric or higher sugar alcohol, optionally sorbitol; wherein said formulation is at a pH of about 5.0-5.8.

10. The formulation of claim 9, wherein the formulation further comprises an acetate buffer, wherein the acetate buffer is NaOAc/HOAc at a concentration from about 10 to 30 mM.

11. The formulation of claim 9, wherein the GALNS enzyme exhibits a specific uptake (Kuptake) into fibroblasts that is about 1 to 5 nM.

12. The formulation of claim 9, wherein the concentration of GALNS enzyme is from about 0.5 to 1.5 mg/mL.

13. The composition of claim 8 further comprising an acetate buffer, wherein the acetate buffer is NaOAc/HOAc at a concentration from about 10 to 30 mM.

14. A formulation comprising
   (a) recombinant human N-acetylgalactosamine-6-sulfatase (GALNS) enzyme, said GALNS enzyme comprising an amino acid sequence at least 95% identical to amino acids 27 to 522 of SEQ ID NO:4, and
      having a purity of at least about 95% as determined by Coomassie Blue staining when subjected to SDS-PAGE under non-reducing conditions,
      having at least about 50% conversion of the cysteine residue at position 53 to $C_a$-formylglycine (FGly), and
      having between 0.5 to 0.8 bis-phosphorylated oligomannose chains per monomeric protein chain,
      wherein at least 97% of said GALNS enzyme is in the precursor form as determined by Coomassie Blue staining when subjected to SDS-PAGE under reducing conditions, and
   (b) one or more pharmaceutically acceptable carriers, diluents or excipients comprising:
      (i) NaOAc/HOAc and $NaH_2PO_4$ as buffering agents, wherein the concentration of NaOAc/HOAc is about 20+/−10 mM and the concentration of NaH.sub.2PO.sub.4 is about 50+/−25 mM;
      (ii) Arginine HCl, Tween-20 and sorbitol as stabilizers, wherein the concentration of Arginine HCl is about 30+/−20 mM, the concentration of Tween-20 is about 0.01%+/−0.005% (w/v) and the concentration of sorbitol is about 2.0%+/−1.0% (w/v); and
      (iii) a pH of about 5.4+/−0.4.

15. The formulation of claim 14, wherein the GALNS enzyme exhibits a specific uptake (Kuptake) into fibroblasts that is about 1 to 5 nM.

16. The formulation of claim 14, wherein the concentration of GALNS enzyme is about 1.0+/−0.5 mg/mL.

17. A composition purified according to claim 7, said composition comprising a recombinant human N-acetylgalactosamine-6-sulfatase (GALNS) enzyme, said GALNS enzyme comprising
   (a) an amino acid sequence at least 95% identical to amino acids 27 to 522 of SEQ ID NO:4, wherein said GALNS enzyme:
      has a purity of at least about 95% as determined by Coomassie Blue staining when subjected to SDS-PAGE under non-reducing conditions,
      has at least about 50% conversion of the cysteine residue at position 53 to $C_a$-formylglycine (FGly), and
      optionally, has between 0.5 to 0.8 bis-phosphorylated oligomannose chains per monomeric protein chain,
      and wherein at least 98% of said GALNS enzyme is in the precursor form as determined by SDS-CGE; and
   (b) one or more pharmaceutically acceptable carriers, diluents or excipients comprising:
      (i) NaOAc/HOAc and $NaH_2PO_4$ as Buffering agents, wherein the concentration of NaOAc/HOAc is about 20+/−10 mM and the concentration of $NaH_2PO_4$ is about 50+/−25 mM;
      (ii) Arginine HCl, Tween-20 and sorbitol as stabilizers, wherein the concentration of Arginine HCl is about 30+/−20 mM, the concentration of Tween-20 is about 0.01%+/−0.005% (w/v) and the concentration of sorbitol is about 2.0%+/−1.0% (w/v); and
      (iii) a pH of about 5.4+/−0.4.

18. A method of treating a subject suffering from Mucopolysaccharidosis type IVa (MPS IVa) or Morquio A syndrome, comprising administering to the subject a therapeutically effective amount of the composition of claim 8 or 17 or the formulation of claim 9.

19. A method of preventing dephosphorylation of a recombinant human GALNS enzyme comprising mixing
   (a) recombinant human N-acetylgalactosamine-6-sulfatase (GALNS) enzyme, said GALNS enzyme comprising an amino acid sequence at least 95% identical to amino acids 27 to 522 of SEQ ID NO:4, and having a purity of at least about 95% as determined by Coomassie Blue staining when subjected to SDS-PAGE under non-reducing conditions, having at least about 50% conversion of the cysteine residue at position 53 to $C_a$-formylglycine (FGly), and optionally, having between 0.5 to 0.8 bis-phosphorylated oligomannose chains per monomeric protein chain, wherein at least 97% of said GALNS enzyme is in the precursor form as determined by SDS-CGE, and
   (b) one or more carriers, diluents or excipients comprising:
      (i) an amount of phosphate buffer effective to reduce dephosphorylation of said GALNS enzyme wherein the phosphate buffer is $NaH_2PO_4$ at a concentration from about 25 mM to 75 mM;
      (ii) a stabilizing amount of the following stabilizers: an arginine salt or buffer, optionally arginine hydrochloride, wherein the arginine salt or buffer is at a concentration from about 10 mM to 50 mM; a polysorbate, optionally polysorbate 20; and a trihydric or higher sugar alcohol, optionally sorbitol; and
      (iii) a pH of about 5.0-5.8.

* * * * *

UNITED STATES PATENT AND TRADEMARK OFFICE
CERTIFICATE OF CORRECTION

PATENT NO. : 9,567,572 B2  
APPLICATION NO. : 14/573907  
DATED : February 14, 2017  
INVENTOR(S) : Vish Koppaka et al.

Page 1 of 1

It is certified that error appears in the above-identified patent and that said Letters Patent is hereby corrected as shown below:

On the Title Page

At item (63), "8,904,513" should be -- 8,940,513 --.

In the Claims

At Column 102, Line 10, "Buffering" should be -- buffering --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 5

<210> SEQ ID NO 1
<211> LENGTH: 1125
<212> TYPE: DNA
<213> ORGANISM: Homo sapiens
<220> FEATURE:
<221> NAME/KEY: misc_feature
<223> OTHER INFORMATION: Human Sulfatase Modifying Factor 1 (SUMF1)
      Polynucleotide Sequence

<400> SEQUENCE: 1
atggctgcgc ccgcactagg gctggtgtgt ggacgttgcc ctgagctggg tctcgtcctc     60
ttgctgctgc tgctctcgct gctgtgtgga gcggcaggga gccaggaggc cgggaccggt    120
gcgggcgcgg ggtcccttgc gggttcttgc ggctgcggca cgccccagcg gcctggcgcc    180
catggcagtt cggcagccgc tcaccgatac tcgcgggagg ctaacgctcc gggccccgta    240
cccggagagc ggcaactcgc gcactcaaag atggtcccca tccctgctgg agtatttaca    300
atgggcacag atgatcctca gataaagcag gatggggaag cacctgcgag gagagttact    360
attgatgcct tttacatgga tgcctatgaa gtcagtaata ctgaatttga aagtttgtg     420 aactcaactg gctatttgac agaggctgag aagtttggcg actcctttgt ctttgaaggc    480
atgttgagtg agcaagtgaa gaccaatatt caacaggcag ttgcagctgc tccctggtgg    540
ttacctgtga aaggcgctaa ctggagacac ccagaagggc ctgactctac tattctgcac    600
aggccggatc atccagttct ccatgtgtcc tggaatgatg cggttgccta ctgcacttgg    660
gcagggaagc ggctgcccac ggaagctgag tgggaataca gctgtcgagg aggcctgcat    720
aatagacttt tcccctgggg caacaaactg cagcccaaag ccagcatta  tgccaacatt    780 tggcagggcg agtttccggt gaccaacact ggtgaggatg gcttccaagg aactgcgcct    840
gttgatgcct tccctcccaa tggttatggc ttatacaaca tagtggggaa cgcatgggaa    900
tggacttcag actggtggac tgttcatcat tctgttgaag aaacgcttaa cccaaaaggt    960
cccccttctg ggaaagaccg agtgaagaaa ggtgatcct  acatgtgcca  taggtcttat   1020
tgttacaggt atcgctgtgc tgctcggagc cagaacacac ctgatagctc tgcttcgaat   1080
ctgggattcc gctgtgcagc cgaccgcctg cccaccatgg actga                    1125

<210> SEQ ID NO 2
<211> LENGTH: 374
<212> TYPE: PRT
<213> ORGANISM: Homo sapiens
<220> FEATURE:
<221> NAME/KEY: MISC_FEATURE
<223> OTHER INFORMATION: Human Sulfatase Modifying Factor 1 (SUMF1)
      Polypeptide Sequence
```

<400> SEQUENCE: 2

```
Met Ala Ala Pro Ala Leu Gly Leu Val Cys Gly Arg Cys Pro Glu Leu
1               5                   10                  15

Gly Leu Val Leu Leu Leu Leu Leu Ser Leu Leu Cys Gly Ala Ala
            20                  25                  30

Gly Ser Gln Glu Ala Gly Thr Gly Ala Gly Ala Gly Ser Leu Ala Gly
        35                  40                  45

Ser Cys Gly Cys Gly Thr Pro Gln Arg Pro Gly Ala His Gly Ser Ser
    50                  55                  60

Ala Ala Ala His Arg Tyr Ser Arg Glu Ala Asn Ala Pro Gly Pro Val
65                  70                  75                  80

Pro Gly Glu Arg Gln Leu Ala His Ser Lys Met Val Pro Ile Pro Ala
                85                  90                  95

Gly Val Phe Thr Met Gly Thr Asp Asp Pro Gln Ile Lys Gln Asp Gly
            100                 105                 110

Glu Ala Pro Ala Arg Arg Val Thr Ile Asp Ala Phe Tyr Met Asp Ala
        115                 120                 125

Tyr Glu Val Ser Asn Thr Glu Phe Glu Lys Phe Val Asn Ser Thr Gly
130                 135                 140

Tyr Leu Thr Glu Ala Glu Lys Phe Gly Asp Ser Phe Val Phe Glu Gly
145                 150                 155                 160

Met Leu Ser Glu Gln Val Lys Thr Asn Ile Gln Gln Ala Val Ala Ala
                165                 170                 175

Ala Pro Trp Trp Leu Pro Val Lys Gly Ala Asn Trp Arg His Pro Glu
            180                 185                 190

Gly Pro Asp Ser Thr Ile Leu His Arg Pro Asp His Pro Val Leu His
        195                 200                 205

Val Ser Trp Asn Asp Ala Val Ala Tyr Cys Thr Trp Ala Gly Lys Arg
    210                 215                 220

Leu Pro Thr Glu Ala Glu Trp Glu Tyr Ser Cys Arg Gly Gly Leu His
225                 230                 235                 240

Asn Arg Leu Phe Pro Trp Gly Asn Lys Leu Gln Pro Lys Gly Gln His
                245                 250                 255

Tyr Ala Asn Ile Trp Gln Gly Glu Phe Pro Val Thr Asn Thr Gly Glu
            260                 265                 270

Asp Gly Phe Gln Gly Thr Ala Pro Val Asp Ala Phe Pro Pro Asn Gly
        275                 280                 285

Tyr Gly Leu Tyr Asn Ile Val Gly Asn Ala Trp Glu Trp Thr Ser Asp
    290                 295                 300

Trp Trp Thr Val His His Ser Val Glu Glu Thr Leu Asn Pro Lys Gly
305                 310                 315                 320

Pro Pro Ser Gly Lys Asp Arg Val Lys Lys Gly Gly Ser Tyr Met Cys
                325                 330                 335

His Arg Ser Tyr Cys Tyr Arg Tyr Arg Cys Ala Ala Arg Ser Gln Asn
            340                 345                 350

Thr Pro Asp Ser Ser Ala Ser Asn Leu Gly Phe Arg Cys Ala Ala Asp
        355                 360                 365

Arg Leu Pro Thr Met Asp
    370
```

<210> SEQ ID NO 3
<211> LENGTH: 1569
<212> TYPE: DNA

<213> ORGANISM: Homo sapiens
<220> FEATURE:
<221> NAME/KEY: misc_feature
<223> OTHER INFORMATION: Human N-Acetylgalactosamine-6_Sulfatase (GALNS)
    Polynucleotide Sequence

<400> SEQUENCE: 3

```
atggcggcgg ttgtcgcggc gacgaggtgg tggcagctgt tgctggtgct cagcgccgcg      60
gggatggggg cctcgggcgc cccgcagccc cccaacatcc tgctcctgct catggacgac     120
atgggatggg gtgacctcgg ggtgtatgga gagccctcca gagaccccc gaatttggac      180
cggatggctg cagaagggct gcttttccca aacttctatt ctgccaaccc tctgtgctcg     240
ccatcgaggg cggcactgct cacaggacgg ctacccatcc gcaatggctt ctacaccacc     300
aacgcccatg ccagaaacgc ctacacaccg caggagattg tgggcggcat cccagactcg     360
gagcagctcc tgccggagct tctgaagaag gccggctacg tcagcaagat tgtcggcaag     420
tggcatctgg gtcacaggcc ccagttccac cccctgaagc acggatttga tgagtggttt     480
ggatcccca actgccactt tggaccttat gacaacaagg ccaggcccaa catccctgtg     540
tacagggact gggagatggt tggcagatat tatgaagaat ttcctattaa tctgaagacg     600
ggggaagcca acctcaccca gatctacctg caggaagccc tggacttcat taagagacag     660
gcacggcacc accccttttt cctctactgg gctgtcgacg ccacgcacgc acccgtctat     720
gcctccaaac ccttcttggg caccagtcag cgagggcggt atggagacgc cgtccgggag     780
attgatgaca gcattgggaa gatactggag ctcctccaag acctgcacgt cgcggacaac     840
accttcgtct tcttcacgtc ggacaacggc gctgccctca tttccgcccc cgaacaaggt     900
ggcagcaacg gccccttcct gtgtgggaag cagaccacgt ttgaaggagg gatgagggag     960
cctgccctcg catggtggcc agggcacgtc actgcaggcc aggtgagcca ccagctgggc    1020
agcatcatgg acctcttcac caccagcctg gcccttgcgg gcctgacgcc gcccagcgac    1080
agggccattg atggcctcaa cctcctcccc acctcctgc agggccggct gatggacagg    1140
cctatcttct attaccgtgg cgacacgctg atggcggcca ccctcgggca gcacaaggct    1200
cacttctgga cctggaccaa ctcctgggag aacttcagac agggcattga tttctgccct    1260
gggcagaacg tttcaggggt cacaactcac aatctggaag accacacgaa gctgccctg    1320
atcttccacc tggacggaa cccaggggag aggttccccc tcagctttgc cagcgccgag    1380
taccaggagg ccctcagcag gatcacctcg gtcgtccagc agcaccagga ggccttggtc    1440
cccgcgcagc cccagctcaa cgtgtgcaac tgggcggtca tgaactgggc acctccgggc    1500
tgtgaaaagt tagggaagtg tctgacacct ccagaatcca ttcccaagaa gtgcctctgg    1560
tcccactag                                                             1569
```

<210> SEQ ID NO 4
<211> LENGTH: 522
<212> TYPE: PRT
<213> ORGANISM: Homo sapiens
<220> FEATURE:
<221> NAME/KEY: MISC_FEATURE
<223> OTHER INFORMATION: Human N-acetylgalactosamine-6-Sulfatase (GALNS)
    Polypeptide Sequence

<400> SEQUENCE: 4

```
Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30
```

-continued

```
Ile Leu Leu Leu Leu Met Asp Asp Met Gly Trp Gly Asp Leu Gly Val
            35                  40                  45

Tyr Gly Glu Pro Ser Arg Glu Thr Pro Asn Leu Asp Arg Met Ala Ala
 50                  55                  60

Glu Gly Leu Leu Phe Pro Asn Phe Tyr Ser Ala Asn Pro Leu Cys Ser
 65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
                100                 105                 110

Ile Val Gly Gly Ile Pro Asp Ser Glu Gln Leu Leu Pro Glu Leu Leu
                115                 120                 125

Lys Lys Ala Gly Tyr Val Ser Lys Ile Val Gly Lys Trp His Leu Gly
            130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
                180                 185                 190

Glu Phe Pro Ile Asn Leu Lys Thr Gly Glu Ala Asn Leu Thr Gln Ile
                195                 200                 205

Tyr Leu Gln Glu Ala Leu Asp Phe Ile Lys Arg Gln Ala Arg His His
            210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
                260                 265                 270

Gln Asp Leu His Val Ala Asp Asn Thr Phe Val Phe Phe Thr Ser Asp
            275                 280                 285

Asn Gly Ala Ala Leu Ile Ser Ala Pro Glu Gln Gly Gly Ser Asn Gly
            290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
            355                 360                 365

Leu Pro Thr Leu Leu Gln Gly Arg Leu Met Asp Arg Pro Ile Phe Tyr
370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr His Asn Leu
                420                 425                 430

Glu Asp His Thr Lys Leu Pro Leu Ile Phe His Leu Gly Arg Asp Pro
            435                 440                 445
```

```
Gly Glu Arg Phe Pro Leu Ser Phe Ala Ser Ala Glu Tyr Gln Glu Ala
    450                 455                 460

Leu Ser Arg Ile Thr Ser Val Val Gln His Gln Glu Ala Leu Val
465                 470                 475                 480

Pro Ala Gln Pro Gln Leu Asn Val Cys Asn Trp Ala Val Met Asn Trp
                    485                 490                 495

Ala Pro Pro Gly Cys Glu Lys Leu Gly Lys Cys Leu Thr Pro Pro Glu
                500                 505                 510

Ser Ile Pro Lys Lys Cys Leu Trp Ser His
            515                 520

<210> SEQ ID NO 5
<211> LENGTH: 496
<212> TYPE: PRT
<213> ORGANISM: Homo sapiens

<400> SEQUENCE: 5

Ala Pro Gln Pro Pro Asn Ile Leu Leu Leu Met Asp Asp Met Gly
1               5                   10                  15

Trp Gly Asp Leu Gly Val Tyr Gly Glu Pro Ser Arg Glu Thr Pro Asn
                20                  25                  30

Leu Asp Arg Met Ala Ala Glu Gly Leu Leu Phe Pro Asn Phe Tyr Ser
                35                  40                  45

Ala Asn Pro Leu Cys Ser Pro Ser Arg Ala Ala Leu Leu Thr Gly Arg
        50                  55                  60

Leu Pro Ile Arg Asn Gly Phe Tyr Thr Thr Asn Ala His Ala Arg Asn
65                  70                  75                  80

Ala Tyr Thr Pro Gln Glu Ile Val Gly Gly Ile Pro Asp Ser Glu Gln
                85                  90                  95

Leu Leu Pro Glu Leu Leu Lys Lys Ala Gly Tyr Val Ser Lys Ile Val
                100                 105                 110

Gly Lys Trp His Leu Gly His Arg Pro Gln Phe His Pro Leu Lys His
            115                 120                 125

Gly Phe Asp Glu Trp Phe Gly Ser Pro Asn Cys His Phe Gly Pro Tyr
    130                 135                 140

Asp Asn Lys Ala Arg Pro Asn Ile Pro Val Tyr Arg Asp Trp Glu Met
145                 150                 155                 160

Val Gly Arg Tyr Tyr Glu Glu Phe Pro Ile Asn Leu Lys Thr Gly Glu
                165                 170                 175

Ala Asn Leu Thr Gln Ile Tyr Leu Gln Glu Ala Leu Asp Phe Ile Lys
                180                 185                 190

Arg Gln Ala Arg His His Pro Phe Phe Leu Tyr Trp Ala Val Asp Ala
            195                 200                 205

Thr His Ala Arg Val Tyr Ala Ser Lys Pro Phe Leu Gly Thr Ser Gln
    210                 215                 220

Arg Gly Arg Tyr Gly Asp Ala Val Arg Glu Ile Asp Asp Ser Ile Gly
225                 230                 235                 240

Lys Ile Leu Glu Leu Leu Gln Asp Leu His Val Ala Asp Asn Thr Phe
                245                 250                 255

Val Phe Phe Thr Ser Asp Asn Gly Ala Ala Leu Ile Ser Ala Pro Glu
                260                 265                 270

Gln Gly Gly Ser Asn Gly Pro Phe Leu Cys Gly Lys Gln Thr Thr Phe
            275                 280                 285

Glu Gly Gly Met Arg Glu Pro Ala Leu Ala Trp Trp Pro Gly His Val
    290                 295                 300
```

```
Thr Ala Gly Gln Val Ser His Gln Leu Gly Ser Ile Met Asp Leu Phe
305                 310                 315                 320

Thr Thr Ser Leu Ala Leu Ala Gly Leu Thr Pro Pro Ser Asp Arg Ala
                325                 330                 335

Ile Asp Gly Leu Asn Leu Leu Pro Thr Leu Leu Gln Gly Arg Leu Met
            340                 345                 350

Asp Arg Pro Ile Phe Tyr Tyr Arg Gly Asp Thr Leu Met Ala Ala Thr
        355                 360                 365

Leu Gly Gln His Lys Ala His Phe Trp Thr Trp Thr Asn Ser Trp Glu
    370                 375                 380

Asn Phe Arg Gln Gly Ile Asp Phe Cys Pro Gly Gln Asn Val Ser Gly
385                 390                 395                 400

Val Thr Thr His Asn Leu Glu Asp His Thr Lys Leu Pro Leu Ile Phe
                405                 410                 415

His Leu Gly Arg Asp Pro Gly Glu Arg Phe Pro Leu Ser Phe Ala Ser
            420                 425                 430

Ala Glu Tyr Gln Glu Ala Leu Ser Arg Ile Thr Ser Val Val Gln Gln
        435                 440                 445

His Gln Glu Ala Leu Val Pro Ala Gln Pro Gln Leu Asn Val Cys Asn
    450                 455                 460

Trp Ala Val Met Asn Trp Ala Pro Pro Gly Cys Glu Lys Leu Gly Lys
465                 470                 475                 480

Cys Leu Thr Pro Pro Glu Ser Ile Pro Lys Lys Cys Leu Trp Ser His
                485                 490                 495
```